United States Patent [19]

Reiffenrath et al.

[11] Patent Number: 5,068,053
[45] Date of Patent: Nov. 26, 1991

[54] ETHYNE DERIVATIVES AS A COMPONENT OF LIQUID CRYSTAL PHASES

[75] Inventors: Volker Reiffenrath, Rossdorf; Eike Poetsch, Mühltal; Joachim Krause, Dieburg; Georg Weber, Erzhausen, all of Fed. Rep. of Germany

[73] Assignee: Merck Patent Gesellschaft mit Beschränkter Haftung, Darmstadt, Fed. Rep. of Germany

[21] Appl. No.: 279,594

[22] PCT Filed: Mar. 10, 1988

[86] PCT No.: PCT/DE88/00136
§ 371 Date: Nov. 25, 1988
§ 102(e) Date: Nov. 25, 1988

[87] PCT Pub. No.: WO88/07523
PCT Pub. Date: Oct. 6, 1988

[30] Foreign Application Priority Data

Mar. 27, 1987 [DE] Fed. Rep. of Germany ....... 3710069

[51] Int. Cl.$^5$ .................. C09K 19/34; C07D 239/02
[52] U.S. Cl. ........................ 252/299.61; 252/299.01; 544/298; 544/335; 546/1
[58] Field of Search .......... 252/299.01, 299.6, 299.61, 252/299.62, 299.64, 299.65, 299.66; 350/350 R, 350 S; 544/298, 335; 546/1

[56] References Cited

U.S. PATENT DOCUMENTS 3,925,482 12/1975 Jacques ............................... 252/299
4,462,923 7/1984 Boller et al. ................... 252/299.61
4,670,182 6/1987 Fujita et al. .................... 252/299.61
4,707,295 11/1987 Pohl et al. ...................... 252/299.62

FOREIGN PATENT DOCUMENTS 2257588 6/1973 Fed. Rep. of Germany .
63-60972 3/1988 Japan .

OTHER PUBLICATIONS

M. Petrzilka, "Polar Acetylenic Liquid Crystals with Broad Mesomorphic Ranges. The Positional Influence of Different C,C-Elements on the Transition Temperatures," Mol. Cryst. Liq. Cryst., 1984, vol. III, pp. 329–346.

Primary Examiner—Robert L. Stoll
Assistant Examiner—Shean C. Wu
Attorney, Agent, or Firm—Millen, White & Zelano

[57] ABSTRACT

Ethyne derivatives of the formula I $$R^1-(A^1-Z^1)_m-A^3-C\equiv C-A^4-(Z^2-A^2)_n-R^2 \qquad I$$

wherein $R^1$, $A^1$, $Z^1$, m, $A^3$, $A^4$, $Z^2$, $A^2$, n and $R^2$ have the meaning given in claim 1 are suitable as components of liquid crystal phases.

6 Claims, No Drawings

ETHYNE DERIVATIVES AS A COMPONENT OF LIQUID CRYSTAL PHASES

The invention relates to ethyne derivatives of the formula I

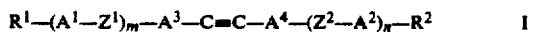

wherein
- $R^1$ and $R_2$ in each case independently of one another are an alkyl or alkenyl radical having 1 to 15 C. atoms which is unsubstituted, monosubstituted by —CN or at least monosubstituted by halogen, it also being possible for one or more $CH_2$ groups in these radicals in each case independently of one another to be replaced by —O—, —S—, —CO—, —O—CO—, —O—COO—, —CO—O— or —C≡C— such that heteroatoms are not linked directly to one another, and one of the radicals $R^1$ and $R^2$ can also be H, halogen, —CN or —NCS,
- $A^1$ and $A^2$ in each case independently of one another are a
  a) 1,4-phenylene radical, wherein one or more CH groups can also be replaced by N,
  b) trans-1,4-cyclohexylene radical, wherein one or two non-adjacent $CH_2$ groups can also be replaced by —O— and/or —S—,
  c) radical from the group comprising 1,4-cyclohexenylene, 1,4-cyclohexadienylene or 1,4-bicyclo-(2.2.2)-octylene,
  it being possible for the radicals a) and b) to be mono- or polysubstituted by halogen, cyano and/or $CH_3$,
- $Z^1$ and $Z^2$ in each case independently of one another are —CO—O—, —O—CO—, —CH$_2$O—, —OCH$_2$—, —CH$_2$CH$_2$—, —C≡C— or a single bond,
- m and n in each case independently of one another are 0 or 1,
and
- $A^3$ and $A^4$ in each case independently of one another are a
  a) 1,4-phenylene or 4,4'-biphenylene radical, wherein one or more CH groups can also be replaced by N,
  b) trans-1,4-cyclohexylene radical,
  c) radical from the group comprising 1,4-cyclohexenylene, 1,4-cyclohexadienylene and 1,4-bi-cyclo(2.2.2)octylene,
it being possible for the radicals a) and b) to be substituted once or more than once by halogen, cyano and/or $CH_3$,
with the provisos that
a) in at least one of the groups $A^3$ or $A^4$ at least one CH group is replaced by N and/or at least one of the groups $A^3$ and $A^4$ is trans-1,4-cyclohexylene or 1,4-bicyclo(2.2.2)octylene and/or at least one of the groups $A^1$, $A^2$, $A^3$ and $A^4$ is 1,4-cyclohexenylene or 1,4-cyclohexadienylene,
b) in the case where $A^3 = A^4 =$ trans-1,4-cyclohexylene and $R^1$ and $R_2$ are alkyl groups, the alkyl groups in $R^1$ and $R_2$ have a different number of C atoms,
c) $R_2$ is halogen, —NCS, an unsubstituted alkenyl radical having 1 to 15 C atoms, an alkyl or alkenyl radical having 1 to 15 C atoms which is monosubstituted by —CN or at least monosubstituted by halogen, it also being possible for one or two $CH_2$ groups in these radicals to be replaced by —S— and/or —C≡C—, or an unsubstituted alkyl radical having 1 to 15 C atoms, wherein at least one $CH_2$ group is replaced by —S— or —C≡C—, if m=n=0, $A^3$ is trans-1,4-cyclohexylene and $A^4$ is unsubstituted 1,4-phenylene and d) in the case where m=n=0 and $A^3$ =1,4-cyclohexylene, $A^4$ is a
  a) 1,4-phenylene radical, wherein one or more non-adjacent CH groups can be replaced by N,
  b) 4,4'-biphenylene radical, wherein one or more CH groups can also be replaced by N,
  c) trans-1,4-cyclohexylene radical,
  d) a (sic) radical from the group comprising 1,4-cyclohexenylene, 1,4-cyclohexadienylene or 1,4-bicyclo-(2.2.2)-octylene,
  it being possible for the radicals a , b and c) to be substituted once or more than once by halogen, cyano and/or $CH_3$.

For simplicity, in the following text Phe is an unsubstituted 1,4-phenylene group, PheX is a substituted 1,4-phenylene group (wherein X is halogen, CN and/or $CH_3$), Cyc is a 1,4-cyclohexylene group, Che is a 1,4-cyclohexenylene group, Cha is a 1,4-cyclohexadienylene group, Dio is a 1,3-dioxane-2,5-diyl group, Dit is a 1,3-dithiane-2,5-diyl group, Pyd is a pyridine-2,5-diyl group, Pyr is a pyrimidine-2,5-diyl group, Pyz is a pyrazine-2,5-diyl group, Pyn is a pyridazine-3,6-diyl group, Bco is a 1,4-bicyclo(2.2.2)octylene group and Biphe is a 4,4'-biphenylyl group, wherein one or more CH groups can also be replaced by N.

The compounds of the formula I can be used as components of liquid crystal phases, in particular for displays which are based on the principle of the twisted cell, on the guest-host effect, on the effect of deformation of orientated phases or on the effect of dynamic scattering.

Compounds of the formula I are preferably also suitable for use as components in liquid crystal phases for displays based on the ECB effect.

Similar compounds are known, for example from European Patent 111,695-A, for displays which operate by the two-frequency method.

The invention was based on the object of discovering new stable liquid crystal or mesogenic compounds which are suitable as components of liquid crystal phases. This object was achieved by providing the compounds of the formula I.

It has been found that the compounds of the formula I are outstandingly suitable as components of liquid crystal phases. In particular, stable liquid crystal phases with a relatively high optical anisotropy and negative dielectric anisotropy can be prepared with the aid of these compounds. The substances of the formula I are therefore preferably suitable for use in mixtures for ECB effects.

The ECB effect (electrically controlled birefringence) or also DOP effect (deformation of orientated phases) was described for the first time in 1971 (M.F. Schieckel and K. Fahrenschon, "Deformation of nematic liquid crystals with vertical orientation in electrical fields", Appl. Phys.Lett. 19 (1971), 3912). Works by J.F. Kahn (Appl.Phys.Lett. 20 (1972), 1193) and G. Labrunie and J. Robert (J.Appl.Phys. 44 (1973), 4869) followed.

The works by J. Robert and F. Clerc (SID 80 Digest Techn.Papers (1980), 30), J. Duchene (Displays 7

(1986), 3) and H. Schad (SID 82 Digest Techn. Papers (1982), 244) have shown that liquid crystal phases must have high values for the ratio of the elastic constants $K_3/K_1$, high values for the optical anisotropy $\Delta N$ and negative values for the dielectric anisotropy $\Delta\epsilon$ in order to be suitable for use for highly informative display elements based on the ECB effect.

Electrooptical display elements based on the ECB effect have a homeotropic edge orientation, that is to say the liquid crystal phase has a negative dielectric anisotropy.

Surprisingly, it has been found that the addition of compounds of the formula I gives liquid crystal phases which meet all the abovementioned criteria to an outstanding degree.

By providing the compounds of the formula I, the range of liquid crystal substances which are suitable, under various technological aspects, for the preparation of nematic mixtures is also quite generally widened considerably.

The compounds of the formula I have a wide field of application. Depending on the selection of the substituents, these compounds can be used as base materials from which liquid crystal phases are predominantly composed; however, compounds of the formula I can also be added to liquid crystal base materials from other classes of compounds, for example in order to optimize the dielectric and/or optical anisotropy of such a dielectric. The compounds of the formula I are furthermore suitable as intermediates for the preparation of other substances which can be used as constituents of liquid crystal phases.

The compounds of the formula I are colorless in the pure state and form liquid crystal mesophases in a temperature range which is favorably placed for electro-optical use. They are very stable towards chemicals, heat and light.

The invention thus relates to the compounds of the formula I and the use of these compounds as components of liquid crystal phases. The invention furthermore relates to liquid crystal phases containing at least one compound of the formula I or a compound containing the structural constituent $$-A^3-C\equiv C-A^4-$$

wherein $A^3$ and $A^4$ in each case independently of one another are a
 a) 1,4-phenylene radical, wherein one or more non-adjacent CH groups can also be replaced by N,
 b) 4,4'-biphenylene radical, wherein one or more CH groups can also be replaced by N,
 c) trans-1,4-cyclohexylene radical,
 d) a cis radical from the group comprising 1,4-cyclohexenylene, 1,4-cyclohexadienylene and 1,4-bicyclo(2.2.2)octylene, it being possible for the radicals a), b and c to be substituted once or more than once by halogen, cyano and/ or $CH_3$, with the proviso that in at least one of the groups $A^3$ or $A^4$ at least one CH group is replaced by N and/or at least one of the groups $A^3$ or $A^4$ is 1,4-cyclohexenylene, 1,4-cyclohexadienylene or 1,4-bicyclo(2.2.2)octylene, and liquid crystal display elements containing such phases.

$R^1$, $A^1$, $Z^1$, m, $A^3$, $A^4$, $Z^2$, $A^2$, n and $R^2$ above and below have the meaning given, unless expressly indicated otherwise.

The compounds of the formula I accordingly include compounds of the part formulae Ia (with two rings), Ib to Ie (with three rings) and If to Ii (with four rings):

| | |
|---|---|
| $R^1-A^3-C\equiv C-A^4-R_2$ | Ia |
| $R^1-A^3-C\equiv C-A^4-A^2-R^2$ | Ib |
| $R^1-A^3-C\equiv C-A^4-Z^2-A^2-R^2$ | Ic |
| $R^1-A^1-A^3-C\equiv C-A^4-R^2$ | Id |
| $R^1-A^1-Z^1-Z^3-C\equiv C-A^4-R^2$ | Ie |
| $R^1-A^1-Z^1-Z^3-C\equiv C-A^4-Z^2-A^2-R^2$ | If |
| $R^1-A^1-A^3-C\equiv C-A^4-Z^2-A^2-R^2$ | Ig |
| $R^1-A^1-Z^1-Z^3-C\equiv C-A^4-A^2-R^2$ | Ih |
| $R^1-A^1-A^3-C\equiv C-A^4-A^2-R^2$ | Ii |

The preferred compounds of the part formula Ia include those of the part formulae Iaa to Iaz:

| | |
|---|---|
| $R^1-Cyc-C\equiv C-Phe-R^2$ | Iaa |
| $R^1-Cyc-C\equiv C-PheX-R_2$ | Iab |
| $R^1-Cyc-C\equiv C-Cyc-R^2$ | Iac |
| $R^1-Che-C\equiv C-Phe-R^2$ | Iad |
| $R^1-Cha-C\equiv C-Phe-R^2$ | Iae |
| $R^1-Phe-C\equiv C-Pyd-R^2$ | Iaf |
| $R^1-Phe-C\equiv C-Pyr-R^2$ | Iag |
| $R^1-Phe-C\equiv C-Pyz-R^2$ | Iah |
| $R^1-Phe-C\equiv C-Pyn-R^2$  | Iai |
| $R^1-Phe-C\equiv C-Bco-R^2$ | Iaj |
| $R^1-Cyc-C\equiv C-Pyd-R^2$ | Iak |
| $R^1-Cyc-C\equiv C-Pyr-R^2$ | Ial |
| $R^1-Cyc-C\equiv C-Pyz-R^2$ | Iam |
| $R^1-Cyc-C\equiv C-Bco-R^2$ | Ian |
| $R^1-Cyc-C\equiv C-Biphe-R^2$ | Iao |
| $R^1-Phe-C\equiv C-Biphe-R^2$ | Iap |
| $R^1-Che-C\equiv C-PheX-R^2$ | Iaq |
| $R^1-Cha-C\equiv C-PheX-R^2$ | Iar |
| $R^1-Cyc-C\equiv C-A^4-R^2$ | Ias |
| $R^1-Che-C\equiv C-A^4-R^2$ | Iat |
| $R^1-Cha-C\equiv C-A^4-R^2$ | Iau |
| $R^1-Bco-C\equiv C-A^4-R^2$ | Iav |
| $R^1-Pyd-C\equiv C-A^4-R^2$ | Iaw |
| $R^1-Pyr-C\equiv C-A^4-R^2$ | Iax |
| $R^1-Pyz-C\equiv C-A^4-R^2$ | Iay |
| $R^1-Pyn-C\equiv C-A^4-R^2$ | Iaz |

Amongst these, those of the formulae Iab, Iad, Iaf, Iai, Iak, Iao, Iaq, Ias, Iat and Iaw are particularly preferred.

The preferred compounds of the part formulae Ib, Ic, Id and Ie include those of the part formulae I1 to I22:

| | |
|---|---|
| $R^1$—Cyc—C≡C—$A^4$—$Z^2$—$A^2$—$R_2$ | I1 |
| $R^1$—Che—C≡C—$A^4$—$Z^2$—$A^2$—$R^2$ | I2 |
| $R^1$—Cha—C≡C—$A^4$—$Z^2$—$A^2$—$R^2$ | I3 |
| $R^1$—Bco—C≡C—$A^4$—$Z^2$—$A^2$—$R^2$ | I4 |
| $R^1$—Pyd—C≡C—$A^4$—$Z^2$—$A^2$—$R^2$ | I5 |
| $R^1$—Pyr—C≡C—$A^4$—$Z^2$—$A^2$—$R^2$ | I6 |
| $R^1$—Pyz—C≡C—$A^4$—$Z^2$—$A^2$—$R^2$ | I7 |
| $R^1$—Pyn—C≡C—$A^4$—$Z^2$—$A^2$—$R^2$ | I8 |
| $R^1$—$A^3$—C≡C—Cyc—$Z^2$—$A^2$—$R_2$ | I9 |
| $R^1$—$A^3$—C≡C—Che—$Z^2$—$A^2$—$R_2$ | I10 |
| $R^1$—$A^3$—C≡C—Cha—$Z^2$—$A^2$—$R^2$ | I11 |
| $R^1$—$A^3$—C≡C—Bco—$Z^2$—$A^2$—$R^2$ | I12 |
| $R^1$—Biphe—C≡C—$A^4$—$Z^2$—$A^2$—$R^2$ | I13 |
| $R^1$—$A^3$—C≡C—Biphe—$Z^2$—$A^2$—$R^2$ | I14 |
| $R^1$—$A^3$—C≡C—Pyd—$Z^2$—$A^2$—$R^2$ | I15 |
| $R^1$—$A^3$—C≡C—Pyr—$Z^2$—$A^2$—$R_2$ | I16 |
| $R^1$—$A^3$—C≡C—Pyz—$Z^2$—$A^2$—$R^2$ | I17 |
| $R^1$—$A^3$—C≡C—Pyn—$Z^2$—$A^2$—$R^2$ | I18 |
| $R^1$—$A^3$—C≡C—$A^4$—$Z^2$—Che—$R^2$ | I19 |
| $R^1$—$A^3$—C≡C—$A^4$—$Z^2$—Cha—$R^2$ | I20 |
| $R^1$—Che—$Z^1$—$A^3$—C≡C—$A^4$—$R^2$ | I21 |
| $R^1$—Cha—$Z^1$—$A^3$——C≡C—$A^4$—$R^2$ | I22 |

Of these, those of the formulae I1, I2, I5, I6, I9, I10, I13, I14, I15, I18, I19 and I20 are particularly preferred.

The preferred compounds of the part formulae If, Ig, Ih and Ii include those of the part formulae I23 to I33:

| | |
|---|---|
| $R^1$—$A^1$—$Z^1$—Cyc—C≡C—$A^4$—$Z^2$—$A^2$—$R^2$ | I23 |
| $R^1$—$A^1$—$Z^1$—Che—C≡C—$A^4$—$Z^2$—$A^2$—$R^2$ | I24 |
| $R^1$—$A^1$—$Z^1$—Chap13 C≡C—$A^4$—$Z^2$—$A^2$—$R_2$ | I25 |
| $R^1$—$A^1$—$Z^1$—Bco—C≡C—$A^4$—$Z^2$—$A^2$—$R^2$ | I26 |
| $R^1$—$A^1$—$Z^1$—Pyd—C≡C—$A^4$—$Z^2$—$A^2$—$R^2$ | I27 |
| $R^1$—$A^1$—$Z^1$—Pyr—C≡C—$A^4$—$Z^2$—$A^2$—$R^2$ | I28 |
| $R^1$—$A^1$—$Z^1$—Pyz—C≡C—$A^4$—$Z^2$—$A^2$—$R_2$ | I29 |
| $R^1$—$A^1$—$Z^1$—Pyn—C≡C—$A^4$—$Z^2$—$A^2$—$R_2$ | I30 |
| $R^1$—$A^1$—$Z^1$—Biphe—C≡C—$A^4$—$Z^2$—$A^2$—$R_2$ | I31 |
| $R^1$—Che—$Z^1$—$A^3$—C≡C—$A^4$—$Z^2$—$A^2$—$R_2$ | I32 |
| $R^1$—Cha—$Z^1$—$A^3$—C≡C—$A^4$—$Z^2$—$A^2$—$R_2$ | I33 |

In the formulae above and below, $R^1$ and $R^2$ are preferably alkyl, alkoxy or another oxaalkyl group.

Alkenyl groups, or alkyl groups which are monosubstituted by —CN are furthermore preferred for $R^1$ and $R_2$. Alkyl groups substituted by halogen are likewise preferred. Halogen is fluorine, chlorine or bromine. Substitution by fluorine or chlorine is preferred, and the perfluoroalkyl groups, such as trifluoromethyl, pentafluoroethyl or heptafluoropropyl, are particularly preferred.

Furthermore, one of the radicals is preferably halogen, —CN or —NCS.

$A^1$ and $A^2$ are preferably Cyc, PheX or Phe, and furthermore also Che or Cha. PheX preferably denotes monosubstitution by F, Cl or CN.

$A^1$ and $A^2$ are furthermore preferably a Bco, Pyd, Dio or Pyr group.

$A^3$ and $A^4$ are preferably Cyc, Pyd, Pyr, Che, Phe or Cha, and furthermore preferably Bco, PheX, Biphe, Pyn or Pyz.

In at least one of the groups $A^3$ or A4, at least one CH group is replaced by N and/or at least one of the groups $A^3$ and $A^4$ is Cyc or Bco and/or at least one of the groups $A^1$, $A^2$, $A^3$ or $A^4$ is Che or Cha. Preferably, only one of the groups $A^3$ or $A^4$ is a pyridine, cyclohexyl or pyrimidine radical.

m and n in each case independently of one another are 0 or 1. Preferably, m+n=1.

$Z^1$ and $Z^2$ are preferably single bonds, —CO—O— or —O—CO—. —CH$_2$CH$_2$—, —C≡C—, —OCH$_2$—'0 or —CH$_2$O— are of second preference.

If $R^1$ and/or $R_2$ are alkyl radicals in which one ("alkoxy" or "oxaalkyl") or two ("alkoxyalkoxy" or "dioxaalkyl") non-adjacent CH$_2$ groups can also be replaced by 0 atoms, they can be straight-chain or branched. Preferably, they are straight-chain, have 2, 3, 4, 5, 6 or 7 C atoms and accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl or 2-, 3-, 4-, 5- or 6-oxaheptyl, and furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy, tetradecoxy, pentadecoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6- or 4,6-dioxaheptyl.

End group substituents in which one CH$_2$ group is replaced by a —C≡C— group are also particularly preferred.

Compounds of the formula I with branched end group substituents $R^1$ or $R^2$ can occasionally be of importance because of a better solubility in the customary liquid crystal base materials, but in particular as chiral doping substances if they are optically active.

Branched groups of this type as a rule contain not more than one chain branching. Preferred branched radical (sic) are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methyl-propoxy, 2-methylbutoxy, 3-methylbutoxy, 2-methylpentoxy, 3-methylpentoxy, 2-ethylhexoxy, 1-methylhexoxy, 1-methyl-heptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxy-carbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

In the case of compounds with branched end group substituents, formula I includes both the optical antipodes and racemates as well as mixtures thereof.

Of the compounds of the formula I and subformulae thereof, those in which at least one of the radicals contained therein has one of the preferred meanings given are preferred.

If $A^3$ and $A^4$ are each trans-1,4-cyclohexylene, $R^1$ and $R^2$ are preferably alkyl groups, the number of C atoms in the radical $R^1$ differing from that in the radical $R^2$. Preferred radicals in this case are alkyl radicals chosen from the group comprising methyl, ethyl, propyl, butyl, pentyl, hexyl and heptyl. Preferred combination (sic) are, for example, methyl/propyl, methyl/ pentyl, ethyl/propyl, butyl/methyl, ethyl/hexyl, ethyl/ heptyl, propyl/pentyl, propyl/heptyl, pentyl/heptyl, butyl/-hexyl or methyl/heptyl.

If $m+n=0$ and $A^3$ =a trans-1,4-cyclohexylene group, $A^4$ is preferably Phe, PheX, Pyd, Pyr or Biphe. Cyc, Che or Bco is furthermore also preferred for $A^4$.

Compounds of the formula I wherein $R^2$ is halogen, $m+n=0$, $A^3$ is a trans-1,4-cyclohexylene group and $A^4$ is an unsubstituted 1,4-phenylene group are furthermore preferred.

The 1,4-cyclohexenylene group preferably has the following structures:

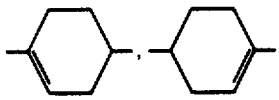

The 1,4-cyclohexadienylene group preferably has the following structure:

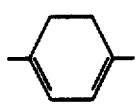

Particularly preferred smaller groups of compounds are those of the formulae 1 to 50:

| | |
|---|---|
| Alkyl—Cyc—C≡C—Phe—Halogen | 1 |
| Alkyl—Cyc—C≡C—PheX—Alkyl | 2 |
| Alkyl—Cyc—C≡C—PheX—CN | 3 |
| Alkyl—Cyc—C≡C—PheX—Halogen | 4 |
| Alkyl—Che—C≡C—Phe—Alkyl | 5 |
| Alkyl—Cha—C≡C—Phe—Alkyl | 6 |
| Alkyl-Phe—C≡C—Pyd—Alkyl | 7 |
| Alkyl—Cyc—C≡C—Pyd—Alkyl | 8 |
| Alkyl—Cyc—C≡C—Biphe—Alkoxy | 9 |
| Alkyl-Pyd—C≡C—Phe—Halogen | 10 |
| Alkoxy-Pyd—C≡C—Phe—Alkyl | 11 |
| Alkyl-Pyd—C≡C—Phe—Alkoxy | 12 |
| Alkyl-Bco—C≡C—Phe—Alkyl | 13 |
| Alkyl-Phe—C≡C—Pyn—Alkyl | 14 |
| Alkyl—Phe—C≡C—Pyn—Alkyl | 15 |
| Alkyl—Cyc—Phe—C≡C—Pyd—Alkyl | 16 |
| Alkyl—Cyc—C≡C—Phe—COO-Phe—$R^2$ | 17 |
| Alkyl—Che—C≡C—Phe—OCO-Phe—$R^2$ | 18 |
| $R^1$—Phe—C≡C—Phe—Che—$R^2$ | 19 |
| $R^1$—Cha-Phe—C≡C—Phe—$R^2$ | 20 |
| $R^1$—Cyc—CH$_2$CH$_2$—Cyc—C≡C—Phe—$R^2$ | 21 |
| $R^1$—Phe—Pyd—C≡C—Phe—$R^2$ | 22 |
| $R^1$—Pyr—C≡C-Phe—OCO—Phe—$R^2$ | 23 |
| $R^1$—Pyn—C≡C—Phe—CH$_2$O—Cyc—$R^2$ | 24 |
| $R^1$—Cyc—Phe—C≡C—Bco—$R^2$ | 25 |
| $R^1$—Cyc—C≡C—PheX—COO—Cyc—$R^2$ | 26 |
| $R^1$—Phe—CH$_2$CH$_2$—Phe—C≡C—Pyd—$R^2$ | 27 |
| $R^1$—Phe—Phe—C≡C—Cyc—Phe—$R^2$ | 28 |
| $R^1$—Phe—COO—Phe—C≡C—Pyd—Phe—$R^2$ | 29 |
| $R^1$—Cyc—C≡C—Phe—Dio—$R^2$ | 30 |
| $R^1$—Phe—OCH$_2$—Phe—C≡C—Cyc—Phe—$R^2$ | 31 |
| $R^1$—Cyc—Cyc—C≡C—Pyn—Phe—$R^2$ | 32 |
| $R^1$—Phe—COO—Cyc—C≡C—Cyc—Cyc—$R^2$ | 33 |
| Alkyl—Che—Phe—C≡C—Phe—Alkoxy | 34 |
| $R^1$—Che—Phe—C≡C—Phe—Phe—$R^2$ | 35 |
| $R^1$—Phe—Bco—C≡C—Phe—COO—Phe—$R^2$ | 36 |
| $R^1$—Cyc—Cha—C≡C—Phe—Phe—$R^2$ | 37 |
| $R^1$—Cyc—Cyc—C≡C—Pyr—Phe—$R^2$ | 38 |
| $R^1$—Phe—Phe—C≡C—Pyz—Phe—$R^2$ | 39 |
| $R^1$—Phe—Che—C≡C—Phe—Phe—$R^2$ | 40 |
| $R^1$—Phe—Pyd—C≡C—Biphe—Cyc—$R^2$ | 41 |
| $R^1$—Cyc—C≡C—Pyn—C≡C—Cyc—$R^2$ | 42 |
| Alkyl-Phe—C≡C—Pyn—Halogen | 43 |

| | |
|---|---|
| Alkyl—Cyc—C≡C—Phe—C≡C—Pyd—Alkyl | 44 |
| Alkyl—Cyc—C≡C—Cyc—C≡C—Phe—Alkyl | 45 |
| Alkyl—Che—C≡C—Phe—Alkoxy | 46 |
| Alkyl—Cyc—Cyc—C≡C—Phe—CF₃ | 47 |
| Alkyl-Phe—Cyc—C≡C—Phe—CF₃ | 48 |
| Alkyl—Cyc—C≡C—Phe—C₂F₅ | 49 |
| Alkyl—Cyc—C≡C—Phe—CF₃ | 50 |

Compounds of the formula I in which one of the groups $A^1$, $A^2$, $A^3$ and $A^4$ is a 2,3-dihalogeno-1,4-phenylene group are also preferred. In these, halogen is fluorine, chlorine or bromine. Fluorine is the preferred substituent.

Particularly preferred compounds with a 2,3-difluoro-1,4-phenylene group are those of the formulae 51 to 64:

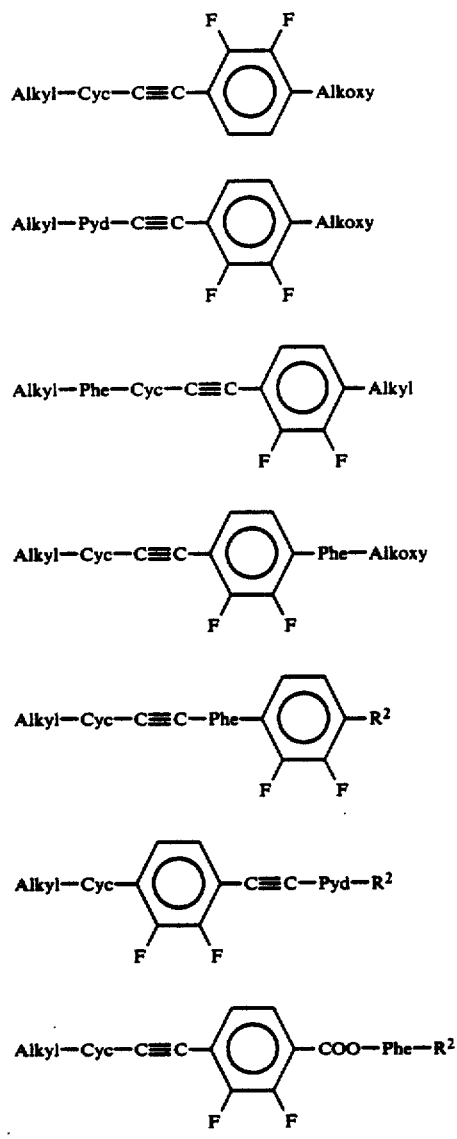

The compounds of the formula I are prepared by methods which are known per se, such as are described in the literature (for example in the standard works, such as Houben-Weyl, Methoden der Organischen Chemie (Methods of Organic Chemistry), Georg-Thieme-Verlag, Stuttgart), and in particular under reaction conditions which are known and suitable for the reactions mentioned. In this preparation, it is also possible to utilize variants which are known per se and are not mentioned in more detail here.

If desired, the starting substances can also be formed in situ such that they are not isolated from the reaction mixture but are immediately reacted further to give the compounds of the formula I.

Thus, the compounds of the formula I can be prepared by brominating the corresponding stilbenes and then subjecting the products to dehydrohalogenation. In this process, it is possible to use variants of this reaction which are known per se and are not mentioned in more detail here.

The stilbenes can be prepared by reaction of a 4-substituted benzaldehyde with a corresponding phosphorus ylide by the Wittig method or by reaction of a 4-substituted phenylethylene with a corresponding bromobenzene derivative by the Heck method.

Another possibility for the preparation of the C—C triple bond comprises a procedure in which a compound which otherwise corresponds to the formula I but contains a —CH₂—CO— group instead of the —C≡C— bond is either reacted with an inorganic acid chloride and the —CH₂—CCl₂-group then formed is dehydrohalogenated in the presence of a base, or reacted with semicarbazide and selenium dioxide. The triple bond is then introduced by heating in the presence of methyllithium.

There is furthermore the possibility of converting a corresponding benzil derivative into the ethyne derivative with hydrazine and then with HgO.

Compounds of the formula I can also be prepared via coupling of alkynyl-zinc compounds with aryl halides by a process analogous to that described by A.O. King, E. Negishi, F.J. Villani and A. Silveira in J.Org.Chem. 43 (1978) 358.

Compounds of the formula I can also be prepared via the Fritsch-Buttenberg-Wiechell rearrangement (Ann. 279, 319, 327, 332, 1894), in which 1,1-diaryl-2-halogenoethylenes are rearranged to diarylacetylenes in the presence of strong bases.

Compounds of the formula I can furthermore be prepared from 4-substituted phenyl- or cyclohexylacetylenes and aryl halides in the presence of a palladium catalyst, for example bis(triphenylphosphine)-palladium(II) chloride, and copper(I) iodide (described in Synthesis (1980) 627 or Tetrahedron Letters 27 (1986) 1171).

Compounds of the formula I are furthermore obtainable by adding a compound of the formula HX (hydrogen fluoride, chloride, bromide or cyanide) onto a corresponding cyclohexene derivative.

This addition reaction is effected, for example, in the presence of an inert solvent, for example a halogenated hydrocarbon, such as $CH_2Cl_2$ or $CHCL_3$, a nitrile, such as acetonitrile, or an amide, such as dimethylformamide (DMF) at temperatures between about −10° and +150° under pressures between about 1 and 100 bar. It may be favorable to add catalysts, for example HCN addition can be catalyzed by adding palladium bis-[2,3-O-isopropylidene-2,3-dihydroxy-1,4-bis-(diphenylphosphino)-butane].

Esters of the formula I (—CO—O— or —O—CO— group in $R^1$ and/or $R^2$ and/or $Z^2$ and/or $Z^1$ =—CO—O— or —O—CO—) can also be obtained by esterification of corresponding carboxylic acids (or their reactive derivatives) with alcohols or phenols (or their reactive derivatives). The esterification of acids with alcohols or phenols can also be carried out with DCC/DMAP.

Suitable reactive derivatives of the carboxylic acids mentioned are, in particular, the acid halides, above all the chlorides and bromides, and furthermore the anhydrides, for example also mixed anhydrides, azides or esters, in particular alkyl esters with 1–4 C atoms in the alkyl group.

Possible reactive derivatives of the alcohols or phenols mentioned are, in particular, the corresponding metal alcoholates and phenolates. In these, the metal is preferably an alkali metal, such as Na or K.

The esterification is advantageously carried out in the presence of an inert solvent. Ethers, such as diethyl ether, di-n-butyl ether, THF, dioxane or anisole, ketones, such as acetone, butanone or cyclohexanone, amides, such as DMF or phosphoric acid hexamethyltriamide, hydrocarbons, such as benzene, toluene or xylene, halogenohydrocarbons, such as carbon tetrachloride or tetrachloroethylene, and sulfoxides, such as dimethyl sulfoxide or sulfolane, are particularly suitable. Water-immiscible solvents can at the same time advantageously be used for removal by azeotropic distillation of the water formed during the esterification. An excess of an organic base, for example pyridine, quinoline or triethylamine, can occasionally also be used as the solvent for the esterification. The esterification can also be carried out in the absence of a solvent, for example by simply heating the components in the presence of sodium acetate. The reaction temperature is usually between −50° and +250°, preferably between −20° and +80°. At these temperatures, the esterification reactions are as a rule ended after 15 minutes to 48 hours.

In detail, the reaction conditions for the esterification largely depend on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, bases which are of particular importance being alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises a procedure in which the alcohol or phenol is first converted into the sodium alcoholate or phenolate or potassium alcoholate òr phenolate, for example by treatment with ethanolic sodium hydroxide solution or potassium hydroxide solution, this alcoholate or phenolate is isolated and suspended in acetone or diethyl ether, together with sodium bicarbonate or potassium carbonate, with stirring, and a solution of the acid chloride or anhydride in diethyl ether, acetone or DMF is added to this suspension, advantageously at temperatures between about −25° and +20°.

Dioxane derivatives or dithiane derivatives of the formula I (wherein one of the groups $A^1$ and/or $A^2$ is a 1,3-dioxane-2,5-diyl group or 1,3-dithiane-2,5-diyl group) are advantageously prepared by reaction of a corresponding aldehyde (or one of its reactive derivatives) with a corresponding 1,3-diol (or one of its reactive derivatives) or a corresponding 1,3-dithiol, preferably in the presence of an inert solvent, such as benzene or toluene, and/or a catalyst, for example a strong acid, such as sulfuric acid or benzene- or p-toluenesulfonic acid, at temperatures between about 20° and about 150°, preferably between 80° and 120°. Suitable reactive derivatives of the starting substances are above all acetals.

The aldehydes and 1,3-diols or 1,3-dithiols mentioned and their reactive derivatives are known in some cases and in some cases they can be prepared without difficulty by standard processes of organic chemistry from compounds which are known from the literature. For example, the aldehydes are obtainable by oxidation of corresponding alcohols or by reduction of corresponding carboxylic acids or their derivatives, the diols are obtainable by reduction of corresponding diesters and the dithiols are obtainable by reaction of corresponding dihalides with NaSH.

To prepare nitriles of the formula I (wherein $R^1$ or $R^2$ is CN and/or wherein $A^3$ and/or $A^4$ and/or $A^1$ and/or $A^2$ is substituted by at least one CN group), corresponding acid amides can be dehydrated. The amides are obtainable, for example, from corresponding esters or acid halides by reaction with ammonia. Suitable dehydrating agents are, for example, inorganic acid chlorides, such as $SOCl_2$, $PCl_3$, $PCl_5$, $POCl_3$, $SO_2Cl_2$, or $COCl_2$, and furthermore $P_2O_5$, $P_2S_5$, $AlCl_3$ (for example as a double compound with NaCl) and aromatic sulfonic acids and sulfonic acid halides. The dehydration can be carried out in the presence or absence of an inert solvent at temperatures between about 0° and 150°; possible solvents are, for example, bases, such as pyridine or triethylamine, aromatic hydrocarbons, such as benzene, toluene or xylene, or amides, such as DMF.

To prepare the abovementioned nitriles of the formula I, it is also possible to react corresponding acid halides, preferably the chlorides, with sulfamide, advantageously in an inert solvent, such as tetramethylene sulfone, at temperatures between about 80° and 150°, preferably at 120°. After customary working up, the nitriles can be isolated directly.

Ethers of the formula I (wherein $R^1$ and/or $R^2$ is an alkyl group wherein one or two $CH_2$ groups are replaced by O atoms, and/or wherein $Z^2$ and/or $Z^1$ is a $-OCH_2-$ or a $-CH_2O-$ group) are obtainable by etherification of corresponding phenols, the hydroxy compound advantageously first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This metal derivative can then be reacted with the corresponding alkyl halide, sulfonate or dialkyl Sulfate, advantageously in an inert solvent, such as acetone, 1,2-dimethoxyethane, DMF or dimethyl sulfoxide or else an excess of aqueous or aqueous-alcoholic NaOH or KOH at temperatures between about 20° and 100°.

The thioethers are prepared by methods which are known per se, such as are described in the literature (for example in the standard works, such as Houben-Weyl, Methoden der Organischen Chemie (Méthods of Organic Chemistry), Georg-Thieme-Verlag, Stuttgart), and in particular under reaction conditions which are known and suitable for the reactions mentioned. The thioethers are preferably obtained by treatment of corresponding halogen compounds, wherein halogen is chlorine, bromine or iodine, with salts of corresponding mercaptans.

These halogen compounds are either known or they can be prepared without difficulty by methods which are known per se, analogously to known compounds. Thus, for example, p-substituted halogenobenzene derivatives are accessible by halogenation of the corresponding benzene derivatives. 4-substituted cyclohexyl halides are obtainable, for example, by reduction of the corresponding 4-substituted cyclohexanones to the 4-substituted cyclohexanols and subsequent substitution by halide.

In principle, all the methods which are known for compounds which carry other substituents instead of halogen can be used for the synthesis of the halogen compounds. The synthesis variants required can be deduced by the expert by routine methods.

To prepare nitriles of the formula I (wherein $R^1$ or $R^2$ is CN and/or wherein $A^3$ and/or $A^4$ and/or $A^1$ and/or $A^2$ is substituted by at least one CN group), it is also possible to react corresponding chlorine or bromine compounds of the formula I with a cyanide, advantageously with a metal cyanide, such as NaCN, KCN or $Cu_2(CN)_2$, for example in the presence of pyridine in an inert solvent, such as dimethylformamide or N-methylpyrrolidone, at temperatures between 20° and 200°.

The liquid crystal phases according to the invention consist of 2 to 15, preferably 3 to 12, components, at least one of which is a compound of the formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-bis-cyclohexylbiphenyls, phenyl- or cyclohexylpyrimidines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers and substituted cinnamic acids.

The most important compounds which are possible constituents of such liquid crystal phases can be characterized by the formula IV

$$R^6-L-G-E-R^7 \qquad IV$$

wherein L and E are each a carbosystem from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is

| G | —CH=CH— | —N(O)=N— |
|---|---|---|
|   | —CH=CY— | —CH=N(O)— |
|   | —C≡C— | —CH₂—CH₂— |
|   | —CO—O— | —CH₂—O— |
|   | —CO—S— | —CH₂—S— |
|   | —CH=N— | —COO—Phe—COO— | a C—C single bond, Y is halogen, preferably chlorine, or —CN, and $R^6$ and $R^7$ are alkyl, alkoxy, alkanoyloxy or alkoxycarbonyloxy having up to 18, preferably up to 8, carbon atoms, or one of these radicals is by (sic) CN, NC, $NO_2$, $CF_3$, F, Cl or Br.

In most of these compounds, $R^6$ and $R^7$ differ from one another, one of these radicals usually being an alkyl or alkoxy group. Other variants of the envisaged substituents are also also (sic) customary. Many such substances or mixtures thereof are commercially available. All these substances are obtainable by methods which are known from the literature.

The phases according to the invention contain about 0.1 to 99, preferably 10 to 95% of one or more compounds of the formula I. Liquid crystal phases according to the invention containing 0.1–40, preferably 0.5–30% of one or more compounds of the formula I are furthermore preferred.

The compounds of the formula I can also be used as components of smectic or chirally tilted smectic liquid crystal phases. These phases are preferably chirally tilted smectic liquid crystal phases, the achiral base mixture of which contains, in addition to compounds of the formula I, at least one other component with negative or relatively low positive dielectric anisotropy. This (these) other component(s) of the achiral base mixture can make up to 1 to 50%, preferably 10 to 25%, of the base mixture.

The phases according to the invention are prepared in a manner which is customary per se. As a rule, the components are dissolved in one another, advantageously at elevated temperature.

The liquid crystal phases according to the invention can be modified by suitable additives so that they can be used in all the types of liquid crystal display elements which have been disclosed to date.

Such additives are known to the expert and are described in detail in the literature. For example, it is possible to add conductive salts, preferably ethyl- dimethyl-dodecyl-ammonium 4-hexyloxybenzoate, tetrabutylammonium tetraphenylboranate or complex salts of crown ethers (compare, for example, I. Haller et al., Mol. Cryst. Liq. Cryst. Volume 24, pages 249–258 (1973)) to improve the conductivity, dichroic dyestuffs to prepare colored guest-host systems or substances for modifying the dielectric anisotropy, the viscosity and/or the orientation of the nematic phases. Such substances are described, for example, in German Offenlegungsschrift 2,209,127, 2,240,864, 2,321,632, 2,338,281, 2,450,088, 2,637,430, 2,853,728 and 2,902,177.

The following examples are intended to illustrate the invention, without limiting it. M.=melting point, C.=clear point. Percentage data above and below are percentages by weight; all the temperatures are stated in degrees Celsius. "Customary working up" means: water is added, the mixture is extracted with methylene chloride, the organic phase is separated off, dried and evaporated, and the product is purified by crystallization and/or chromatography.

EXAMPLE 1

0.2 mmol of bis-(triphenylphosphine)-palladium(II) chloride and 0.1 mmol of copper(I) iodide are added to a mixture of 0.01 mol of 2-fluoro-4-bromobenzonitrile, 0.01 mol of 4-pentylcyclohexylacetylene (which can be prepared, for example, from the corresponding cyclohexanecarbaldehyde by the method of Corey, Fuchs in Tetrahedron Letters (1972) 3769) and 40 ml of triethylamine at room temperature and the mixture is stirred for 12 hours. The reaction can be monitored with the aid of thin layer chromatography. When the reaction has ended, the suspension is filtered and the filtrate is evaporated. Purification by chromatography and/or crystallization gives 1-(trans-4-pentylcyclohexyl)-2-(3-fluoro-4-cyano- phenyl)-acetylene of M.=38° and C.=40.3°.

The following are prepared analogously:

1-(trans-4-methylcyclohexyl)-2-(3-fluoro-4-cyanophenyl)acetylene
1-(trans-4-ethylcyclohexyl)-2-(3-fluoro-4-cyanophenyl)acetylene
1-(trans-4-propylcyclohexyl)-2-(3-fluoro-4-cyanophenyl)acetylene
1-(trans-4-butylcyclohexyl)-2-(3-fluoro-4-cyanophenyl)acetylene
1-(trans-4-hexylcyclohexyl)-2-(3-fluoro-4-cyanophenyl)acetylene
1-(trans-4-heptylcyclohexyl)-2-(3-fluoro-4-cyanophenyl)acetylene
1-(trans-4-methylcyclohexyl)-2-(3-chloro-4-cyanophenyl)acetylene
1-(trans-4-ethylcyclohexyl)-2-(3-chloro-4-cyanophenyl)acetylene
1-(trans-4-propylcyclohexyl)-2-(3-chloro-4-cyanophenyl)acetylene
1-(trans-4-butylcyclohexyl)-2-(3-chloro-4-cyanophenyl)acetylene
1-(trans-4-pentylcyclohexyl)-2-(3-chloro-4-cyanophenyl)acetylene acetylene
1-(trans-4-hexylcyclohexyl)-2-(3-chloro-4-cyanophenyl)acetylene
1-(trans-4-heptylcyclohexyl)-2-(3-chloro-4-cyanophenyl)acetylene
1-(trans-4-methylcyclohexyl)-2-(4-fluorophenyl)-acetylene
1-(trans-4-ethylcyclohexyl)-2-(4-fluorophenyl)-acetylene
1-(trans-4-propylcyclohexyl)-2-(4-fluorophenyl)-acetylene
1-(trans-4-butylcyclohexyl)-2-(4-fluorophenyl)-acetylene
1-(trans-4-pentylcyclohexyl)-2-(4-fluorophenyl)-acetylene
1-(trans-4-hexylcyclohexyl)-2-(4-fluorophenyl)-acetylene
1-(trans-4-heptylcyclohexyl)-2-(4-fluorophenyl)-acetylene
1-(trans-4-octylcyclohexyl)-2-(4-fluorophenyl)-acetylene
1-(trans-4-nonylcyclohexyl)-2-(4-fluorophenyl)-acetylene
1-(trans-4-decylcyclohexyl)-2-(4-fluorophenyl)-acetylene
1-(trans-4-methylcyclohexyl)-2-(4-chlorophenyl)-acetylene
1-(trans-4-ethylcyclohexyl)-2-(4-chlorophenyl)-acetylene
1-(trans-4-propylcyclohexyl)-2-(4-chlorophenyl)-acetylene
1-(trans-4-butylcyclohexyl)-2-(4-chlorophenyl)-acetylene
1-(trans-4-pentylcyclohexyl)-2-(4-chlorophenyl)-acetylene
1-(trans-4-hexylcyclohexyl)-2-(4-chlorophenyl)-acetylene
1-(trans-4-heptylcyclohexyl)-2-(4-chlorophenyl)-acetylene
1-(trans-4-octylcyclohexyl)-2-(4-chlorophenyl)-acetylene
1-(trans-4-nonylcyclohexyl)-2-(4-chlorophenyl)-acetylene
1-(trans-4-decylcyclohexyl)-2-(4-chlorophenyl)-acetylene
1-(trans-4-methylcyclohexyl)-2-(2,4-difluorophenyl)acetylene
1-(trans-4-ethylcyclohexyl)-2-(2,4-difluorophenyl)acetylene
1-(trans-4-propylcyclohexyl)-2-(2,4-difluorophenyl)acetylene
1-(trans-4-butylcyclohexyl)-2-(2,4-difluorophenyl)acetylene
1-(trans-4-pentylcyclohexyl)-2-(2,4-difluorophenyl)acetylene
1-(trans-4-hexylcyclohexyl)-2-(2,4-difluorophenyl)acetylene
1-(trans-4-heptylcyclohexyl)-2-(2,4-difluorophenyl)acetylene acetylene 1-(trans-4-methylcyclohexyl)-2-(3,4-difluorophenyl)acetylene
1-(trans-4-ethylcyclohexyl)-2-(3,4-difluorophenyl)acetylene
1-(trans-4-propylcyclohexyl)-2-(3,4-difluorophenyl)acetylene
1-(trans-4-butylcyclohexyl)-2-(3,4-difluorophenyl)acetylene
1-(trans-4-pentylcyclohexyl)-2-(3,4-difluorophenyl)acetylene
1-(trans-4-hexylcyclohexyl)-2-(3,4-difluorophenyl)acetylene
1-(trans-4-heptylcyclohexyl)-2-(3,4-difluorophenyl)acetylene
1-[trans-4-(4-methylphenyl)cyclohexyl]-2-(4-methoxyphenyl)-acetylene
1-[trans-4-(4-ethylphenyl)cyclohexyl]-2-(4-methoxyphenyl)-acetylene
1-[trans-4-(4-propylphenyl)cyclohexyl]-2-(4-methoxyphenyl)-acetylene
1-[trans-4-(4-butylphenyl)cyclohexyl]-2-(4-methoxyphenyl)-acetylene
1-[trans-4-(4-pentylphenyl)cyclohexyl]-2-(4-methoxyphenyl)-acetylene
1-[trans-4-(4-hexylphenyl)cyclohexyl]-2-(4-methoxyphenyl)-acetylene
1-[trans-4-(4-heptylphenyl)cyclohexyl]-2-(4-methoxyphenyl)-acetylene
1-[trans-4-(4-methylphenyl)cyclohexyl]-2-(4-ethoxyphenyl)acetylene
1-[trans-4-(4-ethylphenyl)cyclohexyl]-2-(4-ethoxyphenyl)acetylene
1-[trans-4-(4-propylphenyl)cyclohexyl]-2-(4-ethoxyphenyl)acetylene
1-[trans-4-(4-butylphenyl)cyclohexyl]-2-(4-ethoxyphenyl)acetylene acetylene
1-[trans-4-(4-hexylphenyl)cyclohexyl]-2-(4-ethoxyphenyl)acetylene
1-[trans-4-(4-heptylphenyl)cyclohexyl]-2-(4-ethoxyphenyl)acetylene
1-[trans-4-(4-methylphenyl)cyclohexyl]-2-(4-propoxyphenyl)-acetylene
1-[trans-4-(4-ethylphenyl)cyclohexyl]-2-(4-propoxyphenyl)acetylene
1-[trans-4-(4-propylphenyl)cyclohexyl]-2-(4-propoxyphenyl)-acetylene
1-[trans-4-(4-butylphenyl)cyclohexyl]-2-(4-propoxyphenyl)acetylene
1-[trans-4-(4-pentylphenyl)cyclohexyl]-2-(4-propoxyphenyl)-acetylene
1-[trans-4-(4-hexylphenyl)cyclohexyl]-2-(4-propoxyphenyl)phenyl]-acetylene
1-[trans-4-(4-heptylphenyl)cyclohexyl]-2-(4-propoxyphenyl)-acetylene
1-[trans-4-(4-methylphenyl)cyclohexyl]-2-(4-butyloxyphenyl)-acetylene
1-[trans-4-(4-ethylphenyl)cyclohexyl]-2-(4-butyloxyphenyl)-acetylene
1-[trans-4-(4-propylphenyl)cyclohexyl]-2-(4-butyloxyphenyl)-acetylene
1-[trans-4-(4-butylphenyl)cyclohexyl]-2-(4-butyloxyphenyl)-acetylene
1-[trans-4-(4-pentylphenyl)cyclohexyl]-2-(4-butyloxyphenyl)-acetylene
1-[trans-4-(4-hexylphenyl)cyclohexyl]-2-(4-butyloxyphenyl)-acetylene
1-[trans-4-(4-heptylphenyl)cyclohexyl]-2-(4-butyloxyphenyl)-acetylene
1-[trans-4-(4-methylphenyl)cyclohexyl]-2-(4-pentyloxyphenyl)-acetylene
1-[trans-4-(4-ethylphenyl)cyclohexyl]-2-(4-pentyloxyphenyl)-acetylene
1-[trans-4-(4-propylphenyl)cyclohexyl]-2-(4-pentyloxyphenyl)-acetylene
1-[trans-4-(4-butylphenyl)cyclohexyl]-2-(4-pentyloxyphenyl)-acetylene
1-[trans-4-(4-pentylphenyl)cyclohexyl]-2-(4-pentyloxyphenyl)-acetylene
1-[trans-4-(4-hexylphenyl)cyclohexyl]-2-(4-pentyloxyphenyl)-acetylene
1-[trans-4-(4-heptylphenyl)cyclohexyl]-2-(4-pentyloxyphenyl)-acetylene
1-[trans-4-(4-methylphenyl cyclohexyl]-2-(4-hexyloxyphenyl)-acetylene
1-[trans-4-(4-ethylphenyl)cyclohexyl]-2-(4-hexyloxyphenyl)-acetylene
1-[trans-4-(4-propylphenyl)cyclohexyl]-2-(4-hexyloxyphenyl)-acetylene
1-[trans-4-(4-butylphenyl)cyclohexyl]-2-(4-hexyloxyphenyl)-acetylene
1-[trans-4-(4-pentylphenyl cyclohexyl]-2-(4-hexyloxyphenyl)-acetylene
1-[trans-4-(4-hexylphenyl)cyclohexyl]-2-(4-hexyloxyphenyl)-acetylene
1-[trans-4-(4-heptylphenyl)cyclohexyl]-2-(4-hexyloxyphenyl)-acetylene
1-[trans-4-(4-methylphenyl)cyclohexyl]-2-(4-methylphenyl)acetylene
1-[trans-4-(4-ethylphenyl)cyclohexyl]-2-(4-methylphenyl)acetylene
1-[trans-4-(4-propylphenyl)cyclohexyl]-2-(4-methylphenyl)acetylene
1-[trans-4-(4-butylphenyl)cyclohexyl]-2-(4-methylphenyl)acetylene
1-[trans-4-(4-pentylphenyl)cyclohexyl]-2-(4-methylphenyl)acetylene
1-[trans-4-(4-hexylphenyl)cyclohexyl]-2-(4-methylphenyl)acetylene
1-[trans-4-(4-heptylphenyl)cyclohexyl]-2-(4-methylphenyl)acetylene
1[trans-4-(4-octylphenyl)cyclohexyl]-2-(4-methylphenyl)-
1-[trans-4-(4-nonylphenyl)cyclohexyl]-2-(4-methylphenyl)acetylene
1-[trans-4-(4-decylphenyl)cyclohexyl]-2 (4-methylphenyl)acetylene
1-[trans-4-(4-methylphenyl)cyclohexyl]-2-(4-ethylphenyl)acetylene
1-[trans-4-(4-ethylphenyl)cyclohexyl]-2-(4-ethylphenyl)acetylene
1-[trans-4-(4-propylphenyl)cyclohexyl]-2-(4-ethylphenyl)acetylene
1-[trans-4-(4-butylphenyl)cyclohexyl]-2-(4-ethylphenyl)acetylene
1-[trans-4-(4-pentylphenyl)cyclohexyl]-2-(4-ethylphenyl)acetylene
1-[trans-4-(4-hexylphenyl)cyclohexyl]-2-(4-ethylphenyl)acetylene
1-[trans-4-(4-heptylphenyl)cyclohexyl]-2-(4-ethylphenyl)acetylene
1-[trans-4-(4-methylphenyl)cyclohexyl]-2-(4-propylphenyl)acetylene
1-[trans-4-(4-ethylphenyl)cyclohexyl]-2-(4-propylphenyl)acetylene
1-[trans-4-(4-propylphenyl)cyclohexyl]-2-(4-propylphenyl)acetylene 1-[trans-4-(4-butylphenyl)cyclohexyl]-2-(4-propylphenyl)acetylene
1-[trans-4-(4-pentylphenyl)cyclohexyl]-2-(4-propylphenyl)acetylene
1-[trans-4-(4-hexylphenyl)cyclohexyl]-2-(4-propylphenyl)acetylene
1-[trans-4-(4-heptylphenyl)cyclohexyl]-2-(4-propylphenyl)acetylene
1-[trans-4-(4-methylphenyl)cyclohexyl]-2-(4-butylphenyl)acetylene
1-[trans-4-(4-ethylphenyl)cyclohexyl]-2-(4-butylphenyl)acetylene
1-[trans-4-(4-propylphenyl)cyclohexyl]-2-(4-butylphenyl)acetylene
1-[trans-4-(4-butylphenyl)cyclohexyl]-2-(4-butylphenyl)acetylene
1-[trans-4-(4-pentylphenyl)cyclohexyl]-2-(4-butylphenyl)acetylene
1-[trans-4-(4-hexylphenyl)cyclohexyl]-2-(4-butylphenyl)acetylene
1-[trans-4-(4-heptylphenyl)cyclohexyl]-2-(4-butylphenyl)acetylene
1-[trans-4-(4-methylphenyl)cyclohexyl]-2-(4-pentylphenyl)acetylene
1-[trans-4-(4-ethylphenyl)cyclohexyl]-2-(4-pentylphenyl)acetylene
1-[trans-4-(4-propylphenyl)cyclohexyl]-2-(4-pentylphenyl)acetylene
1-[trans-4-(4-butylphenyl)cyclohexyl]-2-(4-pentylphenyl)acetylene
1-[trans-4-(4-pentylphenyl)cyclohexyl]-2-(4-pentylphenyl)acetylene
1-[trans-4-(4-hexylphenyl)cyclohexyl]-2-(4-pentylphenyl)acetylene
1-[trans-4-(4-heptylphenyl)cyclohexyl]-2-(4-pentylphenyl)acetylene
1-[trans-4-(4-methylphenyl)cyclohexyl]-2-(4-hexylphenyl)acetylene
1-[trans-4-(4-ethylphenyl)cyclohexyl]-2-(4-hexylphenyl)acetylene
1-[trans-4-(4-propylphenyl)cyclohexyl]-2-(4-hexylphenyl)acetylene
1-[trans-4-(4-butylphenyl)cyclohexyl]-2-(4-hexylphenyl)acetylene
1-[trans-4-(4-pentylphenyl)cyclohexyl]-2-(4-hexylphenyl)acetylene
1-[trans-4-(4-hexylphenyl cyclohexyl]-2-(4-hexylphenyl)acetylene
1-[trans-4-(4-heptylphenyl)cyclohexyl]-2-(4-hexylphenyl)acetylene
1-[trans-4-(4-methylphenyl)cyclohexyl]-2-(4-heptylphenyl)acetylene
1-[trans-4-(4-ethylphenyl)cyclohexyl]-2-(4-heptylphenyl)acetylene
1-[trans-4-(4-propylphenyl)cyclohexyl]-2-(4-heptylphenyl)acetylene
1-[trans-4-(4-butylphenyl)cyclohexyl]-2-(4-heptylphenyl)acetylene
1-[trans-4-(4-pentylphenyl)cyclohexyl]-2-(4-heptylphenyl)acetylene
1-[trans-4-(4-hexylphenyl)cyclohexyl]-2-(4-heptylphenyl)acetylene
1-[trans-4-(4-heptylphenyl)cyclohexyl]-2-(4-heptylphenyl)acetylene
1-[trans-4-(4-methylphenyl)cyclohexyl]-2-(4-octylphenyl)acetylene
1-[trans-4-(4-ethylphenyl)cyclohexyl]-2-(4-octylphenyl)acetylene
1-[trans-4-(4-propylphenyl)cyclohexyl]-2-(4-octylphenyl)acetylene
1-[trans-4-(4-butylphenyl)cyclohexyl]-2-(4-octylphenyl)acetylene
1-[trans-4-(4-pentylphenyl)cyclohexyl]-2-(4-octylphenyl)acetylene
1-[trans-4-(4-hexylphenyl)cyclohexyl]-2-(4-octylphenyl)acetylene
1-[trans-4-(4-heptylphenyl)cyclohexyl]-2-(4-octylphenyl)acetylene
1-[trans-4-(4-methylphenyl)cyclohexyl]-2-(3-fluoro-4-propylphenyl)-acetylene
1-[trans-4-(4-ethylphenyl)cyclohexyl]-2-(3-fluoro-4-propylphenyl)-acetylene
1-[trans-4-(4-propylphenyl)cyclohexyl]-2-(3-fluoro-4-propylphenyl)-acetylene
1-[trans-4-(4-butylphenyl)cyclohexyl]-2-(3-fluoro-4-propylphenyl)-acetylene
1-[trans-4-(4-pentylphenyl)cyclohexyl]-2-(3-fluoro-4-propylphenyl)-acetylene
1-[trans-4-(4-hexylphenyl)cyclohexyl]-2-(3-fluoro-4-propylphenyl)-acetylene
1-[trans-4-(4-heptylphenyl)cyclohexyl]-2-(3-fluoro-4-propylphenyl)-acetylene
1-[trans-4-(4-methylphenyl)cyclohexyl]-2-(3-fluoro-4-butylphenyl)-acetylene
1-[trans-4-(4-ethylphenyl)cyclohexyl]-2-(3-fluoro-4-butylphenyl)-acetylene
1-[trans-4-(4-propylphenyl cyclohexyl]-2-(3-fluoro-4-butylphenyl)-acetylene
1-[trans-4-(4-butylphenyl)cyclohexyl]-2-(3-fluoro-4-butylphenyl)-acetylene
1-[trans-4-(4-pentylphenyl cyclohexyl]-2-(3-fluoro-4-butylphenyl)-acetylene
1-[trans-4-(4-hexylphenyl)cyclohexyl]-2-(3-fluoro-4-butylphenyl)-acetylene
1-[trans-4-(4-heptylphenyl)cyclohexyl]-2-(3-fluoro-4-butylphenyl)-acetylene
1-[trans-4-(4-methylphenyl)cyclohexyl]-2-(3-fluoro-4-pentylphenyl)-acetylene
1-[trans-4-(4-ethylphenyl cyclohexyl]-2-(3-fluoro-4-pentylphenyl)-acetylene
1-[trans-4-(4-propylphenyl)cyclohexyl]-2-(3-fluoro-4-pentylacetylene
1-[trans-4-(4-butylphenyl)cyclohexyl]-2-(3-fluoro-4-pentylphenyl)-acetylene
1-[trans-4-(4-pentylphenyl)cyclohexyl]-2-(3-fluoro-4-pentylphenyl)-acetylene
1-[trans-4-(4-hexylphenyl)cyclohexyl]-2-(3-fluoro-4-pentylphenyl)-acetylene
1-[trans-4-(4-heptylphenyl)cyclohexyl]-2-(3-fluoro-4-pentylphenyl)-acetylene
1-[trans-4-(4-octylphenyl)cyclohexyl]-2-(3-fluoro-4-pentylphenyl)-acetylene
1-[trans-4-(4-nonylphenyl)cyclohexyl]-2-(3-fluoro-4-pentylphenyl)-acetylene
1-[trans-4-(4-decylphenyl)cyclohexyl]-2-(3-fluoro-4-pentylphenyl)-acetylene
1-[trans-4-(4-methylphenyl)cyclohexyl]-2-(3-fluoro-4-hexylphenyl)-acetylene
1-[trans-4-(4-ethylphenyl)cyclohexyl]-2-(3-fluoro-4-hexylphenyl)-acetylene
1-[trans-4-(4-propylphenyl)cyclohexyl]-2-(3-fluoro-4-hexylphenyl)-acetylene
1-[trans-4-(4-butylphenyl)cyclohexyl]-2-(3-fluoro-4-hexylphenyl)-acetylene
1-[trans-4-(4-pentylphenyl)cyclohexyl]-2-(3-fluoro-4-hexylphenyl)-acetylene 1-[trans-4-(4-hexylphenyl)cyclohexyl]-2-(3-fluoro-4-hexylphenyl)-acetylene
1-[trans-4-(4-heptylphenyl)cyclohexyl]-2-(3-fluoro-4-hexylphenyl)-acetylene
1-[trans-4-(4-methylphenyl)cyclohexyl]-2-(3-chloro-4-propylphenyl)-acetylene
1-[trans-4-(4-ethylphenyl)cyclohexyl]-2-(3-chloro-4-propylphenyl)-acetylene
1-[trans-4-(4-propylphenyl)cyclohexyl]-2-(3-chloro-4-propylphenyl)-acetylene
1-[trans-4-(4-butylphenyl)cyclohexyl]-2-(3-chloro-4-propylphenyl)-acetylene
1-[trans-4-(4-pentylphenyl)cyclohexyl]-2-(3-chloro-4-propylphenyl)-acetylene
1-[trans-4-(4-hexylphenyl)cyclohexyl]-2-(3-chloro-4-propylphenyl)-acetylene
1-[trans-4-(4-heptylphenyl)cyclohexyl]-2-(3-chloro-4-propylphenyl)-acetylene
1-[trans-4-(4-methylphenyl)cyclohexyl]-2-(3-cyano-4-propylphenyl)-acetylene
1-[trans-4-(4-ethylphenyl)cyclohexyl]-2-(3-cyano-4-propylphenyl)-acetylene
1-[trans-4-(4-propylphenyl)cyclohexyl]-2-(3-cyano-4-propylphenyl)-acetylene
1-[trans-4-(4-butylphenyl)cyclohexyl]-2-(3-cyano-4-propylphenyl)-acetylene
1-[trans-4-(4-pentylphenyl)cyclohexyl]-2-(3-cyano-4-propylphenyl)-acetylene
1-[trans-4-(4-hexylphenyl)cyclohexyl]-2-(3-cyano-4-propylphenyl)-acetylene
1-[trans-4-(4-heptylphenyl)cyclohexyl]-2-(3-cyano-4-propylphenyl)-acetylene
1-[trans-4-(4-methylphenyl)cyclohexyl -2-(3-chloro-4-butylphenyl)-acetylene
1-[trans-4-(4-ethylphenyl)cyclohexyl]-2-(3-chloro-4-butylphenyl)-acetylene
1-[trans-4-(4-propylphenyl)cyclohexyl]-2-(3-chloro-4-butylphenyl)-acetylene
1-[trans-4-(4-butylphenyl)cyclohexyl]-2-(3-chloro-4-butylphenyl)-acetylene
1-[trans-4-(4-pentylphenyl)cyclohexyl]-2-(3-chloro-4-butylphenyl)-acetylene
1-[trans-4-(4-hexylphenyl)cyclohexyl]-2-(3-chloro-4-butylphenyl)-acetylene
1-[trans-4-(4-heptylphenyl)cyclohexyl]-2-(3-chloro-4-butylphenyl)-acetylene
1-[trans-4-(4-methylphenyl)cyclohexyl]-2-(3-cyano-4-butylphenyl)-acetylene
1-[trans-4-(4-ethylphenyl)cyclohexyl]-2-(3-cyano-4-butylphenyl)-acetylene
1-[trans-4-(4-propylphenyl)cyclohexyl]-2-(3-cyano-4-butylphenyl)-acetylene
1-[trans-4-(4-butylphenyl)cyclohexyl]-2-(3-cyano-4-butylphenyl)-acetylene
1-[trans-4-(4-pentylphenyl)cyclohexyl]-2-(3-cyano-4-butylphenyl)-acetylene
1-[trans-4-(4-hexylphenyl)cyclohexyl]-2-(3-cyano-4-butylphenyl)-acetylene
1-[trans-4-(4-heptylphenyl)cyclohexyl]-2-(3-cyano-4-butylphenyl)-acetylene
1-[trans-4-(4-methylphenyl)cyclohexyl]-2-(2-fluoro-4-pentylphenyl)-acetylene
1-[trans-4-(4-ethylphenyl cyclohexyl]-2-(2-fluoro-4-pentylphenyl)-acetylene
1-[trans-4-(4-propylphenyl)cyclohexyl]-2-(2-fluoro-4-pentylphenyl)-acetylene
1-[trans-4-(4-butylphenyl)cyclohexyl]-2-(2-fluoro-4-pentylphenyl)-acetylene
1-[trans-4-(4-pentylphenyl)cyclohexyl]-2-(2-fluoro-4-pentylphenyl)-acetylene
1-[trans-4-(4-hexylphenyl)cyclohexyl]-2-(2-fluoro-4-pentylphenyl)-acetylene
1-[trans-4-(4-heptylphenyl)cyclohexyl]-2-(2-fluoro-4-pentylphenyl)-acetylene
1-[trans-4-(4-methylphenyl)cyclohexyl]-2-(3-chloro-4-hexylphenyl)-acetylene
1-[trans-4-(4-ethylphenyl)cyclohexyl]-2-(3-chloro-4-hexylphenyl)-acetylene
1-[trans-4-(4-propylphenyl)cyclohexyl]-2-(3-chloro-4-hexylphenyl)-acetylene
1-[trans-4-(4-butylphenyl)cyclohexyl]-2-(3-chloro-4-hexylphenyl)-acetylene
1-[trans-4-(4-pentylphenyl)cyclohexyl]-2-(3-chloro-4-hexylphenyl)-acetylene
1-[trans-4-(4-hexylphenyl)cyclohexyl]-2-(3-chloro-4-hexylphenyl)-acetylene
1-[trans-4-(4-heptylphenyl)cyclohexyl]-2-(3-chloro-4-hexylphenyl)-acetylene
1-[trans-4-(4-methylphenyl)cyclohexyl]-2-(2-cyano-4-heptylphenyl)-acetylene
1-[trans-4-(4-ethylphenyl)cyclohexyl]-2-(2-cyano-4-heptylphenyl)-acetylene
1-[trans-4-(4-propylphenyl)cyclohexyl]-2-(2-cyano-4-heptylphenyl)-acetylene
1-[trans-4-(4-butylphenyl)cyclohexyl]-2-(2-cyano-4-heptylphenyl)-acetylene
1-[trans-4-(4-pentylphenyl)cyclohexyl]-2-(2-cyano-4-heptylphenyl)-acetylene
1-[trans-4-(4-hexylphenyl)cyclohexyl]-2-(2-cyano-4-heptylphenyl)-acetylene
1-[trans-4-(4-heptylphenyl)cyclohexyl]-2-(2-cyano-4-heptylphenyl)-acetylene
1-[trans-4-(4-methyloxyphenyl)cyclohexyl]-2-(4-propylphenyl)-acetylene
1-[trans-4-(4-ethyloxyphenyl)cyclohexyl]-2-(4-propyl-phenyl)-acetylene
1-[trans-4-(4-propyloxyphenyl)cyclohexyl]-2-(4-propyl-phenyl)-acetylene
1-[trans-4-(4-butyloxyphenyl)cyclohexyl]-2-(4-propyl-phenyl)-acetylene
1-[trans-4-(4-pentyloxyphenyl)cyclohexyl]-2-(4-propyl-phenyl)-acetylene
1-[trans-4-(4-hexyloxyphenyl)cyclohexyl]-2-(4-propyl-phenyl)-acetylene
1-[trans-4-(4-heptyloxyphenyl)cyclohexyl]-2-(4-propyl-phenyl)-acetylene
1-[trans-4-(4-octyloxyphenyl)cyclohexyl]-2-(4-propyl-phenyl)-acetylene
1-[trans-4-(4-nonyloxyphenyl)cyclohexyl]-2-(4-propyl-phenyl)-acetylene
1-[trans-4-(4-decyloxyphenyl)cyclohexyl]-2-(4-propyl-phenyl)-acetylene
1-[trans-4-(4-methyloxyphenyl)cyclohexyl]-2-(4-butyl-phenyl)-acetylene
1-[trans-4-(4-ethyloxyphenyl cyclohexyl]-2-(4-butyl-phenyl)-acetylene
1-[trans-4-(4-propyloxyphenyl)cyclohexyl]-2-(4-butyl-phenyl)-acetylene
1-[trans-4-(4-butyloxyphenyl)cyclohexyl]-2-(4-butyl-phenyl)-acetylene
1-[trans-4-(4-pentyloxyphenyl)cyclohexyl]-2-(4-butyl-phenyl)-acetylene
1-[trans-4-(4-hexyloxyphenyl)cyclohexyl]-2-(4-butyl-phenyl)-acetylene
1-[trans-4-(4-heptyloxyphenyl)cyclohexyl]-2-(4-butyl-phenyl)-acetylene 1-[trans-4-(4-methyloxyphenyl)cyclohexyl]-2-(4-pentylphenyl)-acetylene
1-[trans-4-(4-ethyloxyphenyl)cyclohexyl]-2-(4-pentylphenyl)-acetylene
1-[trans-4-(4-propyloxyphenyl)cyclohexyl]-2-(4-pentylphenyl)-acetylene
1-[trans-4-(4-butyloxyphenyl)cyclohexyl]-2-(4-pentylphenyl)-acetylene
1-[trans-4-(4-pentyloxyphenyl)cyclohexyl]-2-(4-pentylphenyl)-acetylene
1-[trans-4-(4-hexyloxyphenyl)cyclohexyl]-2-(4-pentylphenyl)-acetylene
1-[trans-4-(4-heptyloxyphenyl)cyclohexyl]-2-(4-pentylphenyl)-acetylene
1-[trans-4-(4-methyloxyphenyl)cyclohexyl]-2-(4-hexylphenyl)-acetylene
1-[trans-4-(4-ethyloxyphenyl)cyclohexyl]-2-(4-hexylphenyl)-acetylene
1-[trans-4-(4-propyloxyphenyl)cyclohexyl]-2-(4-hexylphenyl)-acetylene
1-[trans-4-(4-butyloxyphenyl)cyclohexyl]-2-(4-hexylphenyl)-acetylene
1-[trans-4-(4-pentyloxyphenyl)cyclohexyl]-2-(4-hexylphenyl)-acetylene
1-[trans-4-(4-hexyloxyphenyl)cyclohexyl]-2-(4-hexylphenyl)-acetylene
1- trans-4- trans-4-methylcyclohexyl)cyclohexyl]-2-(4-hexylpropylphenyl)-acetylene
1-[trans-4-(trans-4-ethylcyclohexyl)cyclohexyl]-2-(4-propylphenyl)-acetylene
1-[trans-4- trans-4-propylcyclohexyl)cyclohexyl]-2-(4-propylphenyl)-acetylene
1-[trans-4-(trans-4-butylcyclohexyl)cyclohexyl]-2-(4-propylphenyl)-acetylene
1-[trans-4-(trans-4-pentylcyclohexyl)cyclohexyl]-2-(4-propylphenyl)-acetylene
1-[trans-4-(trans-4-hexylcyclohexyl)cyclohexyl]-2-(4-propylphenyl)-acetylene
1-[trans-4-(trans-4-heptylcyclohexyl)cyclohexyl]-2-(4-propylphenyl)-acetylene
1-[trans-4-(trans-4-methylcyclohexyl)cyclohexyl]-2-(4-butylphenyl)-acetylene
1-[trans-4-(trans-4-ethylcyclohexyl)cyclohexyl]-2-(4-butylphenyl)-acetylene
1-[trans-4-(trans-4-propylcyclohexyl)cyclohexyl]-2-(4-butylphenyl)-acetylene
1-[trans-4-(trans-4-butylcyclohexyl)cyclohexyl]-2-(4-butylphenyl)-acetylene
1-[trans-4-(trans-4-pentylcyclohexyl)cyclohexyl]-2-(4-butylphenyl)-acetylene
1-[trans-4-(trans-4-hexylcyclohexyl)cyclohexyl]-2-(4-butylphenyl)-acetylene
1-[trans-4-(trans-4-heptylcyclohexyl)cyclohexyl]-2-(4-butylphenyl)-acetylene
1-[trans-4-(trans-4-methylcyclohexyl)cyclohexyl]-2-(4-pentylphenyl)-acetylene
1-[trans-4-(trans-4-ethylcyclohexyl)cyclohexyl]-2-(4-pentylphenyl)-acetylene
1-[trans-4-(trans-4-propylcyclohexyl)cyclohexyl]-2-(4-pentylphenyl)-acetylene
1-[trans-4-(trans-4-butylcyclohexyl)cyclohexyl]-2-(4-pentylphenyl)-acetylene
1-[trans-4-(trans-4-pentylcyclohexyl)cyclohexyl]-2-(4-pentylphenyl)-acetylene
1-[trans-4-(trans-4-hexylcyclohexyl)cyclohexyl]-2-(4-pentylphenyl)-acetylene
1-[trans-4-(trans-4-heptylcyclohexyl)cyclohexyl]-2-(4-pentylphenyl)-acetylene
1-[trans-4-(trans-4-methylcyclohexyl)cyclohexyl]-2-(4-hexylphenyl)-acetylene
1-[trans-4-(trans-4-ethylcyclohexyl)cyclohexyl]-2-(4-hexylphenyl)-acetylene
1-[trans-4-(trans-4-propylcyclohexyl)cyclohexyl]-2-(4-hexylphenyl)-acetylene
1-[trans-4-(trans-4-butylcyclohexyl)cyclohexyl]-2-(4-hexylphenyl)-acetylene
1-[trans-4-(trans-4-pentylcyclohexyl)cyclohexyl]-2-(4-hexylphenyl)-acetylene
1-[trans-4-(trans-4-hexylcyclohexyl)cyclohexyl]-2-(4-hexylphenyl)-acetylene
1-[trans-4-(trans-4-heptylcyclohexyl)cyclohexyl]-2-(4-hexylphenyl)-acetylene
1-[trans-4-(trans-4-methylcyclohexyl)cyclohexyl]-2-(3-fluoro-4-ethylphenyl-acetylene
1-[trans-4-(trans-4-ethylcyclohexyl)cyclohexyl]-2-(3-fluoro-4-ethylphenyl-acetylene
1-[trans-4-(trans-4-propylcyclohexyl)cyclohexyl]-2-(3-fluoro-4-ethylphenyl-acetylene
1-[trans-4-(trans-4-butylcyclohexyl)cyclohexyl]-2-(3-fluoro-4-ethylphenyl)-acetylene
1-[trans-4-(trans-4-pentylcyclohexyl)cyclohexyl]-2-(3-fluoro-4-ethylphenyl)-acetylene
1-[trans-4-(trans-4-hexylcyclohexyl)cyclohexyl]-2-(3-fluoro-4-ethylphenyl)-acetylene
1-[trans-4-(trans-4-heptylcyclohexyl)cyclohexyl]-2-(3-fluoro-4-ethylphenyl)-acetylene
1-[trans-4-(trans-4-methylcyclohexyl)cyclohexyl]-2-(3-fluoro-4-propylphenyl)-acetylene
1-[trans-4-(trans-4-ethylcyclohexyl)cyclohexyl]-2-(3-fluoro-4-propylphenyl)-acetylene
1-[trans-4-(trans-4-propylcyclohexyl)cyclohexyl]-2-(3-fluoro-4-propylphenyl)-acetylene
1-[trans-4-(trans-4-butylcyclohexyl)cyclohexyl]-2-(3-fluoro-4-propylphenyl)-acetylene
1-[trans-4-(trans-4-pentylcyclohexyl)cyclohexyl]-2-(3-fluoro-4-propylphenyl)-acetylene
1-[trans-4-(trans-4-hexylcyclohexyl)cyclohexyl]-2-(3-fluoro-4-propylphenyl)-acetylene
1-[trans-4-(trans-4-heptylcyclohexyl)cyclohexyl]-2-(3-fluoro-4-propylphenyl)-acetylene
1-[trans-4-(trans-4-methylcyclohexyl)cyclohexyl]-2-(3-fluoro-4-butylphenyl)-acetylene
1-[trans-4-(trans-4-ethylcyclohexyl)cyclohexyl]-2-(3-fluoro-4-butylphenyl)-acetylene
1-[trans-4-(trans-4-propylcyclohexyl)cyclohexyl]-2-(3-fluoro-4-butylphenyl)-acetylene
1-[trans-4-(trans-4-butylcyclohexyl)cyclohexyl]-2-(3-fluoro-4-butylphenyl)-acetylene
1-[trans-4-(trans-4-pentylcyclohexyl)cyclohexyl]-2-(3-fluoro-4-butylphenyl)-acetylene
1-[trans-4-(trans-4-hexylcyclohexyl)cyclohexyl]-2-(3-fluoro-4-butylphenyl)-acetylene
1-[trans-4-(trans-4-heptylcyclohexyl)cyclohexyl]-2-(3-fluoro-4-butylphenyl)-acetylene
1-[trans-4-(trans-4-methylcyclohexyl)cyclohexyl]-2-(3-fluoro-4-pentylphenyl)-acetylene
1-[trans-4-(trans-4-ethylcyclohexyl)cyclohexyl]-2-(3-fluoro-4-pentylphenyl)-acetylene
1-[trans-4-(trans-4-propylcyclohexyl)cyclohexyl]-2-(3-fluoro-4-pentylphenyl)-acetylene
1-[trans-4-(trans-4-butylcyclohexyl)cyclohexyl]-2-(3-fluoro-4-pentylphenyl)-acetylene
1-[trans-4-(trans-4-pentylcyclohexyl)cyclohexyl]-2-(3-fluoro-4-pentylphenyl)-acetylene
1-[trans-4-(trans-4-hexylcyclohexyl)cyclohexyl]-2-(3-fluoro-4-pentylphenyl)-acetylene 1-[trans-4-(trans-4-heptylcyclohexyl)cyclohexyl]-2-(3-fluoro-4-pentylphenyl)-acetylene
1-[trans-4-(trans-4-methylcyclohexyl)cyclohexyl]-2-(3-chloro-4-pentylphenyl)-acetylene
1-[trans-4-(trans-4-ethylcyclohexyl)cyclohexyl]-2-(3-chloro-4-pentylphenyl)-acetylene
1-[trans-4-(trans-4-propylcyclohexyl)cyclohexyl]-2-(3-chloro-4-pentylphenyl)-acetylene
1-[trans-4-(trans-4-butylcyclohexyl)cyclohexyl]-2-(3-chloro-4-pentylphenyl)-acetylene
1-[trans-4-(trans-4-pentylcyclohexyl)cyclohexyl]-2-(3-chloro-4-pentylphenyl)-acetylene
1-[trans-4-(trans-4-hexylcyclohexyl)cyclohexyl]-2-(3-chloro-4-pentylphenyl)-acetylene
1-[trans-4-(trans-4-heptylcyclohexyl)cyclohexyl]-2-(3-chloro-4-pentylphenyl)-acetylene
1-[trans-4-(trans-4-methylcyclohexyl)cyclohexyl]-2-(3,4-difluorophenyl)-acetylene
1-[trans-4-(trans-4-ethylcyclohexyl)cyclohexyl]-2-(3,4-difluorophenyl)-acetylene
1-[trans-4-(trans-4-propylcyclohexyl)cyclohexyl]-2-(3,4-difluorophenyl)-acetylene
1-[trans-4-(trans-4-butylcyclohexyl)cyclohexyl]-2-(3,4-difluorophenyl)-acetylene
1-[trans-4-(trans-4-pentylcyclohexyl)cyclohexyl]-2-(3,4-difluorophenyl)-acetylene
1-[trans-4-(trans-4-hexylcyclohexyl)cyclohexyl]-2-(3,4-difluorophenyl)-acetylene
1-[trans-4-(trans-4-heptylcyclohexyl)cyclohexyl]-2-(3,4-difluorophenyl)-acetylene
1-[trans-4-(trans-4-methylcyclohexyl)cyclohexyl]-2-(4-cyanophenyl)-acetylene
1-[trans-4-(trans-4-ethylcyclohexyl)cyclohexyl]-2-(4-cyanophenyl)-acetylene
1-[trans-4-(trans-4-propylcyclohexyl)cyclohexyl]-2-(4-cyanophenyl)-acetylene
1-[trans-4-(trans-4-butylcyclohexyl)cyclohexyl]-2-(4-cyanophenyl)-acetylene
1-[trans-4-(trans-4-pentylcyclohexyl)cyclohexyl]-2-(4-cyanophenyl)-acetylene
1-[trans-4-(trans-4-hexylcyclohexyl)cyclohexyl]-2-(4-cyanophenyl)-acetylene
1-[trans-4-(trans-4-heptylcyclohexyl)cyclohexyl]-2-(4-cyanophenyl)-acetylene
1-[trans-4-(trans-4-methylcyclohexyl)cyclohexyl]-2-(2-fluoro-4-pentylcyclohexyl)-acetylene
1-[trans-4-(trans-4-ethylcyclohexyl)cyclohexyl]-2-(2-fluoro-4-pentylcyclohexyl)-acetylene
1-[trans-4-(trans-4-propylcyclohexyl)cyclohexyl]-2-(2-fluoro-4-pentylcyclohexyl)-acetylene
1-[trans-4-(trans-4-butylcyclohexyl)cyclohexyl]-2-(2-fluoro-4-pentylcyclohexyl)-acetylene
1-[trans-4-(trans-4-pentylcyclohexyl)cyclohexyl]-2-(2-fluoro-4-pentylcyclohexyl)-acetylene
1-[trans-4-(trans-4-hexylcyclohexyl)cyclohexyl]-2-(2-fluoro-4-pentylcyclohexyl)-acetylene
1-[trans-4-(trans-4-heptylcyclohexyl)cyclohexyl]-2-(2-fluoro-4-pentylcyclohexyl)-acetylene
1-[trans-4-(trans-4-methylcyclohexyl)cyclohexyl]-2-(4-propyloxyphenyl)-acetylene
1-[trans-4-(trans-4-ethylcyclohexyl)cyclohexyl]-2-(4-propyloxyphenyl)-acetylene
1-[trans-4-(trans-4-propylcyclohexyl)cyclohexyl]-2-(4-propyloxyphenyl)-acetylene
1-[trans-4-(trans-4-butylcyclohexyl)cyclohexyl]-2-(4-propyloxyphenyl)-acetylene
1-[trans-4-(trans-4-pentylcyclohexyl)cyclohexyl]-2-(4-propyloxyphenyl)-acetylene
1-[trans-4-(trans-4-hexylcyclohexyl)cyclohexyl]-2-(4-propyloxyphenyl)-acetylene
1-[trans-4-(trans-4-heptylcyclohexyl)cyclohexyl]-2-(4-propyloxyphenyl)-acetylene
1-[trans-4-(trans-4-methylcyclohexyl)cyclohexyl]-2-(4-butyloxyphenyl)-acetylene
1-[trans-4-(trans-4-ethylcyclohexyl)cyclohexyl]-2-(4-butyloxyphenyl)-acetylene
1-[trans-4-(trans-4-propylcyclohexyl)cyclohexyl]-2-(4-butyloxyphenyl)-acetylene
1-[trans-4-(trans-4-butylcyclohexyl)cyclohexyl]-2-(4-butyloxyphenyl)-acetylene
1-[trans-4-(trans-4-pentylcyclohexyl)cyclohexyl]-2-(4-butyloxyphenyl)-acetylene
1-[trans-4-(trans-4-hexylcyclohexyl)cyclohexyl]-2-(4-butyloxyphenyl)-acetylene
1-[trans-4-(trans-4-heptylcyclohexyl)cyclohexyl]-2-(4-butyloxyphenyl)-acetylene
1-[trans-4-(trans-4-methylcyclohexyl)cyclohexyl]-2-(4-pentyloxyphenyl)-acetylene
1-[trans-4-(trans-4-ethylcyclohexyl)cyclohexyl]-2-(4-pentyloxyphenyl)-acetylene
1-[trans-4-(trans-4-propylcyclohexyl)cyclohexyl]-2-(4-pentyloxyphenyl)-acetylene
1-[trans-4-(trans-4-butylcyclohexyl)cyclohexyl]-2-(4-pentyloxyphenyl)-acetylene
1-[trans-4-(trans-4-pentylcyclohexyl)cyclohexyl]-2-(4-pentyloxyphenyl)-acetylene
1-[trans-4-(trans-4-hexylcyclohexyl)cyclohexyl]-2-(4-pentyloxyphenyl)-acetylene
1-[trans-4-(trans-4-heptylcyclohexyl)cyclohexyl]-2-(4-pentyloxyphenyl)-acetylene
1-(trans-4-methylcyclohexyl)-2-(4'-propylbiphenyl-4-yl)acetylene
1-(trans-4-ethylcyclohexyl)-2-(4'-propylbiphenyl-4-yl)acetylene
1-(trans-4-propylcyclohexyl)-2-(4'-propylbiphenyl-4-yl)acetylene
1-(trans-4-butylcyclohexyl)-2-(4'-propylbiphenyl-4-yl)-acetylene
1-(trans-4-pentylcyclohexyl)-2-(4'-propylbiphenyl-4-yl)acetylene
1-(trans-4-hexylcyclohexyl)-2-(4'-propylbiphenyl-4-yl)acetylene
1-(trans-4-heptylcyclohexyl)-2-(4'-propylbiphenyl-4-yl)acetylene
1-(trans-4-octylcyclohexyl)-2-(4'-propylbiphenyl-4-yl)acetylene
1-(trans-4-methylcyclohexyl)-2-(4'-butylbiphenyl-4-yl)acetylene
1-(trans-4-ethylcyclohexyl -2-(4'-butylbiphenyl-4-yl)acetylene
1-(trans-4-propylcyclohexyl)-2-(4'-butylbiphenyl-4-yl)acetylene
1-(trans-4-butylcyclohexyl)-2-(4'-butylbiphenyl-4-yl)acetylene
1-(trans-4-pentylcyclohexyl)-2-(4'-butylbiphenyl-4-yl)acetylene
1-(trans-4-hexylcyclohexyl)-2-(4'-butylbiphenyl-4-yl)acetylene
1-(trans-4-heptylcyclohexyl)-2-(4'-butylbiphenyl-4-yl)acetylene
1-(trans-4-methylcyclohexyl)-2-(4'-pentylbiphenyl-4-yl)acetylene
1-(trans-4-ethylcyclohexyl)-2-(4'-pentylbiphenyl-4-yl)acetylene
1-(trans-4-propylcyclohexyl)-2-(4'-pentylbiphenyl-4-yl)acetylene 1-(trans-4-butylcyclohexyl)-2-(4'-pentylbiphenyl-4-yl)-acetylene
1-(trans-4-pentylcyclohexyl)-2-(4'-pentylbiphenyl-4-yl)-acetylene
1-(trans-4-hexylcyclohexyl)-2-(4'-pentylbiphenyl-4-yl)-acetylene
1-(trans-4-heptylcyclohexyl)-2-(4'-pentylbiphenyl-4-yl)-acetylene
1-(trans-4-methylcyclohexyl)-2-(4'-hexylbiphenyl-4-yl)-acetylene
1-(trans-4-ethylcyclohexyl)-2-(4'-hexylbiphenyl-4-yl)-acetylene
1-(trans-4-propylcyclohexyl)-2-(4'-hexylbiphenyl-4-yl)-acetylene
1-(trans-4-butylcyclohexyl)-2-(4'-hexylbiphenyl-4-yl)-acetylene
1-(trans-4-pentylcyclohexyl)-2-(4'-hexylbiphenyl-4-yl)-acetylene
1-(trans-4-hexylcyclohexyl)-2-(4'-hexylbiphenyl-4-yl)-acetylene
1-(trans-4-heptylcyclohexyl)-2-(4'-hexylbiphenyl-4-yl)-acetylene
1-(trans-4-methylcyclohexyl)-2-(4'-heptylbiphenyl-4-yl)-acetylene
1-(trans-4-ethylcyclohexyl)-2-(4'-heptylbiphenyl-4-yl)-acetylene
1-(trans-4-propylcyclohexyl)-2-(4'-heptylbiphenyl-4-yl)-acetylene
1-(trans-4-butylcyclohexyl)-2-(4'-heptylbiphenyl-4-yl)-acetylene
1-(trans-4-pentylcyclohexyl)-2-(4'-heptylbiphenyl-4-yl)-acetylene
1-(trans-4-hexylcyclohexyl)-2-(4'-heptylbiphenyl-4-yl)-acetylene
1-(trans-4-heptylcyclohexyl)-2-(4'-heptylbiphenyl-4-yl)-acetylene
1-(trans-4-methylcyclohexyl)-2-(4'-ethoxybiphenyl-4-yl)-acetylene
1-(trans-4-ethylcyclohexyl)-2(4'-ethoxybiphenyl-4-yl)-acetylene
1-(trans-4-propylcyclohexyl)-2-(4'-ethoxybiphenyl-4-yl)-acetylene
1-(trans-4-butylcyclohexyl)-2-(4'-ethoxybiphenyl-4-yl)-acetylene
1-(trans-4-pentylcyclohexyl)-2-(4'-ethoxybiphenyl-4-yl)-acetylene
1-(trans-4-hexylcyclohexyl)-2-(4'-ethoxybiphenyl-4-yl)-acetylene
1-(trans-4-heptylcyclohexyl)-2-(4'-ethoxybiphenyl-4-yl)-acetylene
1-(trans-4-octylcyclohexyl)-2-(4'-ethoxybiphenyl-4-yl)-acetylene
1-(trans-4-nonylcyclohexyl)-2-(4'-ethoxybiphenyl-4-yl)-acetylene
1-(trans-4-decylcyclohexyl)-2-(4'-ethoxybiphenyl-4-yl)-acetylene
1-(trans-4-methylcyclohexyl)-2-(4'-propyloxybiphenyl-4-yl)-acetylene
1-(trans-4-ethylcyclohexyl)-2-(4'-propyloxybiphenyl-4-yl)-acetylene
1-(trans-4-propylcyclohexyl)-2-(4'-propyloxybiphenyl-4-yl)-acetylene
1-(trans-4-butylcyclohexyl)-2-(4'-propyloxybiphenyl-4-yl)-acetylene
1-(trans-4-pentylcyclohexyl)-2-(4'-propyloxybiphenyl-4-yl)-acetylene
1-(trans-4-hexylcyclohexyl)-2-(4'-propyloxybiphenyl-4-yl)-acetylene
1-(trans-4-heptylcyclohexyl)-2-(4'-propyloxybiphenyl-4-yl)-acetylene
1-(trans-4-octylcyclohexyl)-2-(4'-propyloxybiphenyl-4-yl)-acetylene
1-(trans-4-methylcyclohexyl)-2-(4'-butyloxybiphenyl-4-yl)-acetylene
1-(trans-4-ethylcyclohexyl)-2-(4'-butyloxybiphenyl-4-yl)acetylene
1-(trans-4-propylcyclohexyl)-2-(4'-butyloxybiphenyl-4-yl)-acetylene
1-(trans-4-butylcyclohexyl)-2-(4'-butyloxybiphenyl-4-yl)-acetylene
1-(trans-4-pentylcyclohexyl)-2-(4'-butyloxybiphenyl-4-yl)-acetylene
1-(trans-4-hexylcyclohexyl)-2-(4'-butyloxybiphenyl-4-yl)-acetylene
1-(trans-4-heptylcyclohexyl)-2-(4'-butyloxybiphenyl-4-yl)-acetylene
1-(trans-4-methylcyclohexyl)-2-(4'-pentyloxybiphenyl-4-yl)-acetylene
1-(trans-4-ethylcyclohexyl)-2-(4'-pentyloxybiphenyl-4-yl)-acetylene
1-(trans-4-propylcyclohexyl)-2-(4'-pentyloxybiphenyl-4-yl)-acetylene
1-(trans-4-butylcyclohexyl)-2-(4'-pentyloxybiphenyl-4-yl)-acetylene
1-(trans-4-pentylcyclohexyl)-2-(4'-pentyloxybiphenyl-4-yl)-acetylene
1-(trans-4-hexylcyclohexyl)-2-(4'-pentyloxybiphenyl-4-yl)-acetylene
1-(trans-4-heptylcyclohexyl)-2-(4'-pentyloxybiphenyl-4-yl)-acetylene
1-(trans-4-methylcyclohexyl)-2-(4'-hexyloxybiphenyl-4-yl)-acetylene
1-(trans-4-ethylcyclohexyl)-2-(4'-pentyloxybiphenyl-4-yl)-acetylene
1-(trans-4-propylcyclohexyl)-2-(4'-hexyloxybiphenyl-4-yl)-acetylene
1-(trans-4-butylcyclohexyl)-2-(4'-hexyloxybiphenyl-4-yl)-acetylene
1-(trans-4-pentylcyclohexyl)-2-(4'-hexyloxybiphenyl-4-yl)-acetylene
1-(trans-4-hexylcyclohexyl)-2-(4'-hexyloxybiphenyl-4-yl)-acetylene
1-(trans-4-heptylcyclohexyl)-2-(4'-hexyloxybiphenyl-4-yl)-acetylene
1-(trans-4-methylcyclohexyl)-2-(4'-heptyloxybiphenyl-4-yl)-acetylene
1-(trans-4-ethylcyclohexyl)-2-(4'-heptyloxybiphenyl-4-yl)-acetylene
1-(trans-4-propylcyclohexyl)-2-(4'-heptyloxybiphenyl-4-yl)-acetylene
1-(trans-4-butylcyclohexyl)-2-(4'-heptyloxybiphenyl-4-yl)-acetylene
1-(trans-4-pentylcyclohexyl)-2-(4'-heptyloxybiphenyl-4-yl)-acetylene
1-(trans-4-hexylcyclohexyl)-2-(4'-heptyloxybiphenyl-4-yl)-acetylene
1-(trans-4-methylcyclohexyl)-2-(3'-fluoro-4'-propylbiphenyl-4-yl)-acetylene
1-(trans-4-ethylcyclohexyl)-2-(3'-fluoro-4'-propylbiphenyl-4-yl)-acetylene
1-(trans-4-propylcyclohexyl)-2-(3'-fluoro-4'-propylbiphenyl-4-yl)-acetylene
1-(trans-4-butylcyclohexyl)-2-(3'-fluoro-4'-propylbiphenyl-4-yl)-acetylene
1-(trans-4-pentylcyclohexyl)-2-(3'-fluoro-4'-propylbiphenyl-4-yl)-acetylene 1-(trans-4-hexylcyclohexyl)-2-(3'-fluoro-4'-propylbiphenyl-4-yl)-acetylene
1-(trans-4-heptylcyclohexyl)-2-(3'-fluoro-4'-propylbiphenyl-4-yl)-acetylene
1-(trans-4-methylcyclohexyl)-2-(3'-fluoro-4'-butylbiphenyl-4-yl)-acetylene
1-(trans-4-ethylcyclohexyl)-2-(3'-fluoro-4'-butylbi-phenyl-4-yl)-acetylene
1-(trans-4-propylcyclohexyl)-2-(3'-fluoro-4'-butylbiphenyl-4-yl)-acetylene
1-(trans-4-butylcyclohexyl)-2-(3'-fluoro-4'-butylbi-phenyl-4-yl)-acetylene
1-(trans-4-pentylcyclohexyl)-2-(3'-fluoro-4'-butylbiphenyl-4-yl)-acetylene
1-(trans-4-hexylcyclohexyl)-2-(3'-fluoro-4'-butylbi-phenyl-4-yl)-acetylene
1-(trans-4-heptylcyclohexyl)-2-(3'-fluoro-4'-butylbiphenyl-4-yl)-acetylene
1-(trans-4-octylcyclohexyl)-2-(3'-fluoro-4'-butylbiphenyl-4-yl)-acetylene
1-(trans-4-methylcyclohexyl)-2-(3'-fluoro-4'-pentylbiphenyl-4-yl)-acetylene
1-(trans-4-ethylcyclohexyl)-2-(3'-fluoro-4'-pentylbiphenyl-4-yl)-acetylene
1-(trans-4-propylcyclohexyl)-2-(3'-fluoro-4'-pentylbiphenyl-4-yl)-acetylene
1-(trans-4-butylcyclohexyl)-2-(3'-fluoro-4'-pentylbiphenyl-4-yl)-acetylene
1-(trans-4-pentylcyclohexyl)-2-(3'-fluoro-4'-pentylbiphenyl-4-yl)-acetylene
1-(trans-4-hexylcyclohexyl)-2-(3'-fluoro-4'-pentylbiphenyl-4-yl)-acetylene
1-(trans-4-heptylcyclohexyl)-2-(3'-fluoro-4'-pentylbiphenyl-4-yl)-acetylene
1-(trans-4-methylcyclohexyl)-2-(3'-fluoro-4'-butylbiphenyl-4-yl)-acetylene
1-(trans-4-ethylcyclohexyl)-2-(3'-fluoro-4'-butylbiphenyl-4-yl)-acetylene
1-(trans-4-propylcyclohexyl)-2-(3'-fluoro-4'-butylbiphenyl-4-yl)-acetylene
1-(trans-4-butylcyclohexyl)-2-(3'-fluoro-4'-butylbiphenyl-4-yl)-acetylene
1-(trans-4-pentylcyclohexyl)-2-(3'-fluoro-4'-butylbiphenyl-4-yl)-acetylene
1-(trans-4-hexylcyclohexyl)-2-(3'-fluoro-4'-butylbiphenyl-4-yl)-acetylene
1-(trans-4-heptylcyclohexyl)-2-(3'-fluoro-4'-butylbiphenyl-4-yl)-acetylene
1-(trans-4-octylcyclohexyl)-2-(3'-fluoro-4'-butylbiphenyl-4-yl)-acetylene
1-(trans-4-methylcyclohexyl)-2-(2-chloro-4'-pentylbiphenyl-4-yl)-acetylene
1-(trans-4-ethylcyclohexyl)-2-(2-chloro-4'-pentylbiphenyl-4-yl)-acetylene
1-(trans-4-propylcyclohexyl)-2-(2-chloro-4'-pentylbiphenyl-4-yl)-acetylene
1-(trans-4-butylcyclohexyl)-2-(2-chloro-4'-pentylbiphenyl-4-yl)-acetylene
1-(trans-4-pentylcyclohexyl)-2-(2-chloro-4'-pentylbiphenyl-4-yl)-acetylene
1-(trans-4-hexylcyclohexyl)-2-(2-chloro-4'-pentylbiphenyl-4-yl)-acetylene
1-(trans-4-heptylcyclohexyl)-2-(2-chloro-4'-pentylbiphenyl-4-yl)-acetylene
1-(trans-4-methylcyclohexyl)-2-(4'-cyanobiphenyl-4-yl)acetylene
1-(trans-4-ethylcyclohexyl)-2-(4'-cyanobiphenyl-4-yl)acetylene
1-(trans-4-propylcyclohexyl)-2-(4'-cyanobiphenyl-4-yl)acetylene
1-(trans-4-butylcyclohexyl)-2-(4'-cyanobiphenyl-4-yl)acetylene
1-(trans-4-pentylcyclohexyl)-2-(4'-cyanobiphenyl-4-yl)acetylene
1-(trans-4-hexylcyclohexyl)-2-(4'-cyanobiphenyl-4-yl)acetylene
1-(trans-4-heptylcyclohexyl)-2-(4'-cyanobiphenyl-4-yl)acetylene
1-(trans-4-octylcyclohexyl)-2-(4'-cyanobiphenyl-4-yl)acetylene
1-(trans-4-nonylcyclohexyl)-2-(4'-cyanobiphenyl-4-yl)acetylene
1-(trans-4-decylcyclohexyl)-2-(4'-cyanobiphenyl-4-yl)acetylene.

EXAMPLE 2

0.2 m of 4-propylbenzaldehyde and 0.2 mol of 2-methyl-5-methylpyridine are heated at 200° together with 3 g of zinc chloride for 2 days. The course of the reaction can be monitored with the aid of thin layer chromatography. When the reaction has ended, excess starting material is distilled off and the residue is purified by crystallization or chromatography.

0.1 mol of the stilbene derivative thus obtained is brominated in 200 ml of glacial acetic acid with 0.1 mol of $Br_2$ at room temperature, with stirring. When the addition has ended, the mixture is heated briefly at the boiling point. The glacial acetic acid is then evaporated off and 200 ml of tert.-butanol are added to the residue. 0.4 mol of potassium tert.-butanolate are added to this mixture at room temperature and the mixture is subsequently heated at the boiling point for 3 hours. After cooling, water is added and the mixture is extracted with ether. Working up of the organic phase and purification by chromatography gives 1-(4-propylphenyl)2-(5-methyl-pyridin-2-yl)-acetylene of M.=76°, C.=−20° (extr. and $\Delta\epsilon$ =−1.2.

The following compounds are prepared analogously:
1-(4-propylphenyl)-2-(5-ethyl-pyridin-2-yl)-acetylene
1-(4-propylphenyl)-2-(5-propyl-pyridin-2-yl)-acetylene
1-(4-propylphenyl)-2-(5-butyl-pyridin-2-yl)-acetylene
1-(4-propylphenyl)-2-(5-pentyl-pyridin-2-yl)-acetylene
1-(4-propylphenyl)-2-(5-hexyl-pyridin-2-yl)-acetylene
1-(4-propylphenyl)-2-(5-heptyl-pyridin-2-yl)-acetylene
1-(4-propylphenyl)-2-(4-octyl-pyridin-2-yl)-acetylene
1-(4-ethylphenyl)-2-(4-methyl-pyridin-2-yl)-acetylene
1-(4-ethylphenyl)-2-(5-ethyl-pyridin-2-yl)-acetylene
1-(4-ethylphenyl)-2-(4-propyl-pyridin-2-yl)-acetylene
1-(4-ethylphenyl)-2-(5-butyl-pyridin-2-yl)-acetylene
1-(4-ethylphenyl)-2-(5-pentyl-pyridin-2-yl)-acetylene
1-(4-ethylphenyl)-2-(5-hexyl-pyridin-2-yl)-acetylene
1-(4-ethylphenyl)-2-(5-heptyl-pyridin-2-yl)-acetylene
1-(4-ethylphenyl)-2-(5-octyl-pyridin-2-yl)-acetylene
1-(4-butylphenyl)-2-(5-methyl-pyridin-2-yl)-acetylene
1-(4-butylphenyl)-2-(5-ethyl-pyridin-2-yl)-acetylene
1-(4-butylphenyl)-2-(5-propyl-pyridin-2-yl)-acetylene
1-(4-butylphenyl)-2-(5-butyl-pyridin-2-yl)-acetylene
1-(4-butylphenyl)-2-(5-pentyl-pyridin-2-yl)-acetylene
1-(4-butylphenyl)-2-(5-hexyl-pyridin-2-yl)-acetylene
1-(4-butylphenyl)-2-(5-heptyl-pyridin-2-yl)-acetylene
1-(4-butylphenyl)-2-(5-octyl-pyridin-2-yl)-acetylene
1-(4-pentylphenyl)-2-(5-methyl-pyridin-2-yl)-acetylene
1-(4-pentylphenyl)-2-(5-ethyl-pyridin-2-yl)-acetylene
1-(4-pentylphenyl)-2-(5-propyl-pyridin-2-yl)-acetylene
1-(4-pentylphenyl)-2-(5-butyl-pyridin-2-yl)-acetylene
1-(4-pentylphenyl)-2-(5-pentyl-pyridin-2-yl)-acetylene 1-(4-pentylphenyl)-2-(5-hexyl-pyridin-2-yl)-acetylene
1-(4-pentylphenyl)-2-(5-heptyl-pyridin-2-yl)-acetylene
1-(4-pentylphenyl)-2-(5-octyl-pyridin-2-yl)-acetylene
1-(4-hexylphenyl)-2-(5-methyl-pyridin-2-yl)-acetylene
1-(4-hexylphenyl)-2-(5-ethyl-pyridin-2-yl)-acetylene
1-(4-hexylphenyl)-2-(5-propyl-pyridin-2-yl)-acetylene
1-(4-hexylphenyl)-2-(5-butyl-pyridin-2-yl)-acetylene
1-(4-hexylphenyl)-2-(5-pentyl-pyridin-2-yl)-acetylene
1-(4-hexylphenyl)-2-(5-hexyl-pyridin-2-yl)-acetylene
1-(4-hexylphenyl)-2-(5-heptyl-pyridin-2-yl)-acetylene
1-(4-hexylphenyl)-2-(5-octyl-pyridin-2-yl)-acetylene
1-(4-heptylphenyl)-2-(5-methyl-pyridin-2-yl)-acetylene
1-(4-heptylphenyl)-2-(5-ethyl-pyridin-2-yl)-acetylene
1-(4-heptylphenyl)-2-(5-propyl-pyridin-2-yl)-acetylene
1-(4-heptylphenyl)-2-(5-butyl-pyridin-2-yl)-acetylene
1-(4-heptylphenyl)-2-(5-pentyl-pyridin-2-yl)-acetylene
1-(4-heptylphenyl)-2-(5-hexyl-pyridin-2-yl)-acetylene
1-(4-heptylphenyl)-2-(5-heptyl-pyridin-2-yl)-acetylene
1-(4-heptylphenyl)-2-(5-octyl-pyridin-2-yl)-acetylene
1-(4-octylphenyl)-2-(5-methyl-pyridin-2-yl)-acetylene
1-(4-octylphenyl)-2-(5-ethyl-pyridin-2-yl)-acetylene
1-(4-octylphenyl)-2-(5-propyl-pyridin-2-yl)-acetylene
1-(4-octylphenyl)-2-(5-butyl-pyridin-2-yl)-acetylene
1-(4-octylphenyl)-2-(5-pentyl-pyridin-2-yl)-acetylene
1-(4-octylphenyl)-2-(5-hexyl-pyridin-2-yl)-acetylene
1-(4-octylphenyl)-2-(5-heptyl-pyridin-2-yl)-acetylene
1-(4-octylphenyl)-2-(5-octyl-pyridin-2-yl)-acetylene
1-(4-ethylphenyl)-2-(5-methyloxy-pyridin-2-yl)-acetylene
1-(4-ethylphenyl)-2-(5-ethyloxy-pyridin-2-yl)-acetylene
1-(4-ethylphenyl)-2-(5-propyloxy-pyridin-2-yl)-acetylene
1-(4-ethylphenyl)-2-(5-butyloxy-pyridin-2-yl)-acetylene
1-(4-ethylphenyl)-2-(5-pentyloxy-pyridin-2-yl)-acetylene
1-(4-ethylphenyl)-2-(5-hexyloxy-pyridin-2-yl)-acetylene
1-(4-ethylphenyl)-2-(5-heptyloxy-pyridin-2-yl)-acetylene
1-(4-ethylphenyl)-2-(5-octyloxy-pyridin-2-yl)-acetylene
1-(4-propylphenyl)-2-(5-methyloxy-pyridin-2-yl)-acetylene
1-(4-propylphenyl)-2-(5-ethyloxy-pyridin-2-yl)-acetylene
1-(4-propylphenyl)-2-(5-propyloxy-pyridin-2-yl)-acetylene
1-(4-propylphenyl)-2-(5-butyloxy-pyridin-2-yl)-acetylene
1-(4-propylphenyl)-2-(5-pentyloxy-pyridin-2-yl)-acetylene
1-(4-propylphenyl)-2-(5-hexyloxy-pyridin-2-yl)-acetylene
1-(4-propylphenyl)-2-(5-heptyloxy-pyridin-2-yl)-acetylene
1-(4-propylphenyl)-2-(5-octyl-pyridin-2-yl)-acetylene
1-(4-butylphenyl)-2-(5-methyloxy-pyridin-2-yl)-acetylene
1-(4-butylphenyl)-2-(5-ethyloxy-pyridin-2-yl)-acetylene
1-(4-butylphenyl)-2-(5-propyloxy-pyridin-2-yl)-acetylene
1-(4-butylphenyl)-2-(5-butyloxy-pyridin-2-yl)-acetylene
1-(4-butylphenyl)-2-(5-pentyloxy-pyridin-2-yl)-acetylene
1-(4-butylphenyl)-2-(5-hexyloxy-pyridin-2-yl)-acetylene
1-(4-butylphenyl)-2-(5-heptyloxy-pyridin-2-yl)-acetylene
1-(4-butylphenyl)-2-(5-octyloxy-pyridin-2-yl)-acetylene
1-(4-pentylphenyl)-2-(5-methyloxy-pyridin-2-yl)-acetylene
1-(4-pentylphenyl)-2-(5-ethyloxy-pyridin-2-yl)-acetylene
1-(4-pentylphenyl)-2-(5-propyloxy-pyridin-2-yl)-acetylene
1-(4-pentylphenyl)-2-(5-butyloxy-pyridin-2-yl)-acetylene
1-(4-pentylphenyl)-2-(5-pentyloxy-pyridin-2-yl)-acetylene
1-(4-pentylphenyl)-2-(5-hexyloxy-pyridin-2-yl)-acetylene
1-(4-pentylphenyl)-2-(5-heptyloxy-pyridin-2-yl)-acetylene
1-(4-pentylphenyl)-2-(5-octyloxy-pyridin-2-yl)-acetylene
1-(4-hexylphenyl)-2-(5-methyloxy-pyridin-2-yl)-acetylene
1-(4-hexylphenyl)-2-(5-ethyloxy-pyridin-2-yl)-acetylene
1-(4-hexylphenyl)-2-(5-propyloxy-pyridin-2-yl)-acetylene
1-(4-hexylphenyl)-2-(5-butyloxy-pyridin-2-yl)-acetylene
1-(4-hexylphenyl)-2-(5-pentyloxy-pyridin-2-yl)-acetylene
1-(4-hexylphenyl)-2-(5-hexyloxy-pyridin-2-yl)-acetylene
1-(4-hexylphenyl)-2-(5-heptyloxy-pyridin-2-yl)-acetylene
1-(4-hexylphenyl)-2-(5-octyloxy-pyridin-2-yl)-acetylene
1-(4-heptylphenyl)-2-(5-methyloxy-pyridin-2-yl)-acetylene
1-(4-heptylphenyl)-2-(5-ethyloxy-pyridin-2-yl)-acetylene
1-(4-heptylphenyl)-2-(5-propyloxy-pyridin-2-yl)-acetylene
1-(4-heptylphenyl)-2-(5-butyloxy-pyridin-2-yl)-acetylene
1-(4-heptylphenyl)-2-(5-pentyloxy-pyridin-2-yl)-acetylene
1-(4-heptylphenyl)-2-(5-hexyloxy-pyridin-2-yl)-acetylene
1-(4-heptylphenyl)-2-(5-heptyloxy-pyridin-2-yl)-acetylene
1-(4-heptylphenyl)-2-(5-octyloxy-pyridin-2-yl)-acetylene
1-(4-octylphenyl)-2-(5-methyloxy-pyridin-2-yl)-acetylene
1-(4-octylphenyl)-2-(5-ethyloxy-pyridin-2-yl)-acetylene
1-(4-octylphenyl)-2-(5-propyloxy-pyridin-2-yl)-acetylene
1-(4-octylphenyl)-2-(5-butyloxy-pyridin-2-yl)-acetylene
1-(4-octylphenyl)-2-(5-pentyloxy-pyridin-2-yl)-acetylene
1-(4-octylphenyl)-2-(5-hexyloxy-pyridin-2-yl)-acetylene
1-(4-octylphenyl)-2-(5-heptyloxy-pyridin-2-yl)-acetylene
1-(4-octylphenyl)-2-(5-octyloxy-pyridin-2-yl)-acetylene
1-(4-ethyloxyphenyl)-2-(5-methyl-pyridin-2-yl)-acetylene
1-(4-ethyloxyphenyl)-2-(5-ethyl-pyridin-2-yl)-acetylene
1-(4-ethyloxyphenyl)-2-(5-propyl-pyridin-2-yl)-acetylene
1-(4-ethyloxyphenyl)-2-(5-butyl-pyridin-2-yl)-acetylene
1-(4-ethyloxyphenyl)-2-(5-pentyl-pyridin-2-yl)-acetylene
1-(4-ethyloxyphenyl)-2-(5-hexyl-pyridin-2-yl)-acetylene 1-(4-ethyloxyphenyl)-2-(5-heptyl-pyridin-2-yl)-acetylene
1-(4-ethyloxyphenyl)-2-(5-octyl-pyridin-2-yl)-acetylene
1-(4-propyloxyphenyl)-2-(5-methyl-pyridin-2-yl)-acetylene
1-(4-propyloxyphenyl)-2-(5-ethyl-pyridin-2-yl)-acetylene
1-(4-propyloxyphenyl)-2-(5-propyl-pyridin-2-yl)-acetylene
1-(4-propyloxyphenyl)-2-(5-butyl-pyridin-2-yl)-acetylene
1-(4-propyloxyphenyl)-2-(5-pentyl-pyridin-2-yl)-acetylene
1-(4-propyloxyphenyl)-2-(5-hexyl-pyridin-2-yl)-acetylene
1-(4-propyloxyphenyl)-2-(5-heptyl-pyridin-2-yl)-acetylene
1-(4-propyloxyphenyl)-2-(5-octyl-pyridin-2-yl)-acetylene
1-(4-butyloxyphenyl)-2-(5-methyl-pyridin-2-yl)-acetylene
1-(4-butyloxyphenyl)-2-(5-ethyl-pyridin-2-yl)-acetylene
1-(4-butyloxyphenyl)-2-(5-propyl-pyridin-2-yl)-acetylene
1-(4-butyloxyphenyl)-2-(5-butyl-pyridin-2-yl)-acetylene
1-(4-butyloxyphenyl)-2-(5-pentyl-pyridin-2-yl)-acetylene
1-(4-butyloxyphenyl)-2-(5-hexyl-pyridin-2-yl)-acetylene
1-(4-butyloxyphenyl)-2-(5-heptyl-pyridin-2-yl)-acetylene
1-(4-butyloxyphenyl)-2-(5-octyl-pyridin-2-yl)-acetylene
1-(4-pentyloxyphenyl)-2-(5-methyl-pyridin-2-yl)-acetylene
1-(4-pentyloxyphenyl)-2-(5-ethyl-pyridin-2-yl)-acetylene
1-(4-pentyloxyphenyl)-2-(5-propyl-pyridin-2-yl)-acetylene
1-(4-pentyloxyphenyl)-2-(5-butyl-pyridin-2-yl)-acetylene
1-(4-pentyloxyphenyl)-2-(5-pentyl-pyridin-2-yl)-acetylene
1-(4-pentyloxyphenyl)-2-(5-hexyl-pyridin-2-yl)-acetylene
1-(4-pentyloxyphenyl)-2-(5-heptyl-pyridin-2-yl)-acetylene
1-(4-pentyloxyphenyl)-2-(5-octyl-pyridin-2-yl)-acetylene
1-(4-hexyloxyphenyl)-2-(5-methyl-pyridin-2-yl)-acetylene
1-(4-hexyloxyphenyl)-2-(5-ethyl-pyridin-2-yl)-acetylene
1-(4-hexyloxyphenyl)-2-(5-propyl-pyridin-2-yl)-acetylene
1-(4-hexyloxyphenyl)-2-(5-butyl-pyridin-2-yl)-acetylene
1-(4-hexyloxyphenyl)-2-(5-pentyl-pyridin-2-yl)-acetylene
1-(4-hexyloxyphenyl)-2-(5-hexyl-pyridin-2-yl)-acetylene
1-(4-hexyloxyphenyl)-2-(5-heptyl-pyridin-2-yl)-acetylene
1-(4-hexyloxyphenyl)-2-(5-octyl-pyridin-2-yl)-acetylene
1-(4-heptyloxyphenyl)-2-(5-methyl-pyridin-2-yl)-acetylene
1-(4-heptyloxyphenyl)-2-(5-ethyl-pyridin-2-yl)-acetylene
1-(4-heptyloxyphenyl)-2-(5-propyl-pyridin-2-yl)-acetylene
1-(4-heptyloxyphenyl)-2-(5-butyl-pyridin-2-yl)-acetylene
1-(4-heptyloxyphenyl)-2-(5-pentyl-pyridin-2-yl)-acetylene
1-(4-heptyloxyphenyl)-2-(5-hexyl-pyridin-2-yl)-acetylene
1-(4-heptyloxyphenyl)-2-(5-heptyl-pyridin-2-yl)-acetylene
1-(4-heptyloxyphenyl)-2-(5-octyl-pyridin-2-yl)-acetylene
1-(4-octyloxyphenyl)-2-(5-methyl-pyridin-2-yl)-acetylene
1-(4-octyloxyphenyl)-2-(5-ethyl-pyridin-2-yl)-acetylene
1-(4-octyloxyphenyl)-2-(5-propyl-pyridin-2-yl)-acetylene
1-(4-octyloxyphenyl)-2-(5-butyl-pyridin-2-yl)-acetylene
1-(4-octyloxyphenyl)-2-(5-pentyl-pyridin-2-yl)-acetylene
1-(4-octyloxyphenyl)-2-(5-hexyl-pyridin-2-yl)-acetylene
1-(4-octyloxyphenyl)-2-(5-heptyl-pyridin-2-yl)-acetylene
1-(4-octyloxyphenyl)-2-(5-octyl-pyridin-2-yl)-acetylene
1-(4-propylphenyl)-2-(5-methyl-pyrimidin-2-yl)-acetylene
1-(4-propylphenyl)-2-(5-ethyl-pyrimidin-2-yl)-acetylene
1-(4-propylphenyl)-2-(5-propyl-pyrimidin-2-yl)-acetylene
1-(4-propylphenyl)-2-(5-butyl-pyrimidin-2-yl)-acetylene
1-(4-propylphenyl)-2-(5-pentyl-pyrimidin-2-yl)-acetylene
1-(4-propylphenyl)-2-(5-hexyl-pyrimidin-2-yl)-acetylene
1-(4-propylphenyl)-2-(5-heptyl-pyrimidin-2-yl)-acetylene
1-(4-propylphenyl)-2-(5-octyl-pyrimidin-2-yl)-acetylene
1-(4-butylphenyl)-2-(5-methyl-pyrimidin-2-yl)-acetylene
1-(4-butylphenyl)-2-(5-ethyl-pyrimidin-2-yl)-acetylene
1-(4-butylphenyl)-2-(5-propyl-pyrimidin-2-yl)-acetylene
1-(4-butylphenyl)-2-(5-butyl-pyrimidin-2-yl)-acetylene
1-(4-butylphenyl)-2-(5-pentyl-pyrimidin-2-yl)-acetylene
1-(4-butylphenyl)-2-(5-hexyl-pyrimidin-2-yl)-acetylene
1-(4-butylphenyl)-2-(5-heptyl-pyrimidin-2-yl)-acetylene
1-(4-butylphenyl)-2-(5-octyl-pyrimidin-2-yl)-acetylene
1-(4-pentylphenyl)-2-(5-methyl-pyrimidin-2-yl)-acetylene
1-(4-pentylphenyl)-2-(5-ethyl-pyrimidin-2-yl)-acetylene
1-(4-pentylphenyl)-2-(5-propyl-pyrimidin-2-yl)-acetylene
1-(4-pentylphenyl)-2-(5-butyl-pyrimidin-2-yl)-acetylene
1-(4-pentylphenyl)-2-(5-pentyl-pyrimidin-2-yl)-acetylene
1-(4-pentylphenyl)-2-(5-hexyl-pyrimidin-2-yl)-acetylene
1-(4-pentylphenyl)-2-(5-heptyl-pyrimidin-2-yl)-acetylene
1-(4-pentylphenyl)-2-(5-octyl-pyrimidin-2-yl)-acetylene
1-(4-hexylphenyl)-2-(5-methyl-pyrimidin-2-yl)-acetylene
1-(4-hexylphenyl)-2-(5-ethyl-pyrimidin-2-yl)-acetylene
1-(4-hexylphenyl)-2-(5-propyl-pyrimidin-2-yl)-acetylene
1-(4-hexylphenyl)-2-(5-butyl-pyrimidin-2-yl)-acetylene
1-(4-hexylphenyl)-2-(5-pentyl-pyrimidin-2-yl)-acetylene
1-(4-hexylphenyl)-2-(5-hexyl-pyrimidin-2-yl)-acetylene
1-(4-hexylphenyl)-2-(5-heptyl-pyrimidin-2-yl)-acetylene 1-(4-hexylphenyl)-2-(5-octyl-pyrimidin-2-yl)-acetylene
1-(4-propyloxyphenyl)-2-(5-methyl-pyrimidin-2-yl)-acetylene
1-(4-propyloxyphenyl)-2-(5-ethyl-pyrimidin-2-yl)-acetylene
1-(4-propyloxyphenyl)-2-(5-propyl-pyrimidin-2-yl)-acetylene
1-(4-propyloxyphenyl)-2-(5-butyl-pyrimidin-2-yl)-acetylene
1-(4-propyloxyphenyl)-2-(5-pentyl-pyrimidin-2-yl)-acetylene
1-(4-propyloxyphenyl)-2-(5-hexyl-pyrimidin-2-yl)-acetylene
1-(4-propyloxyphenyl)-2-(5-heptyl-pyrimidin-2-yl)-acetylene
1-(4-propyloxyphenyl)-2-(5-octyl-pyrimidin-2-yl)-acetylene
1-(4-butyloxyphenyl)-2-(5-methyl-pyrimidin-2-yl)-acetylene
1-(4-butyloxyphenyl)-2-(5-ethyl-pyrimidin-2-yl)-acetylene
1-(4-butyloxyphenyl)-2-(5-propyl-pyrimidin-2-yl)-acetylene
1-(4-butyloxyphenyl)-2-(5-butyl-pyrimidin-2-yl)-acetylene
1-(4-butyloxyphenyl)-2-(5-pentyl-pyrimidin-2-yl)-acetylene
1-(4-butyloxyphenyl)-2-(5-hexyl-pyrimidin-2-yl)-acetylene
1-(4-butyloxyphenyl)-2-(5-heptyl-pyrimidin-2-yl)-acetylene
1-(4-butyloxyphenyl)-2-(5-octyl-pyrimidin-2-yl)-acetylene
1-(4-pentyloxyphenyl)-2-(5-methyl-pyrimidin-2-yl)-acetylene
1-(4-pentyloxyphenyl)-2-(5-ethyl-pyrimidin-2-yl)-acetylene
1-(4-pentyloxyphenyl)-2-(5-propyl-pyrimidin-2-yl)-acetylene
1-(4-pentyloxyphenyl)-2-(5-butyl-pyrimidin-2-yl)-acetylene
1-(4-pentyloxyphenyl)-2-(5-pentyl-pyrimidin-2-yl)-acetylene
1-(4-pentyloxyphenyl)-2-(5-hexyl-pyrimidin-2-yl)-acetylene
1-(4-pentyloxyphenyl)-2-(5-heptyl-pyrimidin-2-yl)-acetylene
1-(4-pentyloxyphenyl)-2-(5-octyl-pyrimidin-2-yl)-acetylene
1-(4-propylphenyl)-2-(5-methyloxy-pyrimidin-2-yl)-acetylene
1-(4-propylphenyl)-2-(5-ethyloxy-pyrimidin-2-yl)-acetylene
1-(4-propylphenyl)-2-(5-propyloxy-pyrimidin-2-yl)-acetylene
1-(4-propylphenyl)-2-(5-butyloxy-pyrimidin-2-yl)-acetylene
1-(4-propylphenyl)-2-(5-pentyloxy-pyrimidin-2-yl)-acetylene
1-(4-propylphenyl)-2-(5-hexyloxy-pyrimidin-2-yl)-acetylene
1-(4-propylphenyl)-2-(5-heptyloxy-pyrimidin-2-yl)-acetylene
1-(4-propylphenyl)-2-(5-octyloxy-pyrimidin-2-yl)-acetylene
1-(4-butylphenyl)-2-(5-methyloxy-pyrimidin-2-yl)-acetylene
1-(4-butylphenyl)-2-(5-ethyloxy-pyrimidin-2-yl)-acetylene
1-(4-butylphenyl)-2-(5-propyloxy-pyrimidin-2-yl)-acetylene
1-(4-butylphenyl)-2-(5-butyloxy-pyrimidin-2-yl)-acetylene
1-(4-butylphenyl)-2-(5-pentyloxy-pyrimidin-2-yl)-acetylene
1-(4-butylphenyl)-2-(5-hexyloxy-pyrimidin-2-yl)-acetylene
1-(4-butylphenyl)-2-(5-heptyloxy-pyrimidin-2-yl)-acetylene
1-(4-butylphenyl)-2-(5-octyloxy-pyrimidin-2-yl)-acetylene
1-(4-pentylphenyl)-2-(5-methyloxy-pyrimidin-2-yl)-acetylene
1-(4-pentylphenyl)-2-(5-ethyloxy-pyrimidin-2-yl)-acetylene
1-(4-pentylphenyl)-2-(5-propyloxy-pyrimidin-2-yl)-acetylene
1-(4-pentylphenyl)-2-(5-butyloxy-pyrimidin-2-yl)-acetylene
1-(4-pentylphenyl)-2-(5-pentyloxy-pyrimidin-2-yl)-acetylene
1-(4-pentylphenyl)-2-(5-hexyloxy-pyrimidin-2-yl)-acetylene
1-(4-pentylphenyl)-2-(5-heptyloxy-pyrimidin-2-yl)-acetylene
1-(4-pentylphenyl)-2-(5-octyloxy-pyrimidin-2-yl)-acetylene
1-(4-hexylphenyl)-2-(5-methyloxy-pyrimidin-2-yl)-acetylene
1-(4-hexylphenyl)-2-(5-ethyloxy-pyrimidin-2-yl)-acetylene
1-(4-hexylphenyl)-2-(5-propyloxy-pyrimidin-2-yl)-acetylene
1-(4-hexylphenyl)-2-(5-butyloxy-pyrimidin-2-yl)-acetylene
1-(4-hexylphenyl)-2-(5-pentyloxy-pyrimidin-2-yl)-acetylene
1-(4-hexylphenyl)-2-(5-hexyloxy-pyrimidin-2-yl)-acetylene
1-(4-hexylphenyl)-2-(5-heptyloxy-pyrimidin-2-yl)-acetylene
1-(4-hexylphenyl)-2-(5-octyloxy-pyrimidin-2-yl)-acetylene
1-(4-propylphenyl)-2-(6-methyl-pyridazin-3-yl)-acetylene
1-(4-propylphenyl)-2-(6-ethyl-pyridazin-3-yl)-acetylene
1-(4-propylphenyl)-2-(6-propyl-pyridazin-3-yl)-acetylene
1-(4-propylphenyl)-2-(6-butyl-pyridazin-3-yl)-acetylene
1-(4-propylphenyl)-2-(6-pentyl-pyridazin-3-yl)-acetylene
1-(4-propylphenyl)-2-(6-hexyl-pyridazin-3-yl)-acetylene
1-(4-propylphenyl)-2-(6-heptyl-pyridazin-3-yl)-acetylene
1-(4-propylphenyl)-2-(6-octyl-pyridazin-3-yl)-acetylene
1-(4-butylphenyl)-2-(6-methyl-pyridazin-3-yl)-acetylene
1-(4-butylphenyl)-2-(6-ethyl-pyridazin-3-yl)-acetylene
1-(4-butylphenyl)-2-(6-propyl-pyridazin-3-yl)-acetylene
1-(4-butylphenyl)-2-(6-butyl-pyridazin-3-yl)-acetylene
1-(4-butylphenyl)-2-(6-pentyl-pyridazin-3-yl)-acetylene
1-(4-butylphenyl)-2-(6-hexyl-pyridazin-3-yl)-acetylene
1-(4-butylphenyl)-2-(6-heptyl-pyridazin-3-yl)-acetylene
1-(4-butylphenyl)-2-(6-octyl-pyridazin-3-yl)-acetylene
1-(4-pentylphenyl)-2-(6-methyl-pyridazin-3-yl)-acetylene 1-(4-pentylphenyl)-2-(6-ethyl-pyridazin-3-yl)-acetylene
1-(4-pentylphenyl)-2-(6-propyl-pyridazin-3-yl)-acetylene
1-(4-pentylphenyl)-2-(6-butyl-pyridazin-3-yl)-acetylene
1-(4-pentylphenyl)-2-(6-pentyl-pyridazin-3-yl)-acetylene
1-(4-pentylphenyl)-2-(6-hexyl-pyridazin-3-yl)-acetylene
1-(4-pentylphenyl)-2-(6-heptyl-pyridazin-3-yl)-acetylene
1-(4-pentylphenyl)-2-(6-octyl-pyridazin-3-yl)-acetylene
1-(4-hexylphenyl)-2-(6-methyl-pyridazin-3-yl)-acetylene
1-(4-hexylphenyl)-2-(6-ethyl-pyridazin-3-yl)-acetylene
1-(4-hexylphenyl)-2-(6-propyl-pyridazin-3-yl)-acetylene
1-(4-hexylphenyl)-2-(6-butyl-pyridazin-3-yl)-acetylene
1-(4-hexylphenyl)-2-(6-pentyl-pyridazin-3-yl)-acetylene
1-(4-hexylphenyl)-2-(6-hexyl-pyridazin-3-yl)-acetylene
1-(4-hexylphenyl)-2-(6-heptyl-pyridazin-3-yl)-acetylene
1-(4-hexylphenyl)-2-(6-octyl-pyridazin-3-yl)-acetylene
1-(4-ethoxyphenyl)-2-(6-methyl-pyridazin-3-yl)-acetylene
1-(4-ethoxyphenyl)-2-(6-ethyl-pyridazin-3-yl)-acetylene
1-(4-ethoxyphenyl)-2-(6-propyl-pyridazin-3-yl)-acetylene
1-(4-ethoxyphenyl)-2-(6-butyl-pyridazin-3-yl)-acetylene
1-(4-ethoxyphenyl)-2-(6-pentyl-pyridazin-3-yl)-acetylene
1-(4-ethoxyphenyl)-2-(6-hexyl-pyridazin-3-yl)-acetylene
1-(4-ethoxyphenyl)-2-(6-heptyl-pyridazin-3-yl)-acetylene
1-(4-ethoxyphenyl)-2-(6-octyl-pyridazin-3-yl)-acetylene
1-(4-propyloxyphenyl)-2-(6-methyl-pyridazin-3-yl)-acetylene
1-(4-propyloxyphenyl)-2-(6-ethyl-pyridazin-3-yl)-acetylene
1-(4-propyloxyphenyl)-2-(6-propyl-pyridazin-3-yl)-acetylene
1-(4-propyloxyphenyl)-2-(6-butyl-pyridazin-3-yl)-acetylene
1-(4-propyloxyphenyl)-2-(6-pentyl-pyridazin-3-yl)-acetylene
1-(4-propyloxyphenyl)-2-(6-hexyl-pyridazin-3-yl)-acetylene
1-(4-propyloxyphenyl)-2-(6-heptyl-pyridazin-3-yl)-acetylene
1-(4-propyloxyphenyl)-2-(6-octyl-pyridazin-3-yl)-acetylene
1-(4-butyloxyphenyl)-2-(6-methyl-pyridazin-3-yl)-acetylene
1-(4-butyloxyphenyl)-2-(6-ethyl-pyridazin-3-yl)-acetylene
1-(4-butyloxyphenyl)-2-(6-propyl-pyridazin-3-yl)-acetylene
1-(4-butyloxyphenyl)-2-(6-butyl-pyridazin-3-yl)-acetylene
1-(4-butyloxyphenyl)-2-(6-pentyl-pyridazin-3-yl)-acetylene
1-(4-butyloxyphenyl)-2-(6-hexyl-pyridazin-3-yl)-acetylene
1-(4-butyloxyphenyl)-2-(6-heptyl-pyridazin-3-yl)-acetylene
1-(4-butyloxyphenyl)-2-(6-octyl-pyridazin-3-yl)-acetylene
1-(4-methoxyphenyl)-2-(6-methyl-pyridazin-3-yl)-acetylene
1-(4-methoxyphenyl)-2-(6-ethyl-pyridazin-3-yl)-acetylene
1-(4-methoxyphenyl)-2-(6-propyl-pyridazin-3-yl)-acetylene
1-(4-methoxyphenyl)-2-(6-butyl-pyridazin-3-yl)-acetylene
1-(4-methoxyphenyl)-2-(6-pentyl-pyridazin-3-yl)-acetylene
1-(4-methoxyphenyl)-2-(6-hexyl-pyridazin-3-yl)-acetylene
1-(4-methoxyphenyl)-2-(6-heptyl-pyridazin-3-yl)-acetylene
1-(4-methoxyphenyl)-2-(6-octyl-pyridazin-3-yl)-acetylene
1-[4-(trans-4-propylcyclohexyl)phenyl]-2-(5-methyl-pyridin-2-yl)-acetylene; M. 137°, C. 217°
1-[4-(trans-4-propylcyclohexyl)phenyl]-2-(5-ethylpyridin-2-yl)-acetylene
1-[4-(trans-4-propylcyclohexyl)phenyl]-2-(5-propyl-pyridin-2-yl)-acetylene
1-[4-(trans-4-propylcyclohexyl)phenyl]-2-(5-butylpyridin-2-yl)-acetylene
1-[4-(trans-4-propylcyclohexyl)phenyl]-2-(5-pentylpyridin-2-yl)-acetylene
1-[4-(trans-4-propylcyclohexyl)phenyl]-2-(5-hexylpyridin-2-yl)-acetylene
1-[4-(trans-4-butylcyclohexyl)phenyl]-2-(5-methylpyridin-2-yl)-acetylene
1-[4-(trans-4-butylcyclohexyl)phenyl]-2-(5-ethylpyridin-2-yl)-acetylene
1-[4-(trans-4-butylcyclohexyl)phenyl]-2-(5-propylpyridin-2-yl)-acetylene
1-[4-(trans-4-butylcyclohexyl)phenyl]-2-(5-butylpyridin-2-yl)-acetylene
1-[4-(trans-4-butylcyclohexyl)phenyl]-2-(5-pentylpyridin-2-yl)-acetylene
1-[4-(trans-4-butylcyclohexyl)phenyl]-2-(5-hexylpyridin-2-yl)-acetylene
1-[4-(trans-4-pentylcyclohexyl)phenyl]-2-(5-methyl-pyridin-2-yl)-acetylene
1-[4-(trans-4-pentylcyclohexyl)phenyl]-2-(5-ethylpyridin-2-yl)-acetylene
1-[4-(trans-4-pentylcyclohexyl)phenyl]-2-(5-propylpyridin-2-yl)-acetylene
1-[4-(trans-4-pentylcyclohexyl)phenyl]-2-(5-butylpyridin-2-yl)-acetylene
1-[4-(trans-4-pentylcyclohexyl)phenyl]-2-(5-pentylpyridin-2-yl)-acetylene
1-[4-(trans-4-pentylcyclohexyl)phenyl]-2-(5-hexylpyridin-2-yl)-acetylene
1-[4-(trans-4-pentylcyclohexyl)phenyl]-2-(5-heptylpyridin-2-yl)-acetylene
1-[4-(trans-4-hexylcyclohexyl)phenyl]-2-(5-methylpyridin-2-yl)-acetylene
1-[4-(trans-4-hexylcyclohexyl)phenyl]-2-(5-ethylpyridin-2-yl)-acetylene
1-[4-(trans-4-hexylcyclohexyl)phenyl]-2-(5-propylpyridin-2-yl)-acetylene
1-[4-(trans-4-hexylcyclohexyl)phenyl]-2-(5-butylpyridin-2-yl)-acetylene
1-[4-(trans-4-hexylcyclohexyl)phenyl]-2-(5-pentylpyridin-2-yl)-acetylene
1-[4-(trans-4-hexylcyclohexyl)phenyl]-2-(5-hexylpyridin-2-yl)-acetylene
1-[4-(trans-4-propylcyclohexyl)phenyl]-2-(5-methyloxypyridin-2-yl)-acetylene
1-[4-(trans-4-propylcyclohexyl)phenyl]-2-(5-ethyloxypyridin-2-yl)-acetylene
1-[4-(trans-4-propylcyclohexyl)phenyl]-2-(5-propyloxypyridin-2-yl)-acetylene 1-[4-(trans-4-propylcyclohexyl)phenyl]-2-(5-butyloxypyridin-2-yl)-acetylene
1-[4-(trans-4-propylcyclohexyl)phenyl]-2-(5-pentyloxypyridin-2-yl)-acetylene
1-[4-(trans-4-propylcyclohexyl)phenyl]-2-(5-hexyloxypyridin-2-yl)-acetylene
1-[4-(trans-4-butylcyclohexyl)phenyl]-2-(5-methyloxypyridin-2-yl)-acetylene
1-[4-(trans-4-butylcyclohexyl)phenyl]-2-(5-ethyloxypyridin-2-yl)-acetylene
1-[4-(trans-4-butylcyclohexyl)phenyl]-2-(5-propyloxypyridin-2-yl)-acetylene
1-[4-(trans-4-butylcyclohexyl)phenyl]-2-(5-butyloxypyridin-2-yl)-acetylene
1-[4-(trans-4-butylcyclohexyl)phenyl]-2-(5-pentyloxypyridin-2-yl)-acetylene
1-[4-(trans-4-pentylcyclohexyl)phenyl]-2-(5-methyloxypyridin-2-yl)-acetylene
1-[4-(trans-4-pentylcyclohexyl)phenyl]-2-(5-ethyloxypyridin-2-yl)-acetylene
1-[4-(trans-4-pentylcyclohexyl)phenyl]-2-(5-propyloxypyridin-2-yl)-acetylene
1-[4-(trans-4-pentylcyclohexyl)phenyl]-2-(5-butyloxypyridin-2-yl)-acetylene
1-[4-(trans-4-pentylcyclohexyl)phenyl]-2-(5-pentyloxypyridin-2-yl)-acetylene
1-[4-(trans-4-pentylcyclohexyl)phenyl]-2-(5-hexyloxypyridin-2-yl)-acetylene
1-[4-(trans-4-ethylcyclohexyl)phenyl]-2-(5-methyloxypyridin-2-yl)-acetylene
1-[4-(trans-4-ethylcyclohexyl)phenyl]-2-(5-ethyloxypyridin-2-yl)-acetylene
1-[4-(trans-4-ethylcyclohexyl)phenyl]-2-(5-propyloxypyridin-2-yl)-acetylene
1-[4-(trans-4-ethylcyclohexyl)phenyl]-2-(5-butyloxypyridin-2-yl)-acetylene
1-[4-(trans-4-ethylcyclohexyl)phenyl]-2-(5-pentyloxypyridin-2-yl)-acetylene
1-[4-(trans-4-ethylcyclohexyl)phenyl]-2-(5-hexyloxypyridin-2-yl)-acetylene
1-[4-(trans-4-propylcyclohexyl)phenyl]-2-(5-methylpyrimidin-2-yl)-acetylene
1-[4-(trans-4-propylcyclohexyl)phenyl]-2-(5-ethylpyrimidin-2-yl)-acetylene
1-[4-(trans-4-propylcyclohexyl)phenyl]-2-(5-propylpyrimidin-2-yl)-acetylene
1-[4-(trans-4-propylcyclohexyl)phenyl]-2-(5-butylpyrimidin-2-yl)-acetylene
1-[4-(trans-4-propylcyclohexyl)phenyl]-2-(5-pentylpyrimidin-2-yl)-acetylene
1-[4-(trans-4-propylcyclohexyl)phenyl]-2-(5-hexylpyrimidin-2-yl)-acetylene
1-[4-(trans-4-propylcyclohexyl)phenyl]-2-(5-heptylpyrimidin-2-yl)-acetylene
1-[4-(trans-4-propylcyclohexyl)phenyl]-2-(5-octylpyrimidin-2-yl)-acetylene
1-[4-(trans-4-butylcyclohexyl)phenyl]-2-(5-methylpyrimidin-2-yl)-acetylene
1-[4-(trans-4-butylcyclohexyl)phenyl]-2-(5-ethylpyrimidin-2-yl)-acetylene
1-[4-(trans-4-butylcyclohexyl)phenyl]-2-(5-propylpyrimidin-2-yl)-acetylene
1-[4-(trans-4-butylcyclohexyl)phenyl]-2-(5-butylpyrimidin-2-yl)-acetylene
1-[4-(trans-4-butylcyclohexyl)phenyl]-2-(5-pentylpyrimidin-2-yl)-acetylene
1-[4-(trans-4-butylcyclohexyl)phenyl]-2-(5-hexylpyrimidin-2-yl)-acetylene
1-[4-(trans-4-pentylcyclohexyl)phenyl]-2-(5-methylpyrimidin-2-yl)-acetylene
1-[4-(trans-4-pentylcyclohexyl)phenyl]-2-(5-ethylpyrimidin-2-yl)-acetylene
1-[4-(trans-4-pentylcyclohexyl)phenyl]-2-(5-propylpyrimidin-2-yl)-acetylene
1-[4-(trans-4-pentylcyclohexyl)phenyl]-2-(5-butylpyrimidin-2-yl)-acetylene
1-[4-(trans-4-pentylcyclohexyl)phenyl]-2-(5-pentylpyrimidin-2-yl)-acetylene
1-[4-(trans-4-pentylcyclohexyl)phenyl]-2-(5-hexylpyrimidin-2-yl)-acetylene
1-[4-(trans-4-ethylcyclohexyl)phenyl]-2-(5-methylpyrimidin-2-yl)-acetylene
1-[4-(trans-4-ethylcyclohexyl)phenyl]-2-(5-ethylpyrimidin-2-yl)-acetylene
1-[4-(trans-4-ethylcyclohexyl)phenyl]-2-(5-propylpyrimidin-2-yl)-acetylene
1-[4-(trans-4-ethylcyclohexyl)phenyl]-2-(5-butylpyrimidin-2-yl)-acetylene
1-[4-(trans-4-ethylcyclohexyl)phenyl]-2-(5-pentylpyrimidin-2-yl)-acetylene
1-[4-(trans-4-ethylcyclohexyl)phenyl]-2-(5-hexylpyrimidin-2-yl)-acetylene
1-[4-(trans-4-propylcyclohexyl)phenyl]-2-(5-methyloxypyrimidin-2-yl)-acetylene
1-[4-(trans-4-propylcyclohexyl)phenyl]-2-(5-ethyloxypyrimidin-2-yl)-acetylene
1-[4-(trans-4-propylcyclohexyl)phenyl]-2-(5-propyloxypyrimidin-2-yl)-acetylene
1-[4-(trans-4-propylcyclohexyl)phenyl]-2-(5-butyloxypyrimidin-2-yl)-acetylene
1-[4-(trans-4-propylcyclohexyl)phenyl]-2-(5-pentyloxypyrimidin-2-yl)-acetylene
1-[4-(trans-4-propylcyclohexyl)phenyl]-2-(5-hexyloxypyrimidin-2-yl)-acetylene
1-[4-(trans-4-propylcyclohexyl)phenyl]-2-(5-heptyloxypyrimidin-2-yl)-acetylene
1-[4-(trans-4-propylcyclohexyl)phenyl]-2-(5-octyloxypyrimidin-2-yl)-acetylene
1-[4-(trans-4-butylcyclohexyl)phenyl]-2-(5-methyloxypyrimidin-2-yl)-acetylene
1-[4-(trans-4-butylcyclohexyl)phenyl]-2-(5-ethyloxypyrimidin-2-yl)-acetylene
1-[4-(trans-4-butylcyclohexyl)phenyl]-2-(5-propyloxypyrimidin-2-yl)-acetylene
1-[4-(trans-4-butylcyclohexyl)phenyl]-2-(5-butyloxypyrimidin-2-yl)-acetylene
1-[4-(trans-4-butylcyclohexyl)phenyl]-2-(5-pentyloxypyrimidin-2-yl)-acetylene
1-[4-(trans-4-ethylcyclohexyl)phenyl]-2-(5-methyloxypyrimidin-2-yl)-acetylene
1-[4-(trans-4-ethylcyclohexyl)phenyl]-2-(5-ethyloxypyrimidin-2-yl)-acetylene
1-[4-(trans-4-ethylcyclohexyl)phenyl]-2-(5-propyloxypyrimidin-2-yl)-acetylene
1-[4-(trans-4-ethylcyclohexyl)phenyl]-2-(5-butyloxypyrimidin-2-yl)-acetylene
1-[4-(trans-4-ethylcyclohexyl)phenyl]-2-(5-pentyloxypyrimidin-2-yl)-acetylene
1-[4-(trans-4-ethylcyclohexyl)phenyl]-2-(5-hexyloxypyrimidin-2-yl)-acetylene
1-[4-(trans-4-methylcyclohexyl)phenyl]-2-(5-methyloxypyrimidin-2-yl)-acetylene
1-[4-(trans-4-methylcyclohexyl)phenyl]-2-(5-ethyloxypyrimidin-2-yl)-acetylene
1-[4-(trans-4-methylcyclohexyl)phenyl]-2-(5-propyloxypyrimidin-2-yl)-acetylene 1-[4-(trans-4-methylcyclohexyl)phenyl]-2-(5-butyloxypyrimidin-2-yl)-acetylene
1-[4-(trans-4-methylcyclohexyl)phenyl]-2-(5-pentyloxypyrimidin-2-yl)-acetylene
1-[4-(trans-4-methylcyclohexyl)phenyl]-2-(5-hexyloxypyrimidin-2-yl)-acetylene

EXAMPLE 3

Analogously to Example 1, 1-(p-propylphenyl)-2-(5-chloro-pyridin-2-yl)-acetylene is obtained by reaction of p-propylphenylacetylene (which can be prepared, for example, analogously to the method of Smith, Hoehn, Amer. Soc. 63 1175 (1941)) and 2-bromo-5-chloro-pyridine in the presence of bis-(triphenylphosphine)-palladium(II) chloride and copper(I) iodide.

The following compounds are prepared analogously:
1-(p-methylphenyl)-2-(5-chloro-pyridin-2-yl)-acetylene
1-(p-ethylphenyl)-2-(5-chloro-pyridin-2-yl)-acetylene
1-(p-butylphenyl)-2-(5-chloro-pyridin-2-yl)-acetylene
1-(p-pentylphenyl)-2-(5-chloro-pyridin-2-yl)-acetylene
1-(p-hexylphenyl)-2-(5-chloro-pyridin-2-yl)-acetylene
1-(p-methoxyphenyl)-2-(5-chloro-pyridin-2-yl)-acetylene
1-(p-ethoxyphenyl)-2-(5-chloro-pyridin-2-yl)-acetylene
1-(p-propoxyphenyl)-2-(5-chloro-pyridin-2-yl)-acetylene
1-(p-butyloxyphenyl)-2-(5-chloro-pyridin-2-yl)-acetylene
1-(p-pentyloxyphenyl)-2-(5-chloro-pyridin-2-yl)-acetylene
1-(p-hexyloxyphenyl)-2-(5-chloro-pyridin-2-yl)-acetylene
1-(p-methylphenyl)-2-(5-chloro-pyrimidin-2-yl)-acetylene
1-(p-ethylphenyl)-2-(5-chloro-pyrimidin-2-yl)-acetylene
1-(p-propylphenyl)-2-(5-chloro-pyrimidin-2-yl)-acetylene
1-(p-butylphenyl)-2-(5-chloro-pyrimidin-2-yl)-acetylene
1-(p-pentylphenyl)-2-(5-chloro-pyrimidin-2-yl)-acetylene
1-(p-hexylphenyl)-2-(5-chloro-pyrimidin-2-yl)-acetylene
1-(p-methoxyphenyl)-2-(5-chloro-pyrimidin-2-yl)-acetylene
1-(p-ethoxyphenyl)-2-(5-chloro-pyrimidin-2-yl)-acetylene
1-(p-propoxyphenyl)-2-(5-chloro-pyrimidin-2-yl)-acetylene
1-(p-butyloxyphenyl)-2-(5-chloro-pyrimidin-2-yl)-acetylene
1-(p-pentyloxyphenyl)-2-(5-chloro-pyrimidin-2-yl)-acetylene
1-(p-hexyloxyphenyl)-2-(5-chloro-pyrimidin-2-yl)-acetylene
1-(p-methoxyphenyl)-2-(6-chloro-pyridazin-3-yl)-acetylene
1-(p-ethoxyphenyl)-2-(6-chloro-pyridazin-3-yl)-acetylene
1-(p-propoxyphenyl)-2-(6-chloro-pyridazin-3-yl)-acetylene
1-(p-butyloxyphenyl)-2-(6-chloro-pyridazin-3-yl)-acetylene
1-(p-pentyloxyphenyl)-2-(6-chloro-pyridazin-3-yl)-acetylene
1-(p-hexyloxyphenyl)-2-(6-chloro-pyridazin-3-yl)-acetylene
1-(p-methoxyphenyl)-2-(5-chloro-pyrazin-2-yl)-acetylene
1-(p-ethoxyphenyl)-2-(5-chloro-pyrazin-2-yl)-acetylene
1-(p-propoxyphenyl)-2-(5-chloro-pyrazin-2-yl)-acetylene
1-(p-butyloxyphenyl)-2-(5-chloro-pyrazin-2-yl)-acetylene
1-(p-pentyloxyphenyl)-2-(5-chloro-pyrazin-2-yl)-acetylene
1-(p-hexyloxyphenyl)-2-(5-chloro-pyrazin-2-yl)-acetylene
1-(p-methylphenyl)-2-(6-chloro-pyridazin-3-yl)-acetylene
1-(p-ethylphenyl)-2-(6-chloro-pyridazin-3-yl)-acetylene
1-(p-propylphenyl)-2-(6-chloro-pyridazin-3-yl)-acetylene
1-(p-butylphenyl)-2-(6-chloro-pyridazin-3-yl)-acetylene
1-(p-pentylphenyl)-2-(6-chloro-pyridazin-3-yl)-acetylene
1-(p-hexylphenyl)-2-(6-chloro-pyridazin-3-yl)-acetylene
1-(p-methylphenyl)-2-(5-chloro-pyrazin-2-yl)-acetylene
1-(p-ethylphenyl)-2-(5-chloro-pyrazin-2-yl)-acetylene
1-(p-propylphenyl)-2-(5-chloro-pyrazin-2-yl)-acetylene
1-(p-butylphenyl)-2-(5-chloro-pyrazin-2-yl)-acetylene
1-(p-pentylphenyl)-2-(5-chloro-pyrazin-2-yl)-acetylene
1-(p-hexylphenyl)-2-(5-chloro-pyrazin-2-yl)-acetylene

EXAMPLE 4

Analogously to Example 1, the corresponding 1-(trans-4-pentylcyclohexyl)-2-[4-{2-(trans-4-pentylcyclohexyl)-ethynyl}-phenyl]-acetylene is obtained by reaction of 0.02 mol of trans-4-pentylcyclohexylacetylene and 0.01 mol of 1,4-dibromobenzene.

The following compounds are prepared analogously:
1-(trans-4-ethylcyclohexyl)-2-[4-{2-(trans-4-ethylcyclohexyl)-ethynyl}-phenyl]-acetylene
1-(trans-4-propylcyclohexyl)-2-[4-{2-(trans-4-propylcyclohexyl)-ethynyl}-phenyl]-acetylene
1-(trans-4-butylcyclohexyl)-2-[4-{2-(trans-4-butylcyclohexyl)-ethynyl}-phenyl]-acetylene
1-(trans-4-hexylcyclohexyl)-2-[4-{2-(trans-4-hexylcyclohexyl)-ethynyl}-phenyl]-acetylene
1-(trans-4-ethylcyclohexyl)-2-[5-{2-(trans-4-ethylcyclohexyl)-ethynyl}-pyridin-2-yl]-acetylene
1-(trans-4-propylcyclohexyl)-2-[5-{2-(trans-4-propylcyclohexyl)-ethynyl}-pyridin-2-yl]-acetylene
1-(trans-4-butylcyclohexyl)-2-[5-{2-(trans-4-butylcyclohexyl)-ethynyl}-pyridin-2-yl]- acetylene
1-(trans-4-pentylcyclohexyl)-2-[5-{2-(trans-4-pentylcyclohexyl)-ethynyl}-pyridin-2-yl]-acetylene
1-(trans-4-hexylcyclohexyl)-2-[5-{2-(trans-4-hexylcyclohexyl)-ethynyl}-pyridin-2-yl]-acetylene
1-(4-ethylphenyl)-2-[5-{2-(4-ethylphenyl)-ethynyl}pyridin-2-yl]-acetylene
1-(4-propylphenyl)-2-[5-{2-(4-propylphenyl)-ethynyl}pyridin-2-yl]-acetylene
1-(4-butylphenyl)-2-[5-{2-(4-butylphenyl)-ethynyl}pyridin-2-yl]-acetylene
1-(4-pentylphenyl)-2-[5-{2-(4-pentylphenyl)-ethynyl}pyridin-2-yl]-acetylene
1-(4-hexylphenyl)-2-[5-{2-(4-hexylphenyl)-ethynyl}pyridin-2-yl]-acetylene
1-(trans-4-ethylcyclohexyl)-2-[6-{2-(trans-4-ethylcyclohexyl)-ethynyl}-pyridazin-3-yl]-acetylene
1-(trans-4-propylcyclohexyl)-2-[6-{2-(trans-4-propylcyclohexyl)-ethynyl}-pyridazin-3-yl]-acetylene
1-(trans-4-butylcyclohexyl)-2-[6-{2-(trans-4-butylcyclohexyl)-ethynyl}-pyridazin-3-yl]-acetylene
1-(trans-4-pentylcyclohexyl)-2-[6-{2-(trans-4-pentylhexyl)-ethynyl}-pyridazin-3-yl]-acetylene 1-(trans-4-hexylcyclohexyl)-2-[6-{2-(trans-4-hexylcyclohexyl)-ethynyl}-pyridazin-3-yl]-acetylene
1-(4-ethylphenyl)-2-[6-{2-(4-ethylphenyl)-ethynyl}pyridazin-3-yl]-acetylene
1-(4-propylphenyl)-2-[6-{2-(4-propylphenyl)-ethynyl}pyridazin-3-yl]-acetylene
1-(4-butylphenyl)-2-[6-{2-(4-butylphenyl)-ethynyl}pyridazin-3-yl]-acetylene
1-(4-pentylphenyl)-2-[6-{2-(4-pentylphenyl)-ethynyl}pyridazin-3-yl]-acetylene
1-(4-hexylphenyl)-2-[6-{2-(4-hexylphenyl)-ethynyl}pyridazin-3-yl]-acetylene
1-(4-ethoxyphenyl)-2-[6-{2-(4-ethoxyphenyl)-ethynyl}pyridazin-3-yl]-acetylene
1-(4-propoxyphenyl)-2-[6-{2-(4-propoxyphenyl)-ethynyl}pyridazin-3-yl]-acetylene
1-(4-butyloxyphenyl)-2-[6-{2-(4-butyloxyphenyl)-ethynyl}pyridazin-3-yl]-acetylene
1-(4-pentyloxyphenyl)-2-[6-{2-(4-pentyloxyphenyl)ethynyl}pyridazin-3-yl]-acetylene
1-(4-methoxyphenyl)-2-[6-{2-(4-methoxyphenyl)-ethynyl}pyridazin-3-yl]-acetylene
1-(4-ethoxyphenyl)-2-[5-{2-(4-ethoxyphenyl)-ethynyl}pyridin-2-yl]-acetylene
1-(4-propoxyphenyl)-2-[5-{2-(4-propoxyphenyl)-ethynyl}pyridin-2-yl]-acetylene
1-(4-butyloxyphenyl)-2-[5-{2-(4-butyloxyphenyl)-ethynyl}pyridin-2-yl]-acetylene
1-(4-pentyloxyphenyl)-2-[5-{2-(4-pentyloxyphenyl)ethynyl}pyridin-2-yl]-acetylene
1-(4-methoxyphenyl)-2-[5-{2-(4-methoxyphenyl)-ethynyl}pyridin-2-yl]-acetylene
1-(trans-4-ethylcyclohexyl)-2-[5-{2-(trans-4-ethylcyclohexyl)-ethynyl}-pyrimidin-2-yl]-acetylene
1-(trans-4-propylcyclohexyl)-2-[5-{2-(trans-4-propylcyclohexyl)-ethynyl}-pyrimidin-2-yl]-acetylene
1-(trans-4-butylcyclohexyl)-2-[5-{2-(trans-4-butylcyclohexyl)-ethynyl}-pyrimidin-2-yl]-acetylene
1-(trans-4-pentylcyclohexyl)-2-[5-{2-(trans-4-pentylcyclohexyl)-ethynyl}-pyrimidin-2-yl]-acetylene
1-(trans-4-hexylcyclohexyl)-2-[5-{2-(trans-4-hexylcyclohexyl)-ethynyl}-pyrimidin-2-yl]-acetylene
1-(4-ethoxyphenyl)-2-[5-{2-(4-ethoxyphenyl)-ethynyl}pyrimidin-2-yl]-acetylene
1-(4-propoxyphenyl)-2-[5-{2-(4-propoxyphenyl)-ethynyl}pyrimidin-2-yl]-acetylene
1-(4-butyloxyphenyl)-2-[5-{2-(4-butyloxyphenyl)-ethynyl}pyrimidin-2-yl]-acetylene
1-(4-pentyloxyphenyl)-2-[5-{2-(4-pentyloxyphenyl)ethynyl}-pyrimidin-2-yl]-acetylene
1-(4-hexyloxyphenyl)-2-[5-{2-(4-hexyloxyphenyl)-ethynyl}pyrimidin-2-yl]-acetylene
1-(4-heptyloxyphenyl)-2-[5-{2-(4-heptyloxyphenyl)-ethynyl}-pyrimidin-2-yl]-acetylene
1-(4-octyloxyphenyl)-2-[5-{2-(4-octyloxyphenyl)-ethynyl}pyrimidin-2-yl]-acetylene

EXAMPLE 5

Analogously to Example 1, the corresponding 1-(4-propylbicyclo(2.2.2)octyl-2-(4-ethoxyphenyl)-acetylene is obtained by reaction of 4-propylbicyclo(2.2.2)octylacetylene (which can be prepared from 4-propylbicyclo(2.2.2)octanecarboxylic acid by reaction with methyllithium and $PCl_5$ and subsequent dehydrohalogenation) with 4-ethoxy-iodobenzene.

The following compounds are prepared analogously:
1-(4-ethylbicyclo(2.2.2)octyl)-2-(4-ethoxyphenyl)-acetylene
1-(4-butylbicyclo(2.2.2)octyl)-2-(4-ethoxyphenyl)-acetylene
1-(4-pentylbicyclo(2.2.2)octyl)-2-(4-ethoxyphenyl)acetylene
1-(4-ethylbicyclo(2.2.2)octyl)-2-(4-propoxyphenyl)acetylene
1-(4-propylbicyclo(2.2.2)octyl)-2-(4-propoxyphenyl)acetylene
1-(4-butylbicyclo(2.2.2)octyl)-2-(4-propoxyphenyl)acetylene
1-(4-ethylbicyclo(2.2.2)octyl)-2-(4-butyloxyphenyl)acetylene
1-(4-propylbicyclo(2.2.2)octyl)-2-(4-butyloxyphenyl)acetylene
1-(4-butylbicyclo(2.2.2)octyl)-2-(4-butyloxyphenyl)acetylene
1-(4-ethylbicyclo(2.2.2)octyl)-2-(4-methoxyphenyl)acetylene
1-(4-propylbicyclo(2.2.2)octyl)-2-(4-methoxyphenyl)acetylene
1-(4-butylbicyclo(2.2.2)octyl)-2-(4-methoxyphenyl)-acetylene
1-(4-ethylbicyclo(2.2.2)octyl)-2-(4-ethylphenyl)-acetylene
1-(4-propylbicyclo(2.2.2)octyl)-2-(4-ethylphenyl)-acetylene
1-(4-butylbicyclo(2.2.2)octyl)-2-(4-ethylphenyl)-acetylene
1-(4-pentylbicyclo(2.2.2)octyl)-2-(4-ethylphenyl)-acetylene
1-(4-hexylbicyclo(2.2.2)octyl)-2-(4-ethylphenyl)-acetylene
1-(4-ethylbicyclo(2.2.2)octyl)-2-(4-propylphenyl)acetylene
1-(4-propylbicyclo(2.2.2)octyl)-2-(4-propylphenyl)acetylene
1-(4-butylbicyclo(2.2.2)octyl)-2-(4-propylphenyl)acetylene
1-(4-pentylbicyclo(2.2.2)octyl)-2-(4-propylphenyl)acetylene
1-(4-hexylbicyclo(2.2.2)octyl)-2-(4-propylphenyl)acetylene
1-(4-ethylbicyclo(2.2.2)octyl)-2-(3-fluoro-4-ethylphenyl)-acetylene
1-(4-propylbicyclo(2.2.2)octyl)-2-(3-fluoro-4-ethylphenyl)-acetylene
1-(4-butylbicyclo(2.2.2)octyl)-2-(3-fluoro-4-ethylphenyl)-acetylene
1-(4-pentylbicyclo(2.2.2)octyl)-2-(3-fluoro-4-ethylphenyl)-acetylene
1-(4-hexylbicyclo(2.2.2)octyl)-2-(3-fluoro-4-ethylphenyl)-acetylene
1-(4-ethylbicyclo(2.2.2)octyl)-2-(3-fluoro-4-propylphenyl)-acetylene
1-(4-propylbicyclo(2.2.2)octyl)-2-(3-fluoro-4-propylphenyl)-acetylene
1-(4-butylbicyclo(2.2.2)octyl)-2-(3-fluoro-4-propylphenyl)-acetylene
1-(4-pentylbicyclo(2.2.2)octyl)-2-(3-fluoro-4-propylphenyl)-acetylene
1-(4-hexylbicyclo(2.2.2)octyl)-2-(3-fluoro-4-propylphenyl)-acetylene
1-[4-(trans-4-ethylcyclohexyl)-bicyclo(2.2.2)octyl]-2(4-ethoxyphenyl)-acetylene
1-[4-(trans-4-propylcyclohexyl)-bicyclo(2.2.2)octyl]-2(4-ethoxyphenyl)-acetylene
1-[4-(trans-4-butylcyclohexyl)-bicyclo(2.2.2)octyl]-2(4-ethoxyphenyl)-acetylene 1-[4-(trans-4-ethylcyclohexyl)-bicyclo(2.2.2)octyl]-2-(4-propoxyphenyl)-acetylene
1-[4-(trans-4-propylcyclohexyl)-bicyclo(2.2.2)octyl]-2-(4-propoxyphenyl)-acetylene
1-[4-(trans-4-butylcyclohexyl)-bicyclo(2.2.2)octyl]-2-(4-propoxyphenyl)-acetylene
1-[4-(trans-4-pentylcyclohexyl)-bicyclo(2.2.2)octyl]-2-(4-propoxyphenyl)-acetylene
1-[4-(trans-4-hexylcyclohexyl)-bicyclo(2.2.2)octyl]-2-(4-propoxyphenyl)-acetylene
1-[4-(trans-4-ethylcyclohexyl)-bicyclo(2.2.2)octyl]-2-(4-ethylphenyl)-acetylene
1-[4-(trans-4-propylcyclohexyl)-bicyclo(2.2.2)octyl]-2-(4-ethylphenyl)-acetylene
1-[4-(trans-4-butylcyclohexyl)-bicyclo(2.2.2)octyl]-2-(4-ethylphenyl)-acetylene
1-[4-(trans-4-pentylcyclohexyl)-bicyclo(2.2.2)octyl]-2-(4-ethylphenyl)-acetylene
1-[4-(trans-4-ethylcyclohexyl)-bicyclo(2.2.2)octyl]-2-(4-propylphenyl)-acetylene
1-[4-(trans-4-propylcyclohexyl)-bicyclo(2.2.2)octyl]-2-(4-propylphenyl)-acetylene
1-[4-(trans-4-butylcyclohexyl)-bicyclo(2.2.2)octyl]-2-(4-propylphenyl)-acetylene
1-[4-(trans-4-pentylcyclohexyl)-bicyclo(2.2.2)octyl]-2-(4-propylphenyl)-acetylene
1-[4-(trans-4-hexylcyclohexyl)-bicyclo(2.2.2)octyl]-2-(4-propylphenyl)-acetylene
1-[4-(trans-4-ethylcyclohexyl)-bicyclo(2.2.2)octyl]-2-(4-butylphenyl)-acetylene
1-[4-(trans-4-propylcyclohexyl)-bicyclo(2.2.2)octyl]-2-(4-butylphenyl)-acetylene
1-[4-(trans-4-butylcyclohexyl)-bicyclo(2.2.2)octyl]-2-(4-butylphenyl)-acetylene
1-[4-(trans-4-pentylcyclohexyl)-bicyclo(2.2.2)octyl]-2-(4-butylphenyl)-acetylene
1-[4-(trans-4-hexylcyclohexyl)-bicyclo(2.2.2)octyl]-2-(4-butylphenyl)-acetylene
1-[4-(trans-4-ethylcyclohexyl)-bicyclo(2.2.2)octyl]-2-(4-pentylphenyl)-acetylene
1-[4-(trans-4-propylcyclohexyl)-bicyclo(2.2.2)octyl]-2-(4-pentylphenyl)-acetylene
1-[4-(trans-4-butylcyclohexyl)-bicyclo(2.2.2)octyl]-2-(4-pentylphenyl)-acetylene
1-[4-(trans-4-pentylcyclohexyl)-bicyclo(2.2.2)octyl]-2-(4-pentylphenyl)-acetylene
1-[4-(trans-4-hexylcyclohexyl)-bicyclo(2.2.2)octyl]-2-(4-pentylphenyl)-acetylene
1-[4-(trans-4-ethylphenyl)-bicyclo(2.2.2)octyl]-2-(4-ethoxyphenyl)-acetylene
1-[4-(trans-4-propylphenyl)-bicyclo(2.2.2)octyl]-2-(4-ethoxyphenyl)-acetylene
1-[4-(trans-4-butylphenyl)-bicyclo(2.2.2)octyl]-2-(4-ethoxyphenyl)-acetylene
1-[4-(trans-4-pentylphenyl)-bicyclo(2.2.2)octyl]-2-(4-ethoxyphenyl)-acetylene
1-[4-(trans-4-hexylphenyl)-bicyclo(2.2.2)octyl]-2-(4-ethoxyphenyl)-acetylene
1-[4-(trans-4-ethylphenyl)-bicyclo(2.2.2)octyl]-2-(4-propoxyphenyl)-acetylene
1-[4-(trans-4-propylphenyl)-bicyclo(2.2.2)octyl]-2-(4-propoxyphenyl)-acetylene
1-[4-(trans-4-butylphenyl)-bicyclo(2.2.2)octyl]-2-(4-propoxyphenyl)-acetylene
1-[4-(trans-4-pentylphenyl)-bicyclo(2.2.2)octyl]-2-(4-propoxyphenyl)-acetylene
1-[4-(trans-4-hexylphenyl)-bicyclo(2.2.2)octyl]-2-(4-propoxyphenyl)-acetylene
1-[4-(trans-4-ethylphenyl)-bicyclo(2.2.2)octyl]-2-(4-butyloxyphenyl)-acetylene
1-[4-(trans-4-propylphenyl)-bicyclo(2.2.2)octyl]-2-(4-butyloxyphenyl)-acetylene
1-[4-(trans-4-butylphenyl)-bicyclo(2.2.2)octyl]-2-(4-butyloxyphenyl)-acetylene
1-[4-(trans-4-pentylphenyl)-bicyclo(2.2.2)octyl]-2-(4-butyloxyphenyl)-acetylene
1-[4-(trans-4-hexylphenyl)-bicyclo(2.2.2)octyl]-2-(4-butyloxyphenyl)-acetylene
1-[4-(trans-4-ethylphenyl)-bicyclo(2.2.2)octyl]-2-(4-ethylphenyl)-acetylene
1-[4-(trans-4-propylphenyl)-bicyclo(2.2.2)octyl]-2-(4-ethylphenyl)-acetylene
1-[4-(trans-4-pentylphenyl)-bicyclo(2.2.2)octyl]-2-(4-ethylphenyl)-acetylene
1-[4-(trans-4-ethylphenyl)-bicyclo(2.2.2)octyl]-2-(4-propylphenyl)-acetylene
1-[4-(trans-4-propylphenyl)-bicyclo(2.2.2)octyl]-2-(4-propylphenyl)-acetylene
1-[4-(trans-4-butylphenyl)-bicyclo(2.2.2)octyl]-2-(4-propylphenyl)-acetylene
1-[4-(trans-4-propylphenyl)-bicyclo(2.2.2)octyl]-2-(4-butylphenyl)-acetylene
1-[4-(trans-4-butylphenyl)-bicyclo(2.2.2)octyl]-2-(4-butylphenyl)-acetylene
1-[4-(trans-4-pentylphenyl)-bicyclo(2.2.2)octyl]-2-(4-butylphenyl)-acetylene
1-[4-(trans-4-ethylphenyl)-bicyclo(2.2.2)octyl]-2-(4-pentylphenyl)-acetylene
1-[4-(trans-4-propylphenyl)-bicyclo(2.2.2)octyl]-2-(4-pentylphenyl)-acetylene
1-[4-(trans-4-butylphenyl)-bicyclo(2.2.2)octyl]-2-(4-pentylphenyl)-acetylene

EXAMPLE 6

A mixture of 0.04 g of bis-(tri-phenylphosphine)-palladium(II) chloride, 2.5 mmol of 4-pentylcyclohexen-1-yl trifluoromethylsulfonate (preparation analogous to the method of W.J. Scott, Tetrahedron Letters 24, 979), 3 mmol of 4-ethoxyphenylacetylene (preparation analogous to the method of Smith, Hoehn, Am. Soc. 63 (1941), 1175) 1.2 ml of triethylamine and 10 ml of dimethylformamide is warmed at about 75° for 1 hour, with stirring. Customary working up and purification by column chromatography gives 1-(4-pentylcyclohexen-1-yl)-2-(4-ethoxyphenyl)acetylene. The following compounds are prepared analogously:

1-(4-ethylcyclohexen-1-yl)-2-(4-ethoxyphenyl)-acetylene
1-(4-propylcyclohexen-1-yl)-2-(4-ethoxyphenyl)-acetylene
1-(4-butylcyclohexen-1-yl)-2-(4-ethoxyphenyl)-acetylene
1-(4-pentylcyclohexen-1-yl)-2-(4-ethoxyphenyl)-acetylene
1-(4-hexylcyclohexen-1-yl)-2-(4-ethoxyphenyl)-acetylene
1-(4-ethylcyclohexen-1-yl)-2-(4-propoxyphenyl)-acetylene
1-(4-propylcyclohexen-1-yl)-2-(4-propoxyphenyl)-acetylene
1-(4-butylcyclohexen-1-yl)-2-(4-propoxyphenyl)-acetylene
1-(4-pentylcyclohexen-1-yl)-2-(4-propoxyphenyl)-acetylene
1-(4-hexylcyclohexen-1-yl)-2-(4-propoxyphenyl)-acetylene 1-(4-ethylcyclohexen-1-yl)-2-(4-butyloxyphenyl)-acetylene
1-(4-propylcyclohexen-1-yl)-2-(4-butyloxyphenyl)-acetylene
1-(4-butylcyclohexen-1-yl)-2-(4-butyloxyphenyl)-acetylene
1-(4-pentylcyclohexen-1-yl)-2-(4-butyloxyphenyl)-acetylene
1-(4-hexylcyclohexen-1-yl)-2-(4-butyloxyphenyl)-acetylene
1-(4-ethylcyclohexen-1-yl)-2-(4-pentyloxyphenyl)-acetylene
1-(4-propylcyclohexen-1-yl)-2-(4-pentyloxyphenyl)-acetylene
1-(4-butylcyclohexen-1-yl)-2-(4-pentyloxyphenyl)-acetylene
1-(4-pentylcyclohexen-1-yl)-2-(4-pentyloxyphenyl)-acetylene
1-(4-hexylcyclohexen-1-yl)-2-(4-pentyloxyphenyl)-acetylene
1-(4-ethylcyclohexen-1-yl)-2-(4-ethylphenyl)-acetylene
1-(4-propylcyclohexen-1-yl)-2-(4-ethylphenyl)-acetylene
1-(4-butylcyclohexen-1-yl)-2-(4-ethylphenyl)-acetylene
1-(4-pentylcyclohexen-1-yl)-2-(4-ethylphenyl)-acetylene
1-(4-hexylcyclohexen-1-yl)-2-(4-ethylphenyl)-acetylene
1-(4-ethylcyclohexen-1-yl)-2-(4-propylphenyl)-acetylene
1-(4-propylcyclohexen-1-yl)-2-(4-propylphenyl)-acetylene
1-(4-butylcyclohexen-1-yl)-2-(4-propylphenyl)-acetylene
1-(4-pentylcyclohexen-1-yl)-2-(4-propylphenyl)-acetylene
1-(4-hexylcyclohexen-1-yl)-2-(4-propylphenyl)-acetylene
1-(4-ethylcyclohexen-1-yl)-2-(4-butylphenyl)-acetylene
1-(4-propylcyclohexen-1-yl)-2-(4-butylphenyl)-acetylene
1-(4-butylcyclohexen-1-yl)-2-(4-butylphenyl)-acetylene
1-(4-pentylcyclohexen-1-yl)-2-(4-butylphenyl)-acetylene
1-(4-hexylcyclohexen-1-yl)-2-(4-butylphenyl)-acetylene
1-(4-ethylcyclohexen-1-yl)-2-(4-pentylphenyl)-acetylene
1-(4-propylcyclohexen-1-yl)-2-(4-pentylphenyl)-acetylene
1-(4-butylcyclohexen-1-yl)-2-(4-pentylphenyl)-acetylene
1-(4-pentylcyclohexen-1-yl)-2-(4-pentylphenyl)-acetylene
1-(4-hexylcyclohexen-1-yl)-2-(4-pentylphenyl)-acetylene
1-(4-ethylcyclohexen-1-yl)-2-(4-hexylphenyl)-acetylene
1-(4-propylcyclohexen-1-yl)-2-(4-hexylhpenyl)-acetylene
1-(4-butylcyclohexen-1-yl-2-(4-hexylphenyl)-acetylene
1-(4-pentylcyclohexen-1-yl)-2-(4-hexylphenyl)-acetylene
1-(4-hexylcyclohexen-1-yl)-2-(4-hexylphenyl)-acetylene
1-(4-ethylcyclohexen-1-yl)-2-[4-(4-ethylcyclohexyl)-phenyl]-acetylene
1-(4-propylcyclohexen-1-yl)-2-[4-(4-ethylcyclohexyl)-phenyl]-acetylene
1-(4-butylcyclohexen-1-yl)-2-[4-(4-ethylcyclohexyl)-phenyl]-acetylene
1-(4-pentylcyclohexen-1-yl)-2-[4-(4-ethylcyclohexyl)-phenyl]-acetylene
1-(4-hexylcyclohexen-1-yl)-2-[4-(4-ethylcyclohexyl)-phenyl]-acetylene
1-(4-ethylcyclohexen-1-yl)-2-[4-(4-propylcyclohexyl)-phenyl]-acetylene
1-(4-propylcyclohexen-1-yl)-2-[4-(4-propylcyclohexyl)-phenyl]-acetylene
1-(4-butylcyclohexen-1-yl)-2-[4-(4-propylcyclohexyl)-phenyl]-acetylene
1-(4-pentylcyclohexen-1-yl)-2-[4-(4-propylcyclohexyl)-phenyl]-acetylene
1-(4-hexylcyclohexen-1-yl)-2-[4-(4-propylcyclohexyl)-phenyl]-acetylene
1-(4-ethylcyclohexen-1-yl)-2-[4-(4-butylcyclohexyl)-phenyl]-acetylene
1-(4-propylcyclohexen-1-yl)-2-[4-(4-butylcyclohexyl)-phenyl]-acetylene
1-(4-butylcyclohexen-1-yl)-2-[4-(4-butylcyclohexyl)-phenyl]-acetylene
1-(4-pentylcyclohexen-1-yl)-2-[4-(4-butylcyclohexyl)-phenyl]-acetylene
1-(4-hexylcyclohexen-1-yl)-2-[4-(4-butylcyclohexyl)-phenyl]-acetylene
1-(4-ethylcyclohexen-1-yl)-2-[4-(4-pentylcyclohexyl)-phenyl]-acetylene
1-(4-propylcyclohexen-1-yl)-2-[4-(4-pentylcyclohexyl)-phenyl]-acetylene
1-(4-butylcyclohexen-1-yl)-2-[4-(4-pentylcyclohexyl)-phenyl]-acetylene
1-(4-pentylcyclohexen-1-yl)-2-[4-(4-pentylcyclohexyl)-phenyl]-acetylene
1-(4-hexylcyclohexen-1-yl)-2-[4-(4-pentylcyclohexyl)-phenyl]-acetylene
1-(4-ethylcyclohexen-1-yl)-2-(4'-ethylbiphenyl-4-yl)acetylene
1-(4-propylcyclohexen-1-yl)-2-(4'-ethylbiphenyl-4-yl)acetylene
1-(4-butylcyclohexen-1-yl)-2-(4'-ethylbiphenyl-4-yl)acetylene
1-(4-pentylcyclohexen-1-yl)-2-(4'-ethylbiphenyl-4-yl)acetylene
1-(4-hexylcyclohexen-1-yl)-2-(4'-ethylbiphenyl-4-yl)acetylene
1-(4-ethylcyclohexen-1-yl)-2-(40'-propylbiphenyl-4-yl)acetylene
1-(4-propylcyclohexen-1-yl)-2-(40'-propylbiphenyl-4-yl)acetylene
1-(4-butylcyclohexen-1-yl)-2-(4'-propylbiphenyl-4-yl)acetylene
1-(4-pentylcyclohexen-1-yl)-2-(40'-propylbiphenyl-4-yl)acetylene
1-(4-hexylcyclohexen-1-yl)-2-(40'-propylbiphenyl-4-yl)acetylene
1-(4-ethylcyclohexen-1-yl)-2-(40'-butylbiphenyl-4-yl)acetylene
1-(4-propylcyclohexen-1-yl)-2-(40'-butylbiphenyl-4-yl)acetylene
1-(4-butylcyclohexen-1-yl)-2-(4'-butylbiphenyl-4-yl)acetylene
1-(4-pentylcyclohexen-1-yl)-2-(4'-butylbiphenyl-4-yl)acetylene
1-(4-hexylcyclohexen-1-yl)-2-(4'-butylbiphenyl-4-yl)acetylene
1-(4-ethylcyclohexen-1-yl)-2-(4'-pentylbiphenyl-4-yl)acetylene
1-(4-propylcyclohexen-1-yl)-2-(4'-pentylbiphenyl-4-yl)acetylene 1-(4-butylcyclohexen-1-yl)-2-(4'-pentylbiphenyl-4-yl)acetylene
1-(4-pentylcyclohexen-1-yl)-2-(4'-pentylbiphenyl-4-yl)acetylene
1-(4-hexylcyclohexen-1-yl)-2-(4'-pentylbiphenyl-4-yl)acetylene
1-(4-ethylcyclohexen-1-yl)-2-(4'-fluorobiphenyl-4-yl)acetylene
1-(4-propylcyclohexen-1-yl)-2-(4'-fluorobiphenyl-4-yl)acetylene
1-(4-butylcyclohexen-1-yl)-2-(4'-fluorobiphenyl-4-yl)acetylene
1-(4-pentylcyclohexen-1-yl)-2-(4'-fluorobiphenyl-4-yl)acetylene
1-(4-hexylcyclohexen-1-yl)-2-(4'-fluorobiphenyl-4-yl)acetylene
1-(4-ethylcyclohexen-1-yl)-2-(4'-cyanobiphenyl-4-yl)acetylene
1-(4-propylcyclohexen-1-yl)-2-(4'-cyanobiphenyl-4-yl)acetylene
1-(4-butylcyclohexen-1-yl)-2-(4'-cyanobiphenyl-4-yl)acetylene
1-(4-pentylcyclohexen-1-yl)-2-(4'-cyanobiphenyl-4-yl)acetylene
1-(4-hexylcyclohexen-1-yl)-2-(4'-cyanobiphenyl-4-yl)acetylene
1-(4-ethylcyclohexen-1-yl)-2-(4'-propoxybiphenyl-4-yl)acetylene
1-(4-propylcyclohexen-1-yl)-2-(4'-propoxybiphenyl-4-yl)acetylene
1-(4-butylcyclohexen-1-yl)-2-(4'-propoxybiphenyl-4-yl)acetylene
1-(4-pentylcyclohexen-1-yl)-2-(4'-propoxybiphenyl-4-yl)acetylene
1-(4-hexylcyclohexen-1-yl)-2-(4'-propoxybiphenyl-4-yl)acetylene
1-(4-ethylcyclohexen-1-yl)-2-(4'-butyloxybiphenyl-4-yl)acetylene
1-(4-propylcyclohexen-1-yl)-2-(4'-butyloxybiphenyl-4-yl)acetylene
1-(4-butylcyclohexen-1-yl)-2-(4'-butyloxybiphenyl-4-yl)acetylene
1-(4-pentylcyclohexen-1-yl)-2-(4'-butyloxybiphenyl-4-yl)acetylene
1-(4-hexylcyclohexen-1-yl)-2-(4'-butyloxybiphenyl-4-yl)acetylene
1-(4-ethylcyclohexen-1-yl)-2-(4'-ethoxybiphenyl-4-yl)acetylene
1-(4-propylcyclohexen-1-yl)-2-(4'-ethoxybiphenyl-4yl)acetylene
1-(4-butylcyclohexen-1-yl)-2-(4'-ethoxybiphenyl-4-yl)acetylene
1-(4-pentylcyclohexen-1-yl)-2-(4'-ethoxybiphenyl-4-yl)acetylene
1-(4-hexylcyclohexen-1-yl)-2-(4'-ethoxybiphenyl-4-yl)acetylene
1-(4-ethylcyclohexen-1-yl)-2-(4'-ethyl-2'-fluorobiphenyl-4-yl)-acetylene
1-(4-propylcyclohexen-1-yl)-2-(4'-ethyl-2'-fluorobiphenyl-4-yl)-acetylene
1-(4-butylcyclohexen-1-yl)-2-(4'-ethyl-2'-fluorobiphenyl-4-yl)-acetylene
1-(4-pentylcyclohexen-1-yl)-2-(4'-ethyl-2'-fluorobiphenyl-4-yl)-acetylene
1-(4-hexylcyclohexen-1-yl)-2-(4'-ethyl-2'-fluorobiphenyl4-yl)-acetylene
1-(4-ethylcyclohexen-1-yl)-2-(4'-propyl-2'-fluorobiphenyl-4-yl)-acetylene
1-(4-propylcyclohexen-1-yl)-2-(4'-propyl-2'-fluorobiphenyl-4-yl)-acetylene
1-(4-butylcyclohexen-1-yl)-2-(4'-propyl-2'-fluorobiphenyl-4-yl)-acetylene
1-(4-pentylcyclohexen-1-yl)-2-(4'-propyl-2'-fluorobiphenyl-4-yl)-acetylene
1-(4-hexylcyclohexen-1-yl)-2-(4'-propyl-2'-fluorobiphenyl-4-yl)-acetylene
1-(4-ethylcyclohexen-1-yl)-2-(4'-butyl-2'-fluorobiphenyl4-yl)-acetylene
1-(4-propylcyclohexen-1-yl)-2-(4'-butyl-2'-fluorobiphenyl-4-yl)-acetylene
1-(4-butylcyclohexen-1-yl)-2-(4'-butyl-2'-fluorobiphenyl-4-yl)-acetylene
1-(4-pentylcyclohexen-1-yl)-2-(4'-butyl-2'-fluorobiphenyl-4-yl)-acetylene
1-(4-hexylcyclohexen-1-yl)-2-(4'-butyl-2'-fluorobiphenyl-4-yl)-acetylene
1-(4-ethylcyclohexen-1-yl)-2-(4'-pentyl-2'-fluorobiphenyl-4-yl)-acetylene
1-(4-propylcyclohexen-1-yl)-2-(4'-pentyl-2'-fluorobiphenyl-4-yl)-acetylene
1-(4-butylcyclohexen-1-yl)-2-(4'-pentyl-2'-fluorobiphenyl-4-yl)-acetylene
1-(4-pentylcyclohexen-1-yl)-2-(4'-pentyl-2'-fluorobiphenyl-4-yl)-acetylene
1-(4-hexylcyclohexen-1-yl)-2-(4'-pentyl-2'-fluorobiphenyl-4-yl)-acetylene
1-(4-ethylcyclohexen-1-yl)-2-(2'-fluoro-4'-cyanobiphenyl-4-yl)-acetylene
1-(4-propylcyclohexen-1-yl)-2-(2'-fluoro-4'-cyanobiphenyl-4-yl)-acetylene
1-(4-butylcyclohexen-1-yl)-2-(2'-fluoro-4'-cyanobiphenyl-4-yl)-acetylene
1-(4-pentylcyclohexen-1-yl)-2-(2'-fluoro-4'-cyanobiphenyl-4-yl)-acetylene
1-(4-hexylcyclohexen-1-yl)-2-(2'-fluoro-4'-cyanobiphenyl4yl)-acetylene
1-[4-(4-ethylphenyl)-cyclohexen-1-yl]-2-(4-ethoxyphenyl)acetylene
1-[4-(4-propylphenyl)-cyclohexen-1-yl]-2-(4-ethoxyphenyl)acetylene
1-[4-(4-butylphenyl)-cyclohexen-1-yl]-2-(4-ethoxyphenyl)acetylene
1-[4-(4-pentylphenyl)-cyclohexen-1-yl]-2-(4-ethoxyphenyl)acetylene
1-[4-(4-hexylphenyl)-cyclohexen-1-yl]-2-(4-ethoxyphenyl)acetylene
1-[4-(4-ethylphenyl)-cyclohexen-1-yl]-2-(4-propoxyphenyl)acetylene
1-[4-(4-propylphenyl)-cyclohexen-1-yl]-2-(4-propoxyphenyl)-acetylene
1-[4-(4-butylphenyl)-cyclohexen-1-yl]-2-(4-propoxyphenyl)acetylene
1-[4-(4-pentylphenyl)-cyclohexen-1-yl]-2-(4-propoxyphenyl)-acetylene
1-[4-(4-hexylphenyl)-cyclohexen-1-yl]-2-(4-propoxyphenyl)acetylene
1-[4-(4-ethylphenyl)-cyclohexen-1-yl]-2-(4-butyloxyphenyl)-acetylene
1-[4-(4-propylphenyl)-cyclohexen-1-yl]-2-(4-butyloxyphenyl)-acetylene
1-[4-(4-butylphenyl)-cyclohexen-1-yl]-2-(4-butyloxyphenyl)-acetylene
1-[4-(4-pentylphenyl)-cyclohexen-1-yl]-2-(4-butyloxyphenyl)-acetylene
1-[4-(4-hexylphenyl)-cyclohexen-1-yl]-2-(4-butyloxyphenyl)-acetylene 1-[4-(4-ethylphenyl)-cyclohexen-1-yl]-2-(4-methoxyphenyl)-acetylene
1-[4-(4-propylphenyl)-cyclohexen-1-yl]-2-(4-methoxyphenyl)-acetylene
1-[4-(4-butylphenyl)-cyclohexen-1-yl]-2-(4-methoxyphenyl)acetylene
1-[4-(4-pentylphenyl)-cyclohexen-1-yl]-2-(4-methoxyphenyl)-acetylene
1-[4-(4-hexylphenyl)-cyclohexen-1-yl]-2-(4-methoxyphenyl)acetylene
1-[4-(4-ethylphenyl)-cyclohexen-1-yl]-2-(4-ethylphenyl)acetylene
1-[4-(4-propylphenyl)-cyclohexen-1-yl]-2-(4-ethylphenyl)acetylene
1-[4-(4-butylphenyl)-cyclohexen-1-yl]-2-(4-ethylphenyl)acetylene
1-[4-(4-pentylphenyl)-cyclohexen-1-yl]-2-(4-ethylphenyl)acetylene
1-[4-(4-hexylphenyl)-cyclohexen-1-yl]-2-(4-ethylphenyl)acetylene
1-[4-(4-ethylphenyl-cyclohexen-1-yl]-2-(4-propylphenyl)acetylene
1-[4-(4-propylphenyl)-cyclohexen-1-yl]-2-(4-propylphenyl)acetylene
1-[4-(4-butylphenyl)-cyclohexen-1-yl]-2-(4-propylphenyl)acetylene
1-[4-(4-pentylphenyl)-cyclohexen-1-yl]-2-(4-propylphenyl)acetylene
1-[4-(4-hexylphenyl)-cyclohexen-1-yl]-2-(4-propylphenyl)acetylene
1-[4-(4-ethylphenyl)-cyclohexen-1-yl]-2-(4-butylphenyl)acetylene
1-[4-(4-propylphenyl)-cyclohexen-1-yl]-2-(4-butylphenyl)acetylene
1-[4-(4-butylphenyl)-cyclohexen-1-yl]-2-(4-butylphenyl)acetylene
1-[4-(4-pentylphenyl-cyclohexen-1-yl]-2-(4-butylphenyl)acetylene
1-[4-(4-hexylphenyl)-cyclohexen-1-yl]-2-(4-butylphenyl)acetylene
1-[4-(4-ethylphenyl)-cyclohexen-1-yl]-2-(4-pentylphenyl)acetylene
1-[4-(4-propylphenyl)-cyclohexen-1-yl]-2-(4-pentylphenyl)acetylene
1-[4-(4-butylphenyl)-cyclohexen-1-yl]-2-(4-pentylphenyl)acetylene
1-[4-(4-pentylphenyl)-cyclohexen-1-yl]-2-(4-pentylphenyl)acetylene
1-[4-(4-hexylphenyl)-cyclohexen-1-yl]-2-(4-pentylphenyl)acetylene
1-[4-(4-ethylphenyl)-cyclohexen-1-yl]-2-(4-cyanophenyl)acetylene
1-[4-(4-propylphenyl)-cyclohexen-1-yl]-2-(4-cyanophenyl)acetylene
1-[4-(4-butylphenyl)-cyclohexen-1-yl]-2-(4-cyanophenyl)acetylene
1-[4-(4-pentylphenyl)-cyclohexen-1-yl]-2-(4-cyanophenyl)acetylene
1-[4-(4-hexylphenyl)-cyclohexen-1-yl]-2-(4-cyanophenyl)acetylene
1-[4-(4-ethylphenyl)-cyclohexen-1-yl]-2-(4-fluorophenyl)acetylene
1-[4-(4-propylphenyl)-cyclohexen-1-yl]-2-(4-fluorophenyl)acetylene
1-[4-(4-butylphenyl)-cyclohexen-1-yl]-2-(4-fluorophenyl)acetylene
1-[4-(4-pentylphenyl)-cyclohexen-1-yl]-2-(4-fluorophenyl)acetylene
1-[4-(4-hexylphenyl)-cyclohexen-1-yl]-2-(4-fluorophenyl)acetylene
1-[4-(4-ethylphenyl)-cyclohexen-1-yl]-2-(3-fluoro-4-cyanophenyl)-acetylene
1-[4-(4-propylphenyl)-cyclohexen-1-yl]-2-(3-fluoro-4-cyanophenyl)-acetylene
1-[4-(4-butylphenyl)-cyclohexen-1-yl]-2-(3-fluoro-4-cyanophenyl)-acetylene
1-[4-(4-pentylphenyl)-cyclohexen-1-yl]-2-(3-fluoro-4-cyanophenyl)-acetylene
1-[4-(4-hexylphenyl)-cyclohexen-1-yl]-2-(3-fluoro-4-cyanophenyl)-acetylene
1-[4-(4-ethylphenyl)-cyclohexen-1-yl]-2-(4'-cyanobiphenyl-4-yl)-acetylene
1-[4-(4-propylphenyl)-cyclohexen-1-yl]-2-(4'-cyanobiphenyl-4-yl)-acetylene
1-[4-(4-butylphenyl)-cyclohexen-1-yl]-2-(4'-cyanobiphenyl-4-yl)-acetylene
1-[4-(4-pentylphenyl)-cyclohexen-1-yl]-2-(4'-cyanobiphenyl-4-yl)-acetylene
1-[4-(4-hexylphenyl)-cyclohexen-1-yl]-2-(4'-cyanobiphenyl-4-yl)-acetylene
1-[4-(4-ethylphenyl)-cyclohexen-1-yl]-2-(3'-fluoro-4'-cyanophenyl)-acetylene
1-[4-(4-propylphenyl)-cyclohexen-1-yl]-2-(3'-fluoro-4'-cyanophenyl)-acetylene
1-[4-(4-butylphenyl)-cyclohexen-1-yl]-2-(3'-fluoro-4'-cyanophenyl)-acetylene
1-[4-(4-pentylphenyl)-cyclohexen-1-yl]-2-(3'-fluoro-4'-cyanophenyl)-acetylene
1-[4-(4-hexylphenyl)-cyclohexen-1-yl]-2-(3'-fluoro-4'-cyanophenyl)-acetylene
1-[4-(4-ethylphenyl)-cyclohexen-1-yl]-2-(4'-propylphenyl)-acetylene
1-[4-(4-propylphenyl)-cyclohexen-1-yl]-2-(4'-propylphenyl)-acetylene
1-[4-(4-butylphenyl)-cyclohexen-1-yl]-2-(4'-propylphenyl)-acetylene
1-[4-(4-pentylphenyl)-cyclohexen-1-yl]-2-(4'-propylphenyl)-acetylene
1-[4-(4-hexylphenyl)-cyclohexen-1-yl]-2-(4'-propylphenyl)acetylene
1-[4-(4-ethylphenyl)-cyclohexen-1-yl]-2-(4'-butylphenyl)acetylene
1-[4-(4-propylphenyl)-cyclohexen-1-yl]-2-(4'-butylphenyl)acetylene
1-[4-(4-butylphenyl)-cyclohexen-1-yl]-2-(4'-butylphenyl)acetylene
1-[4-(4-pentylphenyl)-cyclohexen-1-yl]-2-(4'-butylphenyl)-acetylene
1-[4-(4-hexylphenyl)-cyclohexen-1-yl]-2-(4'-butylphenyl)acetylene
1-[4-(4-ethylphenyl)-cyclohexen-1-yl]-2-(4'-pentylphenyl)acetylene
1-[4-(4-propylphenyl)-cyclohexen-1-yl]-2-(4'-pentylphenyl)-acetylene
1-[4-(4-butylphenyl)-cyclohexen-1-yl]-2-(4'-pentylphenyl)acetylene
1-[4-(4-pentylphenyl)-cyclohexen-1-yl]-2-(4'-pentylphenyl)-acetylene
1-[4-(4-hexylphenyl)-cyclohexen-1-yl]-2-(4'-pentylphenyl)acetylene
1-[4-(4-ethylcyclohexyl)-cyclohexen-1-yl]-2-(4'-butylbiphenyl-4-yl)-acetylene
1-[4-(4-propylcyclohexyl)-cyclohexen-1-yl]-2-(4'-butylbiphenyl-4-yl)-acetylene
1-[4-(4-butylcyclohexyl)-cyclohexen-1-yl]-2-(4'-butylbiphenyl-4-yl)-acetylene 1-[4-(4-pentylcyclohexyl)-cyclohexen-1-yl]-2-(4'-butyl-biphenyl-4-yl)-acetylene
1-[4-(4-hexylcyclohexyl)-cyclohexen-1-yl]-2-(4'-butyl-biphenyl-4-yl)-acetylene
1-[4-(4-ethylcyclohexyl)-cyclohexen-1-yl]-2-(4'-pentyl-biphenyl-4-yl)-acetylene
1-[4-(4-propylcyclohexyl)-cyclohexen-1-yl]-2-(4'-pentylbiphenyl-4-yl)-acetylene
1-[4-(4-butylcyclohexyl)-cyclohexen-1-yl]-2-(4'-pentyl-biphenyl-4-yl)-acetylene
1-[4-(4-pentylcyclohexyl)-cyclohexen-1-yl]-2-(4'-pentylbiphenyl-4-yl)-acetylene
1-[4-(4-ethylcyclohexyl)-cyclohexen-1-yl]-2-(4'-hexyl-biphenyl-4-yl)-acetylene
1-[4-(4-propylcyclohexyl)-cyclohexen-1-yl]-2-(4'-hexyl-biphenyl-4-yl)-acetylene
1-[4-(4-butylcyclohexyl)-cyclohexen-1-yl]-2-(4'-hexyl-biphenyl-4-yl)-acetylene
1-[4-(4-pentylcyclohexyl)-cyclohexen-1-yl]-2-(4'-hexyl-biphenyl-4-yl)-acetylene
1-[4-(4-propylcyclohexyl)-cyclohexen-1-yl]-2-(4'-ethoxybiphenyl-4-yl)-acetylene
1-[4-(4-butylcyclohexyl)-cyclohexen-1-yl]-2-(4'-ethoxybiphenyl-b 4-yl)-acetylene
1-[4-(4-pentylcyclohexyl)-cyclohexen-1-yl]-2-(4'-ethoxybiphenyl-4-yl)-acetylene
1-[4-(4-hexylcyclohexyl)-cyclohexen-1-yl]-2-(4'-ethoxybiphenyl-4-yl)-acetylene
1-[4-(4-ethylcyclohexyl)-cyclohexen-1-yl]-2-(4'-propoxybiphenyl-4-yl)-acetylene
1-[4-(4-propylcyclohexyl)-cyclohexen-1-yl]-2-(4'-propoxybiphenyl-4-yl)-acetylene
1-[4-(4-butylcyclohexyl)-cyclohexen-1-yl]-2-(4'-propoxybiphenyl-4-yl)-acetylene
1-[4-(4-pentylcyclohexyl)-cyclohexen-1-yl]-2-(4'-propoxybiphenyl-4-yl)-acetylene
1-[4-(4-hexylcyclohexyl)-cyclohexen-1-yl]-2-(4'-propoxybiphenyl-4-yl)-acetylene
1-[4-(4-ethylcyclohexyl)-cyclohexen-1-yl]-2-(3'-fluoro4'-propylbiphenyl-4-yl)-acetylene
1-[4-(4-propylcyclohexyl)-cyclohexen-1-yl]-2-(3'-fluoro4'-propylbiphenyl-4-yl)-acetylene
1-[4-(4-butylcyclohexyl)-cyclohexen-1-yl]-2-(3'-fluoro4'-propylbiphenyl-4-yl)-acetylene
1-[4-(4-pentylcyclohexyl)-cyclohexen-1-yl]-2-(3'-fluoro4'-propylbiphenyl-4-yl)-acetylene
1-[4-(4-ethylcyclohexyl)-cyclohexen-1-yl]-2-(4'-cyanobiphenyl-4-yl)-acetylene
1-[4-(4-propylcyclohexyl)-cyclohexen-1-yl]-2-(4'-cyanobiphenyl-4-yl)-acetylene
1-[4-(4-butylcyclohexyl)-cyclohexen-1-yl]-2-(4'-cyanobiphenyl-4-yl)-acetylene
1-[4-(4-ethylcyclohexyl)-cyclohexen-1-yl]-2-(3'-fluoro4'-cyano-biphenyl-4-yl)-acetylene
1-[4-(4-propylcyclohexyl)-cyclohexen-1-yl]-2-(3'-fluoro4'-cyano-biphenyl-4-yl)-acetylene
1-[4-(4-butylcyclohexyl)-cyclohexen-1-yl]-2-(3'-fluoro4'-cyano-biphenyl-4-yl)-acetylene
1-[4-(4-pentylcyclohexyl)-cyclohexen-1-yl]-2-(3'-fluoro4'-cyano-biphenyl-4-yl)-acetylene
1-[4-(4-ethylcyclohexyl)-cyclohexen-1-yl]-2-(4-ethylphenyl)-acetylene
1-[4-(4-propylcyclohexyl)-cyclohexen-1-yl]-2-(4-ethylphenyl)-acetylene
1-[4-(4-butylcyclohexyl)-cyclohexen-1-yl]-2-(4-ethylphenyl)-acetylene
1-[4-(4-pentylcyclohexyl)-cyclohexen-1-yl]-2-(4-ethylphenyl)-acetylene
1-[4-(4-hexylcyclohexyl)-cyclohexen-1-yl]-2-(4-ethylphenyl)-acetylene
1-[4-(4-ethylcyclohexyl)-cyclohexen-1-yl]-2-(4-propylphenyl)-acetylene
1-[4-(4-propylcyclohexyl]-cyclohexen-1-yl]-2-(4-propylphenyl)-acetylene
1-[4-(4-butylcyclohexyl)-cyclohexen-1-yl]-2-(4-propylphenyl)-acetylene
1-[4-(4-pentylcyclohexyl)-cyclohexen-1-yl]-2-(4-propylphenyl)-acetylene
1-[4-(4-hexylcyclohexyl)-cyclohexen-1-yl]-2-(4-propylphenyl)-acetylene
1-[4-(4-ethylcyclohexyl)-cyclohexen-1-yl]-2-(3-fluoro-4butylphenyl)-acetylene
1-[4-(4-propylcyclohexyl)-cyclohexen-1-yl]-2-(3-fluoro4-butylphenyl)-acetylene
1-[4-(4-butylcyclohexyl)-cyclohexen-1-yl]-2-(3-fluoro-4butylphenyl)-acetylene
1-[4-(4-pentylcyclohexyl)-cyclohexen-1-yl]-2-(3-fluoro4-butylphenyl)-acetylene
1-[4-(4-ethylcyclohexyl)-cyclohexen-1-yl]-2-(4-butyloxyphenyl)-acetylene
1-[4-(4-propylcyclohexyl)-cyclohexen-1-yl]-2-(4-butyloxyphenyl)-acetylene
1-[4-(4-butylcyclohexyl)-cyclohexen-1-yl]-2-(4-butyloxyphenyl)-acetylene
1-[4-(4-pentylcyclohexyl)-cyclohexen-1-yl]-2-(4-butyloxyphenyl)-acetylene
1-[4-(4-ethylcyclohexyl)-cyclohexen-1-yl]-2-(4-fluorophenyl)-acetylene
1-[4-(4-propylcyclohexyl)-cyclohexen-1-yl]-2-(4-fluorophenyl)-acetylene
1-[4-(4-butylcyclohexyl)-cyclohexen-1-yl]-2-(4-fluorophenyl)-acetylene
1-[4-(4-pentylcyclohexyl)-cyclohexen-1-yl]-2-(4-fluorophenyl)-acetylene
1-[4-(4-heptylcyclohexyl)-cyclohexen-1-yl]-2-(4-fluorophenyl)-acetylene
1-[4-(4-ethylcyclohexyl)-cyclohexen-1-yl]-2-(4-cyanophenyl)-acetylene
1-[4-(4-propylcyclohexyl)-cyclohexen-1-yl]-2-(4-cyanophenyl)-acetylene
1-[4-(4-butylcyclohexyl)-cyclohexen-1-yl]-2-(4-cyanophenyl)-acetylene
1-[4-(4-pentylcyclohexyl)-cyclohexen-1-yl]-2-(4-cyanophenyl)-acetylene
1-[4-(4-hexylcyclohexyl)-cyclohexen-1-yl]-2-(4-cyanophenyl)-acetylene

EXAMPLE 7

0.2 mol of 4-methoxy-4'-(1-hydroxy-4-pentylcyclohexyl)-tolan (prepared by reaction of a Grignard compound of 4-bromo-4'-methoxytolan with 4-pentylcyclohexanone) is heated in 400 ml of toluene and with 1 g of p-toluenesulfonic acid for 1 hour using a water separator. The reaction mixture is washed, dried and evaporated. Customary working up gives 1-(4-methoxyphenyl)-2-[4-(4-pentylcyclohexen-1-yl)-phenyl]-acetylene.

The following compounds are prepared analogously:
1-(4-ethoxyphenyl)-2-[4-(4-pentylcyclohexen-1-yl)-phenyl]acetylene
1-(4-propoxyphenyl)-2-[4-(4-pentylcyclohexen-1-yl)-phenyl]-acetylene
1-(4-butyloxyphenyl)-2-[4-(4-pentylcyclohexen-1-yl)phenyl]-acetylene
1-(4-pentyloxyphenyl)-2-[4-(4-pentylcyclohexen-1-yl)phenyl]-acetylene 1-(4-hexyloxyphenyl)-2-[4-(4-pentylcyclohexen-1-yl)phenyl]-acetylene
1-(4-methoxyphenyl)-2-[4-(4-propylcyclohexen-1-yl)phenyl]-acetylene
1-(4-ethoxyphenyl)-2-[4-(4-propylcyclohexen-1-yl)phenyl]acetylene
1-(4-propoxyphenyl)-2-[4-(4-propylcyclohexen-1-yl)phenyl]-acetylene
1-(4-butyloxyphenyl)-2-[4-(4-propylcyclohexen-1-yl)phenyl]-acetylene
1-(4-pentyloxyphenyl)-2-[4-(4-propylcyclohexen-1-yl)phenyl]-acetylene
1-(4-hexyloxyphenyl)-2-[4-(4-propylcyclohexen-1-yl)phenyl]-acetylene
1-(4-methoxyphenyl)-2-[4-(4-butylcyclohexen-1-yl)phenyl]-acetylene
1-(4-ethoxyphenyl)-2-[4-(4-butylcyclohexen-1-yl)-phenyl]acetylene
1-(4-propoxyphenyl)-2-[4-(4-butylcyclohexen-1-yl)phenyl]-acetylene
1-(4-butyloxyphenyl)-2-[4-(4-butylcyclohexen-1-yl)phenyl]-acetylene
1-(4-pentyloxyphenyl)-2-[4-(4-butylcyclohexen-1-yl)phrenyl]-acetylene
1-(4-hexyloxyphenyl)-2-[4-(4-butylcyclohexen-1-yl)phenyl]-acetylene
1-(4-ethylphenyl)-2-[4-(4-ethylcyclohexen-1-yl)-phenyl]acetylene
1-(4-propylphenyl)-2-[4-(4-ethylcyclohexen-1-yl)-phenyl]acetylene
1-(4-butylphenyl)-2-[4-(4-ethylcyclohexen-1-yl)-phenyl]acetylene
1-(4-pentylphenyl)-2-[4-(4-ethylcyclohexen-1-yl)-phenyl]acetylene
1-(4-ethylphenyl)-2-[4-(4-propylcyclohexen-1-yl)-phenyl]acetylene
1-(4-propylphenyl)-2-[4-(4-propylcyclohexen-1-yl)phenyl]acetylene
1-(4-butylphenyl)-2-[4-(4-propylcyclohexen-1-yl)-phenyl]acetylene
1-(4-pentylphenyl)-2-[4-(4-propylcyclohexen-1-yl)phenyl]acetylene
1-(4-ethylphenyl)-2-[4-(4-butylcyclohexen-1-yl)-phenyl]acetylene
1-(4-propylphenyl)-2-[4-(4-butylcyclohexen-1-yl)-phenyl]acetylene
1-(4-butylphenyl)-2-[4-(4-butylcyclohexen-1-yl)-phenyl]acetylene
1-(4-pentylphenyl)-2-[4-(4-butylcyclohexen-1-yl)-phenyl]acetylene
1-(4-propylphenyl)-2-[4-(4-pentylcyclohexen-1-yl)phenyl]-acetylene
1-(4-butylphenyl)-2-[4-(4-pentylcyclohexen-1-yl)-phenyl]acetylene
1-(4-pentylphenyl)-2-[4-(4-pentylcyclohexen-1-yl)phenyl]-acetylene
1-(4-ethylphenyl)-2-[4-(4-hexylcyclohexen-1-yl)-phenyl]acetylene
1-(4-propylphenyl)-2-[4-(4-hexylcyclohexen-1-yl)-phenyl]acetylene
1-(4-butylphenyl)-2-[4-(4-hexylcyclohexen-1-yl)-phenyl]acetylene
1-(4-pentylphenyl)-2-[4-(4-hexylcyclohexen-1-yl)-phenyl]acetylene

EXAMPLE 8

Starting from 1-(trans-4-propylcyclohexyl)-2-(trans-4-pentylcyclohexyl)-1,2-ethanedionebishydrazone, the corresponding 1-(trans-4-propylcyclohexyl)-2-(trans4-pentylcyclohexyl)-acetylene is obtained in the presence of copper(I) chloride in pyridine analogously to the instructions in the literature (Tsuji, Takanashi, Kajimoto, Tetrahedron Letters. 1973, 4573).

The following compounds are prepared analogously:
1-(trans-4-methylcyclohexyl)-2-(trans-4-ethylcyclohexyl)acetylene
1-(trans-4-methylcyclohexyl)-2-(trans-4-propylcyclohexyl)acetylene
1-(trans-4-methylcyclohexyl)-2-(trans-4-butylcyclohexyl)acetylene
1-(trans-4-methylcyclohexyl)-2-(trans-4-pentylcyclohexyl)acetylene
1-(trans-4-methylcyclohexyl)-2-(trans-4-hexylcyclohexyl)acetylene
1-(trans-4-methylcyclohexyl)-2-(trans-4-heptylcyclohexyl)acetylene
1-(trans-4-ethylcyclohexyl)-2-(trans-4-propylcyclohexyl)acetylene
1-(trans-4-ethylcyclohexyl)-2-(trans-4-butylcyclohexyl)acetylene
1-(trans-4-ethylcyclohexyl)-2-(trans-4-pentylcyclohexyl)acetylene
1-(trans-4-ethylcyclohexyl)-2-(trans-4-hexylcyclohexyl)acetylene
1-(trans-4-ethylcyclohexyl)-2-(trans-4-heptylcyclohexyl)acetylene
1-(trans-4-propylcyclohexyl)-2-(trans-4-butylcyclohexyl)acetylene
1-(trans-4-propylcyclohexyl)-2-(trans-4-hexylcyclohexyl)acetylene
1-(trans-4-propylcyclohexyl)-2-(trans-4-heptylcyclohexyl)acetylene
1-(trans-butylcyclohexyl)-2-(trans-4-pentylcyclohexyl)acetylene
1-(trans-butylcyclohexyl)-2-(trans-4-hexylcyclohexyl)acetylene
1-(trans-butylcyclohexyl)-2-(trans-4-heptylcyclohexyl)acetylene

EXAMPLE 9

0.105 mol of n-butyllithium (1.5 mol in n-hexane) is added to a mixture of 0.1 mol of difluorophenetole, 0.1 mol of tetramethylethylenediamine (TMEDA) and 200 ml of tetrahydrofuran at −70° to -60°. The mixture is stirred at this temperature for a further 3 hours and 0.1 mol of $I_2$ in 150 ml of tetrahydrofuran is then added. The mixture is subsequently hydrolyzed at −20° with a 5% sodium thiosulfate solution. After working up by extraction, the crude product is purified by distillation in vacuo.

0.01 mol of this iodine compound is warmed at 60° to 70° with 0.01 mol of trans-4-pentylcyclohexylacetylene, 30 ml of triethylamine, 0.2 mmol of Pd catalyst and 0.1 mmol of CuI for 15 hours. The reaction mixture is diluted with petroleum ether and filtered. Evaporation and purification give 1-(trans-4-pentylcyclohexyl)-2-(2,3-difluoro-4-ethoxyphenyl)-acetylene. The following compounds are prepared analogously:
1-(trans-4-methylcyclohexyl)-2-(2,3-difluoro-4-ethoxyphenyl)-acetylene
1-(trans-4-ethylcyclohexyl)-2-(2,3-difluoro-4-ethoxyphenyl)-acetylene
1-(trans-4-propylcyclohexyl)-2-(2,3-difluoro-4-ethoxyphenyl)-acetylene
1-(trans-4-butylcyclohexyl)-2-(2,3-difluoro-4-ethoxyphenyl)-acetylene 1-(trans-4-hexylcyclohexyl)-2-(2,3-difluoro-4-ethoxyphenyl)-acetylene
1-(trans-4-heptylcyclohexyl)-2-(2,3-difluoro-4-ethoxyphenyl)-acetylene
1-(trans-4-methylcyclohexyl)-2-(2,3-difluoro-4-methoxyphenyl)-acetylene
1-(trans-4-ethylcyclohexyl)-2-(2,3-difluoro-4-methoxyphenyl)-acetylene
1-(trans-4-propylcyclohexyl)-2-(2,3-difluoro-4-methoxyphenyl)-acetylene
1-(trans-4-butylcyclohexyl)-2-(2,3-difluoro-4-methoxyphenyl)-acetylene
1-(trans-4-pentylcyclohexyl)-2-(2,3-difluoro-4-methoxyphenyl)-acetylene
1-(trans-4-hexylcyclohexyl)-2-(2,3-difluoro-4-methoxyphenyl)-acetylene
1-(trans-4-heptylcyclohexyl)-2-(2,3-difluoro-4-methoxyphenyl)-acetylene
1-(trans-4-methylcyclohexyl)-2-(2,3-difluoro-4-propoxyphenyl)-acetylene
1-(tranS-4-ethylcyclohexyl)-2-(2,3-difluoro-4-propoxyphenyl)-acetylene
1-(trans-4-propylcyclohexyl)-2-(2,3-difluoro-4-propoxyphenyl)-acetylene
1-(trans-4-butylcyclohexyl)-2-(2,3-difluoro-4-propoxyphenyl)-acetylene
1-(trans-4-pentylcyclohexyl)-2-(2,3-difluoro-4-propoxyphenyl)-acetylene
1-(trans-4-hexylcyclohexyl)-2-(2,3-difluoro-4-propoxyphenyl)-acetylene
1-(trans-4-heptylcyclohexyl)-2-(2,3-difluoro-4-propoxyphenyl)-acetylene
1-(trans-4-methylcyclohexyl)-2-(2,3-difluoro-4-butoxyphenyl)-acetylene
1-(trans-4-ethylcyclohexyl)-2-(2,3-difluoro-4-butoxyphenyl)-acetylene
1-(trans-4-propylcyclohexyl)-2-(2,3-difluoro-4-butoxyphenyl)-acetylene
1-(trans-4-butylcyclohexyl)-2-(2,3-difluoro-4-butoxyphenyl)-acetylene
1-(trans-4-pentylcyclohexyl)-2-(2,3-difluoro-4-butoxyphenyl)-acetylene
1-(trans-4-hexylcyclohexyl)-2-(2,3-difluoro-4-butoxyphenyl)-acetylene
1-(trans-4-heptylcyclohexyl)-2-(2,3-difluoro-4-butoxyphenyl)-acetylene
1-(trans-4-methylcyclohexyl)-2-(2,3-difluoro-4-pentyloxyphenyl)-acetylene
1-(trans-4-ethylcyclohexyl)-2-(2,3-difluoro-4-pentyloxyphenyl)-acetylene
1-(trans-4-propylcyclohexyl)-2-(2,3-difluoro-4-pentyloxyphenyl)-acetylene
1-(trans-4-butylcyclohexyl)-2-(2,3-difluoro-4-pentyloxyphenyl)-acetylene
1-(trans-4-pentylcyclohexyl)-2-(2,3-difluoro-4-pentyloxyphenyl)-acetylene
1-(trans-4-hexylcyclohexyl)-2-(2,3-difluoro-4-pentyloxyphenyl)-acetylene
1-(trans-4-heptylcyclohexyl)-2-(2,3-difluoro-4-pentyloxyphenyl)-acetylene
1-(trans-4-methylcyclohexyl)-2-(2,3-difluoro-4-hexyloxyphenyl)-acetylene
1-(trans-4-ethylcyclohexyl)-2-(2,3-difluoro-4-hexyloxyphenyl)-acetylene
1-(trans-4-propylcyclohexyl)-2-(2,3-difluoro-4-hexyloxyphenyl)-acetylene
1-(trans-4-butylcyclohexyl)-2-(2,3-difluoro-4-hexyloxyphenyl)-acetylene
1-(trans-4-pentylcyclohexyl)-2-(2,3-difluoro-4-hexyloxyphenyl)-acetylene
1-(trans-4-hexylcyclohexyl)-2-(2,3-difluoro-4-hexyloxyphenyl)-acetylene
1-(trans-4-heptylcyclohexyl)-2-(2,3-difluoro-4-hexyloxyphenyl)-acetylene
1-[trans-4-(4-methylphenyl)cyclohexyl]-2-(2,3-difluoro4-methoxyphenyl)-acetylene
1-[trans-4-(4-ethylphenyl)cyclohexyl]-2-(2,3-difluoro4-methoxyphenyl)-acetylene
1-[trans-4-(4-propylphenyl)cyclohexyl]-2-(2,3-difluoro-4-methoxyphenyl)-acetylene
1-[trans-4-(4-butylphenyl)cyclohexyl]-2-(2,3-difluoro-4-methoxyphenyl)-acetylene
1-[trans-4-(4-pentylphenyl)cyclohexyl]-2-(2,3-difluoro-4-methoxyphenyl)-acetylene
1-[trans-4-(4-hexylphenyl)cyclohexyl]-2-(2,3-difluoro-4-methoxyphenyl)-acetylene
1-[trans-4-(4-heptylphenyl)cyclohexyl]-2-(2,3-difluoro-4-methoxyphenyl)-acetylene
1-[trans-4-(4-methylphenyl)cyclohexyl]-2-(2,3-difluoro-4-propoxyphenyl)-acetylene
1-[trans-4-(4-ethylphenyl)cyclohexyl]-2-(2,3-difluoro-4-propoxyphenyl)-acetylene
1-[trans-4-(4-propylphenyl)cyclohexyl]-2-(2,3-difluoro-4-propoxyphenyl)-acetylene
1-[trans-4-(4-butylphenyl)cyclohexyl]-2-(2,3-difluoro-4-propoxyphenyl)-acetylene
1-[trans-4-(4-pentylphenyl)cyclohexyl]-2-(2,3-difluoro-4-propoxyphenyl)-acetylene
1-[trans-4-(4-hexylphenyl)cyclohexyl]-2-(2,3-difluoro-4-propoxyphenyl)-acetylene
1-[trans-4-(4-heptylphenyl)cyclohexyl]-2-(2,3-difluoro-4-propoxyphenyl)-acetylene
1-[trans-4-(4-methylphenyl)cyclohexyl]-2-(2,3-difluoro-4-butoxyphenyl)-acetylene
1-[trans-4-(4-ethylphenyl)cyclohexyl]-2-(2,3-difluoro-4-butoxyphenyl)-acetylene
1-[trans-4-(4-propylphenyl)cyclohexyl]-2-(2,3-difluoro-4-butoxyphenyl)-acetylene
1-[trans-4-(4-butylphenyl)cyclohexyl]-2-(2,3-difluoro-4-butoxyphenyl)-acetylene
1-[trans-4-(4-pentylphenyl)cyclohexyl]-2-(2,3-difluoro-4-butoxyphenyl)-acetylene
1-[trans-4-(4-hexylphenyl)cyclohexyl]-2-(2,3-difluoro-4-butoxyphenyl)-acetylene
1-[trans-4-(4-heptylphenyl)cyclohexyl]-2-(2,3-difluoro-4-butoxyphenyl)-acetylene
1-[trans-4-(4-methylphenyl)cyclohexyl]-2-(2,3-difluoro-4-pentyloxyphenyl)-acetylene
1-[trans-4-(4-ethylphenyl)cyclohexyl]-2-(2,3-difluoro-4-pentyloxyphenyl)-acetylene
1-[trans-4-(4-propylphenyl)cyclohexyl]-2-(2,3-difluoro-4-pentyloxyphenyl)-acetylene
1-[trans-4-(4-butylphenyl)cyclohexyl]-2-(2,3-difluoro-4-pentyloxyphenyl)-acetylene
1-[trans-4-(4-pentylphenyl)cyclohexyl]-2-(2,3-difluoro-4-pentyloxyphenyl)-acetylene
1-[trans-4-(4-hexylphenyl)cyclohexyl]-2-(2,3-difluoro-4-pentyloxyphenyl)-acetylene
1-[trans-4-(4-heptylphenyl)cyclohexyl]-2-(2,3-difluoro-4-pentyloxyphenyl)-acetylene
1-[trans-4-(trans-4-ethylcyclohexyl)cyclohexyl]-2-(2,3-difluoro-4-ethoxyphenyl)-acetylene
1-[trans-4-(trans-4-propylcyclohexyl)cyclohexyl]-2-(2,3-difluoro-4-ethoxyphenyl)-acetylene
1-[trans-4-(trans-4-butylcyclohexyl)cyclohexyl]-2-(2,3-difluoro-4-ethoxyphenyl)-acetylene 1-[trans-4-(trans-4-pentylcyclohexyl)cyclohexyl]-2-(2,3-difluoro-4-ethoxyphenyl)-acetylene
1-[trans-4-(trans-4-ethylcyclohexyl)cyclohexyl]-2-(2,3-difluoro-4-propoxyphenyl)-acetylene
1-[trans-4-(trans-4-propylcyclohexyl)cyclohexyl]-2-(2,3-difluoro-4-propoxyphenyl)-acetylene
1-[trans-4-(trans-4-butylcyclohexyl)cyclohexyl]-2-(2,3-difluoro-4-propoxyphenyl)-acetylene
1-[trans-4-(trans-4-pentylcyclohexyl)cyclohexyl]-2-(2,3-difluoro-4-propoxyphenyl)-acetylene
1-[trans-4-(trans-4-ethylcyclohexyl)cyclohexyl]-2-(2,3-difluoro-4-butoxyphenyl)-acetylene
1-[trans-4-(trans-4-propylcyclohexyl)cyclohexyl]-2-(2,3-difluoro-4-butoxyphenyl)-acetylene
1-[trans-4-(trans-4-butylcyclohexyl)cyclohexyl]-2-(2,3-difluoro-4-butoxyphenyl)-acetylene
1-[trans-4-(trans-4-pentylcyclohexyl)cyclohexyl]-2-(2,3-difluoro-4-butoxyphenyl)-acetylene
1-[trans-4-(trans-4-ethylcyclohexyl)cyclohexyl]-2-(2,3-difluoro-4-pentyloxyphenyl)-acetylene
1-[trans-4-(trans-4-propylcyclohexyl)cyclohexyl]-2-(2,3-difluoro-4-pentyloxyphenyl)-acetylene
1-[trans-4-(trans-4-butylcyclohexyl)cyclohexyl]-2-(2,3-difluoro-4-pentyloxyphenyl)-acetylene
1-[trans-4-(trans-4-pentylcyclohexyl)cyclohexyl]-2-(2,3-difluoro-4-pentyloxyphenyl)-acetylene

EXAMPLE 10

A mixture of 0.06 mol of trans-4-pentylcyclohexylacetylene, 0.06 mol of 4-trifluoromethyl-bromobenzene, 250 ml of triethylamine, 1.2 mmol of Pd(II) catalyst and 0.6 mmol of CuI is stirred at room temperature for 15 hours. The reaction mixture is diluted with petroleum ether and filtered. Evaporation and purification give 1-(trans-4-pentylcyclohexyl)-2-(4-trifluoromethylphenyl)acetylene of M.=43°.

The following compounds are prepared analogously:
1-(trans-4-methylcyclohexyl)-2-(4-trifluoromethylphenyl)acetylene
1-(trans-4-ethylcyclohexyl)-2-(4-trifluoromethylphenyl)acetylene
1-(trans-4-propylcyclohexyl)-2-(4-trifluoromethylphenyl)acetylene
1-(trans-4-butylcyclohexyl)-2-(4-trifluoromethylphenyl)acetylene
1-(trans-4-hexylcyclohexyl)-2-(4-trifluoromethylphenyl)acetylene
1-(trans-4-heptylcyclohexyl)-2-(4-trifluoromethylphenyl)acetylene
1-(trans-4-methylcyclohexyl)-2-(4-pentafluoroethylphenyl)acetylene
1-(trans-4-ethylcyclohexyl)-2-(4-pentafluoroethylphenyl)acetylene
1-(trans-4-propylcyclohexyl)-2-(4-pentafluoroethylphenyl)acetylene
1-(trans-4-butylcyclohexyl)-2-(4-pentafluoroethylphenyl)acetylene
1-(trans-4-pentylcyclohexyl)-2-(4-pentafluoroethylphenyl)acetylene
1-(trans-4-hexylcyclohexyl)-2-(4-pentafluoroethylphenyl)acetylene
1-(trans-4-heptylcyclohexyl)-2-(4-pentafluoroethylphenyl)acetylene
1-[trans-4-(4-methylphenyl)cyclohexyl]-2-(4-trifluoromethylphenyl)-acetylene
1-[trans-4-(4-ethylphenyl)cyclohexyl]-2-(4-trifluoromethylphenyl)-acetylene
1-[trans-4-(4-propylphenyl)cyclohexyl]-2-(4-trifluoromethylphenyl)-acetylene
1-[trans-4-(4-butylphenyl)cyclohexyl]-2-(4-trifluoromethylphenyl)-acetylene
1-[trans-4-(4-pentylphenyl)cyclohexyl]-2-(4-trifluoromethylphenyl)-acetylene
1-[trans-4-(4-hexylphenyl)cyclohexyl]-2-(4-trifluoromethylphenyl)-acetylene
1-[trans-4-(4-heptylphenyl)cyclohexyl]-2-(4-trifluoromethylphenyl)-acetylene
1-[trans-4-(trans-4-methylcyclohexyl)cyclohexyl]-2-(4(4-trifluoromethylphenyl)-acetylene
1-[trans-4-(trans-4-ethylcyclohexyl)cyclohexyl]-2-(4(4-trifluoromethylphenyl)-acetylene
1-[trans-4-(trans-4-propylcyclohexyl)cyclohexyl]-2-(4(4-trifluoromethylphenyl)-acetylene
1-[trans-4-(trans-4-butylcyclohexyl)cyclohexyl]-2-(4(4-trifluoromethylphenyl)-acetylene
1-[trans-4-(trans-4-pentylcyclohexyl)cyclohexyl]-2-(4(4-trifluoromethylphenyl)-acetylene
1-[trans-4-(trans-4-hexylcyclohexyl)cyclohexyl]-2-(4(4-trifluoromethylphenyl)-acetylene
1-[trans-4-(trans-4-heptylcyclohexyl)cyclohexyl]-2-(4(4-trifluoromethylphenyl)-acetylene

EXAMPLE 11

A mixture of 0.01 mol of 5-methylpyridin-2-yl-acetylene (which can be prepared from 5-methyl-2-bromopyridine by reaction with trimethylsilyl-acetylene and Pd catalyst and subsequent splitting off of the trimethylsilyl group), 0.01 mol of 4-iodo-2,3-difluorophenetole (for the preparation, see Example 9), 30 ml of triethylamine, 0.2 mmol of Pd catalyst and 0.1 mmol of CuI is stirred at room temperature for 24 hours. The reaction mixture is diluted with petroleum ether and filtered over silica gel. Evaporation and purification give 1-(5methylpyridin-2-yl)-2-(2,3-difluoro-4-ethoxyphenyl) acetylene.

The following compounds are prepared analogously:
1-(5-ethylpyridin-2-yl)-2-(2,3-difluoro-4-ethoxyphenyl)acetylene
1-(5-propylpyridin-2-yl)-2-(2,3-difluoro-4-ethoxyphenyl)acetylene
1-(5-butylpyridin-2-yl)-2-(2,3-difluoro-4-ethoxyphenyl)acetylene
1-(5-pentylpyridin-2-yl)-2-(2,3-difluoro-4-ethoxyphenyl)acetylene
1-(5-hexylpyridin-2-yl)-2-(2,3-difluoro-4-ethoxyphenyl)acetylene
1-(5-heptylpyridin-2-yl)-2-(2-3-difluoro-4-ethoxyphenyl)acetylene
1-(5-methylpyridin-2-yl)-2-(2,3-difluoro-4-methoxyphenyl)acetylene
1-(5-ethylpyridin-2-yl)-2-(2,3-difluoro-4-methoxyphenyl)acetylene
1-(5-propylpyridin-2-yl)-2-(2,3-difluoro-4-methoxyphenyl)acetylene
1-(5-butylpyridin-2-yl)-2-(2,3-difluoro-4-methoxyphenyl)acetylene
1-(5-pentylpyridin-2-yl)-2-(2,3-difluoro-4-methoxyphenyl)acetylene
1-(5-hexylpyridin-2-yl)-2-(2,3-difluoro-4-methoxyphenyl)acetylene
1-(5-heptylpyridin-2-yl)-2-(2,3-difluoro-4-methoxyphenyl)acetylene
1-(5-methylpyridin-2-yl)-2-(2,3-difluoro-4-propoxyphenyl)acetylene 1-(5-ethylpyridin-2-yl)-2-(2,3-difluoro-4-propoxyphenyl)acetylene
1-(5-propylpyridin-2-yl)-2-(2,3-difluoro-4-propoxyphenyl)acetylene
1-(5-butylpyridin-2-yl)-2-(2,3-difluoro-4-propoxyphenyl)acetylene
1-(5-pentylpyridin-2-yl)-2-(2,3-difluoro-4-propoxyphenyl)acetylene
1-(5-hexylpyridin-2-yl)-2-(2,3-difluoro-4-propoxyphenyl)acetylene
1-(5-heptylpyridin-2-yl)-2-(2,3-difluoro-4-propoxyphenyl)acetylene
1-(5-methylpyridin-2-yl)-2-(2,3-difluoro-4-butoxyphenyl)acetylene
1-(5-ethylpyridin-2-yl)-2-(2,3-difluoro-4-butoxyphenyl)acetylene
1-(5-propylpyridin-2-yl)-2-(2,3-difluoro-4-butoxyphenyl)acetylene
1-(5-butylpyridin-2-yl)-2-(2,3-difluoro-4-butoxyphenyl)acetylene
1-(5-pentylpyridin-2-yl)-2-(2,3-difluoro-4-butoxyphenyl)acetylene
1-(5-hexylpyridin-2-yl)-2-(2,3-difluoro-4-butoxyphenyl)acetylene
1-(5-heptylpyridin-2-yl)-2-(2,3-difluoro-4-butoxyphenyl)acetylene
1-(5-methylpyridin-2-yl)-2-(2,3-difluoro-4-pentyloxyphenyl)-acetylene
1-(5-ethylpyridin-2-yl)-2-(2,3-difluoro-4-pentyloxyphenyl)-acetylene
1-(5-propylpyridin-2-yl)-2-(2,3-difluoro-4-pentyloxyphenyl)-acetylene
1-(5-butylpyridin-2-yl)-2-(2,3-difluoro-4-pentyloxyphenyl)-acetylene
1-(5-pentylpyridin-2-yl)-2-(2,3-difluoro-4-pentyloxyphenyl)-acetylene
1-(5-hexylpyridin-2-yl)-2-(2,3-difluoro-4-pentyloxyphenyl)-acetylene
1-(5-heptylpyridin-2-yl)-2-(2,3-difluoro-4-pentyloxyphenyl)-acetylene

EXAMPLE A

A liquid crystal phase consisting of
9% of r-1-cyano-cis-4-(trans-4-propylcyclohexyl)-1-propyl-cyclohexane,
5% of r-1-cyano-1-propyl-cis-4-(4'-propylbiphenyl-4-yl)cyclohexane,
26% of 2-fluoro-4-ethyl-4'-[2-(trans-4-propylcyclohexyl)ethyl]-biphenyl,
25% of 2-fluoro-4-pentyl-4'-[2-(trans-4-propylcyclohexyl)ethyl]-biphenyl,
23% of 2-fluoro-4-ethyl-4'-[2-(trans-4-pentylcyclohexyl)ethyl]-biphenyl,
5% of 4-(trans-4-propylcyclohexyl)-2'-fluoro-4'-(trans-4-propylcyclohexyl)-biphenyl
and
7% of 1-[4-(trans-4-propylcyclohexyl)phenyl]-2-(5-methyl-pyridin-2-yl)-acetylene
has a clear point of 109° and $\Delta\epsilon = -1.1$.

I claim:

1. An ethyne derivative of Formula I

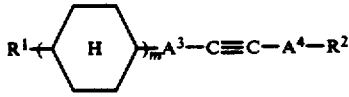

wherein
R$^1$ and R$^2$ in each case independently of one another are straight-chain alkyl, alkoxy, or oxaalkyl having 1 to 15 C atoms;
m is 1 or 1; and
A$^3$ and A$^4$ are each independently 1,4-phenylene, pyridine-2,5-diyl, or pyrimidine-2,5-diyl,
with the proviso that only one of the groups A$^3$ and A$^4$ is pyridine2,5-diyl or pyrimidine-2,5-diyl.

2.

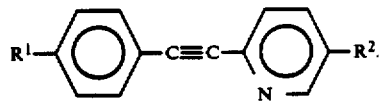

, a compound of claim 5.

3. A liquid crystal phase containing at least two liquid crystal components, wherein at least one component is a compound of Formula i according to claim 7

4. A liquid crystal display element containing at least one liquid crystal phase, wherein said liquid crystal phase is one according to claim 3.

5. An ethylene derivative of claim 1, of the formula

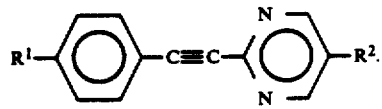

6. An ethylene derivative of claim 1, of the formula

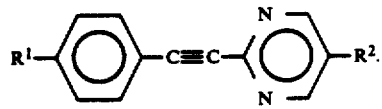

* * * * *

UNITED STATES PATENT AND TRADEMARK OFFICE
CERTIFICATE OF CORRECTION

PATENT NO. : 5,068,053
DATED : November 26, 1991
INVENTOR(S) : Volker Reiffenrath et al.

It is certified that error appears in the above-identified patent and that said Letters Patent is hereby corrected as shown below:

Column 62:   Claim 1; Line 7: reads - - -

( M is 1 or 1; )   Should read - - -

" M is 0 or 1;"

Claim III; Line 3: reads - - -

( a compound of Formula i according to claim 7 )

Should read - - -

" a compound of Formula 1 according to claim 1"

In claim 5 & 6 change (ethylene) to read - - -

"ethynyl"

Signed and Sealed this

Fourth Day of May, 1993

Attest:

MICHAEL K. KIRK

*Attesting Officer*   Acting Commissioner of Patents and Trademarks